US006750054B2

(12) United States Patent
Walke et al.

(10) Patent No.: US 6,750,054 B2
(45) Date of Patent: Jun. 15, 2004

(54) HUMAN SEMAPHORIN HOMOLOGS AND POLYNUCLEOTIDES ENCODING THE SAME

(75) Inventors: D. Wade Walke, Spring, TX (US); Xiaoming Wang, Northbrook, IL (US); John Scoville, Houston, TX (US); C. Alexander Turner, Jr., The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 396 days.

(21) Appl. No.: 09/854,845

(22) Filed: May 14, 2001

(65) Prior Publication Data

US 2002/0098491 A1 Jul. 25, 2002

Related U.S. Application Data

(60) Provisional application No. 60/205,274, filed on May 18, 2000, and provisional application No. 60/208,893, filed on Jun. 2, 2000.

(51) Int. Cl.[7] .......................... C12N 15/63; C12N 5/10; C07H 21/02; C07H 21/04
(52) U.S. Cl. ..................... 435/320.1; 435/325; 536/23.5
(58) Field of Search .............................. 435/320.1, 325; 536/23.5

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,494,595 A | 2/1996 | Nieh |
| 5,556,752 A | 9/1996 | Lockhart et al. |
| 5,700,637 A | 12/1997 | Southern |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 5,981,222 A | 11/1999 | Jacobs et al. |
| 6,013,781 A | 1/2000 | Goodman et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| | | |
|---|---|---|
| WO | WO 00/11015 A1 | 3/2000 |
| WO | WO 01/32707 A1 | 5/2001 |

OTHER PUBLICATIONS

Nagase et al., DNA Res., vol. 7, pp. 143–150, 2000.*

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Lam et al, 1991, "A new type of synthetic peptide library for identifying ligand–binding activity", Nature 354:82–86.

Lavitrano et al, 1989, "Sperm Cells ad Vectors for Introducing Froeign DNA into Eggs: Genetic Transformation of Mice", Cell 57:717–723.

(List continued on next page.)

*Primary Examiner*—Gary Kunz
*Assistant Examiner*—Stephen Gucker

(57) ABSTRACT

Novel human polynucleotide and polypeptide sequences are disclosed that can be used in therapeutic, diagnostic, and pharmacogenomic application.

12 Claims, No Drawings

OTHER PUBLICATIONS

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heratable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Adams et al., "A Novel Class of Murine Semaphorins with Homology to Thrombospondinis Differentially Expressed during early Embryogenesis," Mechanisms of Development, Elsevier Science Ireland Ltd., IE, vol. 57, 1996, pp. 33–45, XP000996385, ISSN: 0925–4773.

Database EMBL 'Online' Adams et al., "*M.musculus* mRNA for semaphorin G," Jun. 30, 1996, Database accession No. X97818, Q60519, XP002219588.

Database EMBL 'Online' Ohara, et al., "*Homo sapiens* mRNA for KIAA1445 protein, partial cds.," May 23, 2000, Database accession No. AB040878, Q9P283, XP002219589.

Simmons et al., "Molecular cloning and mapping of human semaphorin F from the Cri–du–chat candidate interval," Biochemical and Biophysical Research Communications, vol. 242, No. 3, Jan. 26, 1998, pp. 685–691, XP002219587, ISSN: 0006–291X.

International Search Report, International Application No. PCT/US01/15489, May 14, 2001.

* cited by examiner

HUMAN SEMAPHORIN HOMOLOGS AND POLYNUCLEOTIDES ENCODING THE SAME

The present application claims the benefit of U.S. Provisional Application Nos. 60/205,274 and 60/208,893 which were filed on May 18, 2000 and Jun. 2, 2000, respectively. These U.S. Provisional Applications are herein incorporated by reference in their entirety.

1. INTRODUCTION

The present invention relates to the discovery, identification, and characterization of novel human polynucleotides encoding a protein that shares sequence similarity with mammalian semaphorin proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of physiological disorders or diseases, and cosmetic or nutriceutical applications.

2. BACKGROUND OF THE INVENTION

Semaphorins are members of a superfamily of structurally related proteins that have been associated with axon guidance. Their expression in non-neural tissues indicate that semaphorins can regulate biology in ways beyond axon guidance.

3. SUMMARY OF THE INVENTION

The present invention relates to the discovery, identification, and characterization of nucleotides that encode novel human proteins, and the corresponding amino acid sequences of these proteins. The novel human protein (NHP) described for the first time herein share structural similarity with mammalian semaphorins and particularly semaphorin G (SEQ ID NOS: 1–17) and semaphorin G (subclass 4) (SEQ ID NOS: 18–50).

The novel human nucleic acid sequences described herein, encode alternative proteins/open reading frames (ORFs) of 1049, 1093, 1034, 1078, 1151, 1136, 954, 939, 215, 496, 702, 697, 843, 838, 870, 865, 116, 397, 603, 598, 744, 739, 771, and 766 amino acids in length (see respectively SEQ ID NOS: 2, 4, 6, 8, 10, 12, 14, 16, 19, 21, 23, 25, 27, 29, 31, 33, 35, 37, 39, 41, 43, 45, 47, and 49).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–50 are "knocked-out" they provide a method of identifying phenotypic expression of the particular gene as well as a method of assigning function to previously unknown genes. To this end, several gene trapped knockout ES cells have been generated in murine homologs of the described NHPs. Additionally, the unique NHP sequences described in SEQ ID NOS:1–50 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NO:17 and SEQ ID NO:50 describe full length NHP ORFs and flanking sequences.

5. DETAILED DESCRIPTION OF THE INVENTION

The NHP, described for the first time herein, are novel proteins that are widely expressed. SEQ ID NO:1–17 are novel NHPs expressed in, inter alia, human cell lines, and human brain, pituitary, cerebellum, kidney, prostate, testis, thyroid, adrenal gland, pancreas, salivary gland, heart, uterus, cervix, pericardium, fetal kidney and fetal lung cells. SEQ ID NO:18–50 describe for the first time herein, are novel proteins that are expressed in, inter alia, human cell lines, human brain, fetal brain, lymph node, mammary gland, pituitary gland, placenta, prostate, kidney, thyroid, and umbilical vein endothelial cells.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–50 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–50, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–50 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–50.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–50 provides detailed information about transcriptional changes involved in a specific pathway, potentially leading to the identification of novel components or gene functions that manifest themselves as novel phenotypes.

Probes consisting of sequences first disclosed in SEQ ID NOS:1–50 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–50 can be utilized in microarrays or other assay formats, to screen collections of genetic material from patients who have a particular medical condition. These investigations can also be carried out using the sequences first disclosed in SEQ ID NOS:1–50 in silico and by comparing previously collected genetic databases and the disclosed sequences using computer software known to those in the art.

Thus the sequences first disclosed in SEQ ID NOS:1–50 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–50. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, example, obesity, behavioral disorders, colitis or spastic colon, high blood pressure, depression, connective tissue disorders, infertility, etc.) or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo;

these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human gene trapped sequences, and cDNA products isolated from human brain and kidney mRNA (SEQ ID NOS: 1–17) and human fetal brain and kidney libraries (Edge Biosystems, Gaithersburg, Md.)(SEQ ID NOS 18–50).

The described sequences share substantial structural similarity with a variety of proteins, including, but not limited to, semaphorins G and F. Because of their potential medical significance, semaphorin protein homologs have been subject to considerable scientific scrutiny as evidenced in U.S. Pat. Nos. 5,981,222 and 6,013,781, which are herein incorporated by reference, and which describe various applications, uses, and compositions in which the presently described NHPs can be advantageously applied.

The NHP sequences described in SEQ ID NOS: 1–17 can contain a variety of polymorphisms such as A-G transitions that can occur in the sequence regions represented by nucleotide positions nos. 100, 232, and 406 of, for example, SEQ ID NO:1 that can give rise to a N or D being present at corresponding amino acid positions 34, 78, and 136 of SEQ ID NO:2, and a polymorphism at nucleotide position 1974 of, for example, SEQ ID NO:1 which can give rise to GTG being present or deleted which causes an accompanying presence or deletion of a V at corresponding amino acid position 658, for example, of SEQ ID NO:2.

The NHP sequences described in SEQ ID NOS: 18–50 can also contain a couple of polymorphisms such as a translationally silent C-T transition that can occur in the sequence regions represented by nucleotide position no. 804 of, for example, SEQ ID NO: 28, and a T-C transition at nucleotide position 2060 of, for example, SEQ ID NO:28 which can give rise to a L or a P being present at corresponding amino acid position 687 of, for example, SEQ ID NO:29.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach*, New,RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. application Ser. Nos. 60/111,701 and 60/056,713, both of which are herein incorporated by reference, for examples of such transducing sequences) to facilitate passage across cellular membranes if needed and can optionally be engineered to include nuclear localization sequences when desired.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that encodes the amino acid sequence shown in SEQ ID NO: 4.

2. An isolated nucleic acid molecule comprising a nucleotide sequence that encodes the amino acid sequence shown in SEQ ID NO: 2.

3. An expression vector comprising a nucleic acid sequence that encodes the amino acid sequence of SEQ ID NO:4.

4. A host cell comprising the expression vector of claim 3.

5. The isolated nucleic acid molecule of claim 1, wherein said nucleic acid molecule has the sequence of SEQ ID NO:3.

6. The isolated nucleic acid molecule of claim 2, wherein said nucleic acid molecule has the sequence of SEQ ID NO:1.

7. The expression vector or claim 3, wherein said nucleic acid sequence is that shown in SEQ ID NO:3.

8. The host cell of claim 4, wherein said expression vector comprises the nucleic acid sequence of SEQ ID NO:3.

9. An expression vector comprising a nucleic acid sequence that encodes the amino acid sequence of SEQ ID NO:2.

10. The expression vector of claim 9, wherein said nucleic acid sequence is that shown in SEQ ID NO:1.

11. A host cell comprising the expression vector of claim 9.

12. The host cell of claim 11, wherein the expression vector comprises the nucleic acid sequence of SEQ ID NO:1.

* * * * *

SEQUENCE LISTING

<160> NUMBER OF SEQ ID NOS: 50

<210> SEQ ID NO 1
<211> LENGTH: 3150
<212> TYPE: DNA

<213> ORGANISM: homo sapiens

<400> SEQUENCE: 1

| | | | | | |
|---|---|---|---|---|---|
| atgacggtgg | ttaatccaca | agacctgcag | ccgtgggtct | ctaacttcac | ctaccctgga | 60 |
| gcccgggatt | tctcccagct | ggctttggac | ccctccgggr | accagctcat | cgtgggagcc | 120 |
| aggaactacc | tcttcagact | cagccttgcc | aatgtctctc | ttcttcaggc | cacagagtgg | 180 |
| gcctccagtg | aggacacgcg | ccgctcctgc | caaagcaaag | ggaagactga | ggaggagtgt | 240 |
| cagaactacg | tgcgagtcct | gatcgtcgcc | ggccggaagt | tgttcatgtg | tggaaccaat | 300 |
| gccttttccc | ccatgtgcac | cagcagacag | gtggggaacc | tcagccggac | tattgagaag | 360 |
| atcaatggtg | tggcccgctg | cccctatgac | ccacgccaca | actccacagc | tgtcatctcc | 420 |
| tcccaggggg | agctctatgc | agccacggtc | atcgacttct | caggtcggga | ccctgccatc | 480 |
| taccgcagcc | tgggcagtgg | gccaccgctt | cgcactgccc | aatataactc | caagtggctt | 540 |
| aatgagccaa | acttcgtggc | agcctatgat | attgggctgt | ttgcatactt | cttcctgcgg | 600 |
| gagaacgcag | tggagcacga | ctgtggacgc | accgtgtact | ctcgcgtggc | ccgcgtgtgc | 660 |
| aagaatgacg | tgggggggccg | attcctgctg | gaggacacat | ggaccacatt | catgaaggcc | 720 |
| cggctcaact | gctcccgccc | gggcgaggtc | cccttctact | ataacgagct | gcagagtgcc | 780 |
| ttccacttgc | crgagcagga | cctcatctat | ggagttttca | caaccaacgt | aaacagcaty | 840 |
| gcggcttctg | ctgtctgcgc | cttcaacctc | agtgctatct | cccaggcttt | caatggccca | 900 |
| tttcgctacc | aggagaaccc | cagggctgcc | tggctcccca | tagccaaccc | catccccaat | 960 |
| ttccagtgtg | gcaccctgcc | tgagaccggt | cccaacgaga | acctgacgga | gcgcagcctg | 1020 |
| caggacgcgc | agcgcctctt | cctgatgagc | gaggccgtgc | agccggtgac | acccgagccc | 1080 |
| tgtgtcaccc | aggacagcgt | gcgcttctca | cacctcgtgg | tggacctggt | gcaggctaaa | 1140 |
| gacacgctct | accatgtact | ctacattggc | accgagtcgg | gcaccatcct | gaaggcgctg | 1200 |
| tccacggcga | gccgcagcct | ccacggctgc | tacctggagg | agctgcacgt | gctgcccccc | 1260 |
| gggcgccgcg | agccctgcg | cagcctgcgc | atcctgcaca | gcgcccgcgc | gctcttcgtg | 1320 |
| gggctgagag | acggcgtcct | gcgggtccca | ctggagaggt | gcgccgccta | ccgcagccag | 1380 |
| ggggcatgcc | tgggggcccg | ggacccgtac | tgtggctggg | acgggaagca | gcaacgttgc | 1440 |
| agcacactcg | aggacagctc | caacatgagc | ctctggaccc | agaacatcac | cgcctgtcct | 1500 |
| gtgcggaatg | tgcacgggga | tgggggcttc | ggcccatggt | caccatgcca | accatgtgag | 1560 |
| cacttggatg | gggacaactc | aggctcttgc | ctgtgtcgag | ctcgatcctg | tgattcccct | 1620 |
| cgaccccgct | gtgggggcct | tgactgcctg | gggccagcca | tccacatcgc | caactgctcc | 1680 |
| aggaatgggg | cgtggacccc | gtggtcatcg | tgggcgctgt | gcagcacgtc | ctgtggcatc | 1740 |
| ggcttccagg | tccgccagcg | aagttgcagc | aaccctgctc | cccgccacgg | gggccgcatc | 1800 |
| tgcgtgggca | agagccggga | ggaacggttc | tgtaatgaga | cacgccttg | cccggtgccc | 1860 |
| atcttctggg | cttcctgggg | ctcctggagc | aagtgcagca | gcaactgtgg | aggggcatg | 1920 |
| cagtcgcggc | gtcgggcctg | cgagaacggc | aactcctgcc | tgggctgcgg | cgtggagttc | 1980 |
| aagacgtgca | accccgaggg | ctgccccgaa | gtgcggcgca | acacccctg | gacgccgtgg | 2040 |
| ctgcccgtga | acgtgacgca | gggcgggca | cggcaggagc | agcggttccg | cttcacctgc | 2100 |
| cgcgcgcccc | ttgcagaccc | gcacggcctg | cagttcggca | ggagaaggac | cgagacgagg | 2160 |
| acctgtcccg | cggacggctc | cggctcctgc | gacaccgacg | ccctggtgga | ggacctcctg | 2220 |
| cgcagcggga | gcacctcccc | gcacacggtg | agcgggggct | gggccgcctg | ggcccgtgg | 2280 |

-continued

```
tcgtcctgct cccgggactg cgagctgggc ttccgcgtcc gcaagagaac gtgcactaac    2340
ccggagcccc gcaacggggg cctgccctgc gtgggcgatg ctgccgagta ccaggactgc    2400 aaccccccagg cttgcccagt tcgggtgct tggtcctgct ggacctcatg gtctccatgc    2460
tcagcttcct gtggtggggg tcactatcaa cgcacccgtt cctgcaccag ccccgcaccc    2520
tccccaggtg aggacatctg tctcgggctg cacacggagg aggcactatg tgccacacag    2580
gcctgcccag aaggctggtc gccctggtct gagtggagta agtgcactga cgacggagcc    2640
cagagccgaa gccggcactg tgaggagctc ctcccagggt ccagcgcctg tgctggaaac    2700
agcagccaga gccgcccctg ccctacagc gagattcccg tcatcctgcc agcctccagc    2760
atggaggagg ccaccggctg tgcagggttc aatctcatcc acttggtggc cacgggcatc    2820
tcctgcttct tgggctctgg gctcctgacc ctagcagtgt acctgtcttg ccagcactgc    2880
cagcgtcagt cccaggagtc cacactggtc catcctgcca ccccaacca tttgcactac    2940 aagggcggag gcaccccgaa gaatgaaaag tacacaccca tggaattcaa gaccctgaac    3000
aagaataact tgatccctga tgacagagcc aacttctacc cattgcagca gaccaatgtg    3060
tacacgacta cttactaccc aagcccctg aacaaacaca gcttccggcc cgaggcctca    3120
cctggacaac ggtgcttccc caacagctga                                      3150
```

<210> SEQ ID NO 2
<211> LENGTH: 1049
<212> TYPE: PRT
<213> ORGANISM: homo sapiens

<400> SEQUENCE: 2

```
Met Thr Val Val Asn Pro Gln Asp Leu Gln Pro Trp Val Ser Asn Phe
 1               5                  10                  15

Thr Tyr Pro Gly Ala Arg Asp Phe Ser Gln Leu Ala Leu Asp Pro Ser
            20                  25                  30

Gly Asn Gln Leu Ile Val Gly Ala Arg Asn Tyr Leu Phe Arg Leu Ser
        35                  40                  45

Leu Ala Asn Val Ser Leu Leu Gln Ala Thr Glu Trp Ala Ser Ser Glu
    50                  55                  60

Asp Thr Arg Arg Ser Cys Gln Ser Lys Gly Lys Thr Glu Glu Glu Cys
65                  70                  75                  80

Gln Asn Tyr Val Arg Val Leu Ile Val Ala Gly Arg Lys Val Phe Met
                85                  90                  95

Cys Gly Thr Asn Ala Phe Ser Pro Met Cys Thr Ser Arg Gln Val Gly
            100                 105                 110

Asn Leu Ser Arg Thr Ile Glu Lys Ile Asn Gly Val Ala Arg Cys Pro
        115                 120                 125

Tyr Asp Pro Arg His Asn Ser Thr Ala Val Ile Ser Ser Gln Gly Glu
    130                 135                 140

Leu Tyr Ala Ala Thr Val Ile Asp Phe Ser Gly Arg Asp Pro Ala Ile
145                 150                 155                 160

Tyr Arg Ser Leu Gly Ser Gly Pro Pro Leu Arg Thr Ala Gln Tyr Asn
                165                 170                 175

Ser Lys Trp Leu Asn Glu Pro Asn Phe Val Ala Ala Tyr Asp Ile Gly
            180                 185                 190

Leu Phe Ala Tyr Phe Phe Leu Arg Glu Asn Ala Val Glu His Asp Cys
        195                 200                 205

Gly Arg Thr Val Tyr Ser Arg Val Ala Arg Val Cys Lys Asn Asp Val
```

```
            210                 215                 220
Gly Gly Arg Phe Leu Leu Glu Asp Thr Trp Thr Thr Phe Met Lys Ala
225                 230                 235                 240

Arg Leu Asn Cys Ser Arg Pro Gly Glu Val Pro Phe Tyr Tyr Asn Glu
                245                 250                 255

Leu Gln Ser Ala Phe His Leu Pro Glu Gln Asp Leu Ile Tyr Gly Val
                260                 265                 270

Phe Thr Thr Asn Val Asn Ser Ile Ala Ala Ser Ala Val Cys Ala Phe
            275                 280                 285

Asn Leu Ser Ala Ile Ser Gln Ala Phe Asn Gly Pro Phe Arg Tyr Gln
            290                 295                 300

Glu Asn Pro Arg Ala Ala Trp Leu Pro Ile Ala Asn Pro Ile Pro Asn
305                 310                 315                 320

Phe Gln Cys Gly Thr Leu Pro Glu Thr Gly Pro Asn Glu Asn Leu Thr
                325                 330                 335

Glu Arg Ser Leu Gln Asp Ala Gln Arg Leu Phe Leu Met Ser Glu Ala
                340                 345                 350

Val Gln Pro Val Thr Pro Glu Pro Cys Val Thr Gln Asp Ser Val Arg
            355                 360                 365

Phe Ser His Leu Val Val Asp Leu Val Gln Ala Lys Asp Thr Leu Tyr
            370                 375                 380

His Val Leu Tyr Ile Gly Thr Glu Ser Gly Thr Ile Leu Lys Ala Leu
385                 390                 395                 400

Ser Thr Ala Ser Arg Ser Leu His Gly Cys Tyr Leu Glu Glu Leu His
                405                 410                 415

Val Leu Pro Pro Gly Arg Arg Glu Pro Leu Arg Ser Leu Arg Ile Leu
                420                 425                 430

His Ser Ala Arg Ala Leu Phe Val Gly Leu Arg Asp Gly Val Leu Arg
            435                 440                 445

Val Pro Leu Glu Arg Cys Ala Ala Tyr Arg Ser Gln Gly Ala Cys Leu
            450                 455                 460

Gly Ala Arg Asp Pro Tyr Cys Gly Trp Asp Gly Lys Gln Gln Arg Cys
465                 470                 475                 480

Ser Thr Leu Glu Asp Ser Ser Asn Met Ser Leu Trp Thr Gln Asn Ile
                485                 490                 495

Thr Ala Cys Pro Val Arg Asn Val Thr Arg Asp Gly Gly Phe Gly Pro
                500                 505                 510

Trp Ser Pro Trp Gln Pro Cys Glu His Leu Asp Gly Asp Asn Ser Gly
            515                 520                 525

Ser Cys Leu Cys Arg Ala Arg Ser Cys Asp Ser Pro Arg Pro Arg Cys
            530                 535                 540

Gly Gly Leu Asp Cys Leu Gly Pro Ala Ile His Ile Ala Asn Cys Ser
545                 550                 555                 560

Arg Asn Gly Ala Trp Thr Pro Trp Ser Ser Trp Ala Leu Cys Ser Thr
                565                 570                 575

Ser Cys Gly Ile Gly Phe Gln Val Arg Gln Arg Ser Cys Ser Asn Pro
            580                 585                 590

Ala Pro Arg His Gly Gly Arg Ile Cys Val Gly Lys Ser Arg Glu Glu
            595                 600                 605

Arg Phe Cys Asn Glu Asn Thr Pro Cys Pro Val Pro Ile Phe Trp Ala
            610                 615                 620

Ser Trp Gly Ser Trp Ser Lys Cys Ser Ser Asn Cys Gly Gly Gly Met
625                 630                 635                 640
```

```
Gln Ser Arg Arg Arg Ala Cys Glu Asn Gly Asn Ser Cys Leu Gly Cys
            645                 650                 655
Gly Val Glu Phe Lys Thr Cys Asn Pro Glu Gly Cys Pro Glu Val Arg
        660                 665                 670
Arg Asn Thr Pro Trp Thr Pro Trp Leu Pro Val Asn Val Thr Gln Gly
    675                 680                 685
Gly Ala Arg Gln Glu Gln Arg Phe Arg Phe Thr Cys Arg Ala Pro Leu
690                 695                 700
Ala Asp Pro His Gly Leu Gln Phe Gly Arg Arg Arg Thr Glu Thr Arg
705                 710                 715                 720
Thr Cys Pro Ala Asp Gly Ser Gly Ser Cys Asp Thr Asp Ala Leu Val
            725                 730                 735
Glu Asp Leu Leu Arg Ser Gly Ser Thr Ser Pro His Thr Val Ser Gly
        740                 745                 750
Gly Trp Ala Ala Trp Gly Pro Trp Ser Ser Cys Ser Arg Asp Cys Glu
    755                 760                 765
Leu Gly Phe Arg Val Arg Lys Arg Thr Cys Thr Asn Pro Glu Pro Arg
770                 775                 780
Asn Gly Gly Leu Pro Cys Val Gly Asp Ala Ala Glu Tyr Gln Asp Cys
785                 790                 795                 800
Asn Pro Gln Ala Cys Pro Val Arg Gly Ala Trp Ser Cys Trp Thr Ser
            805                 810                 815
Trp Ser Pro Cys Ser Ala Ser Cys Gly Gly Gly His Tyr Gln Arg Thr
        820                 825                 830
Arg Ser Cys Thr Ser Pro Ala Pro Ser Pro Gly Glu Asp Ile Cys Leu
    835                 840                 845
Gly Leu His Thr Glu Glu Ala Leu Cys Ala Thr Gln Ala Cys Pro Glu
850                 855                 860
Gly Trp Ser Pro Trp Ser Glu Trp Ser Lys Cys Thr Asp Asp Gly Ala
865                 870                 875                 880
Gln Ser Arg Ser Arg His Cys Glu Glu Leu Leu Pro Gly Ser Ser Ala
            885                 890                 895
Cys Ala Gly Asn Ser Ser Gln Ser Arg Pro Cys Pro Tyr Ser Glu Ile
        900                 905                 910
Pro Val Ile Leu Pro Ala Ser Ser Met Glu Glu Ala Thr Gly Cys Ala
    915                 920                 925
Gly Phe Asn Leu Ile His Leu Val Ala Thr Gly Ile Ser Cys Phe Leu
930                 935                 940
Gly Ser Gly Leu Leu Thr Leu Ala Val Tyr Leu Ser Cys Gln His Cys
945                 950                 955                 960
Gln Arg Gln Ser Gln Glu Ser Thr Leu Val His Pro Ala Thr Pro Asn
            965                 970                 975
His Leu His Tyr Lys Gly Gly Thr Pro Lys Asn Glu Lys Tyr Thr
        980                 985                 990
Pro Met Glu Phe Lys Thr Leu Asn Lys Asn Leu Ile Pro Asp Asp
    995                 1000                1005
Arg Ala Asn Phe Tyr Pro Leu Gln Gln Thr Asn Val Tyr Thr Thr Thr
    1010                1015                1020
Tyr Tyr Pro Ser Pro Leu Asn Lys His Ser Phe Arg Pro Glu Ala Ser
1025                1030                1035                1040
Pro Gly Gln Arg Cys Phe Pro Asn Ser
            1045
```

<210> SEQ ID NO 3
<211> LENGTH: 3282
<212> TYPE: DNA
<213> ORGANISM: homo sapiens

<400> SEQUENCE: 3

| | | | | | |
|---|---|---|---|---|---|
| atggtgcttg | caggcccct | ggctgtctcg | ctgttgctgc | ccagcctcac | actgctggtg | 60 |
| tcccacctct | ccagctccca | ggatgtctcc | agtgagccca | gcagtgagca | gcagctgtgc | 120 |
| gcccttagca | agcaccccac | cgtggccttt | gaagacctgc | agccgtgggt | ctctaacttc | 180 |
| acctaccctg | gagcccggga | tttctcccag | ctggctttgg | acccctccgg | graccagctc | 240 |
| atcgtgggag | ccaggaacta | cctcttcaga | ctcagccttg | ccaatgtctc | tcttcttcag | 300 |
| gccacagagt | gggcctccag | tgaggacacg | cgccgctcct | gccaaagcaa | agggaagact | 360 |
| gaggaggagt | gtcagaacta | cgtgcgagtc | ctgatcgtcg | ccggccggaa | ggtgttcatg | 420 |
| tgtggaacca | atgccttttc | ccccatgtgc | accagcagac | aggtggggaa | cctcagccgg | 480 |
| actattgaga | gatcaatgg | tgtggcccgc | tgcccctatg | acccacgcca | caactccaca | 540 |
| gctgtcatct | cctcccaggg | ggagctctat | gcagccacgg | tcatcgactt | ctcaggtcgg | 600 |
| gaccctgcca | tctaccgcag | cctgggcagt | gggccaccgc | ttcgcactgc | caatataac | 660 |
| tccaagtggc | ttaatgagcc | aaacttcgtg | gcagcctatg | atattgggct | gtttgcatac | 720 |
| ttcttcctgc | gggagaacgc | agtggagcac | gactgtggac | gcaccgtgta | ctctcgcgtg | 780 |
| gcccgcgtgt | gcaagaatga | cgtgggggc | cgattcctgc | tggaggacac | atggaccaca | 840 |
| ttcatgaagg | cccggctcaa | ctgctcccgc | ccgggcgagg | tcccttcta | ctataacgag | 900 |
| ctgcagagtg | ccttccactt | gccrgagcag | gacctcatct | atggagtttt | cacaaccaac | 960 |
| gtaaacagca | tygcggcttc | tgctgtctgc | gccttcaacc | tcagtgctat | ctcccaggct | 1020 |
| ttcaatggcc | catttcgcta | ccaggagaac | cccaggctg | cctggctccc | catagccaac | 1080 |
| cccatcccca | atttccagtg | tggcaccctg | cctgagaccg | tcccaacga | aacctgacg | 1140 |
| gagcgcagcc | tgcaggacgc | gcagcgcctc | ttcctgatga | gcgaggccgt | gcagccggtg | 1200 |
| acacccgagc | cctgtgtcac | ccaggacagc | gtgcgcttct | cacacctcgt | ggtggacctg | 1260 |
| gtgcaggcta | aagacacgct | ctaccatgta | ctctacattg | gcaccgagtc | gggcaccatc | 1320 |
| ctgaaggcgc | tgtccacggc | gagccgcagc | ctccacggct | gctacctgga | ggagctgcac | 1380 |
| gtgctgcccc | ccgggcgccg | cgagccctg | cgcagcctgc | gcatcctgca | cagcgcccgc | 1440 |
| gcgctcttcg | tggggctgag | agacggcgtc | ctgcgggtcc | cactggagag | gtgcgccgcc | 1500 |
| taccgcagcc | aggggcatg | cctggggcc | cgggaccgt | actgtggctg | ggacgggaag | 1560 |
| cagcaacgtt | gcagcacact | cgaggacagc | tccaacatga | gcctctggac | ccagaacatc | 1620 |
| accgcctgtc | ctgtgcggaa | tgtgacacgg | gatggggct | tcggcccatg | gtcaccatgg | 1680 |
| caaccatgtg | agcacttgga | tggggacaac | tcaggctctt | gcctgtgtcg | agctcgatcc | 1740 |
| tgtgattccc | ctcgacccg | ctgtggggc | cttgactgcc | tggggccagc | catccacatc | 1800 |
| gccaactgct | ccaggaatgg | ggcgtggacc | ccgtggtcat | cgtgggcgct | gtgcagcacg | 1860 |
| tcctgtggca | tcggcttcca | ggtccgccag | cgaagttgca | gcaaccctgc | tccccgccac | 1920 |
| ggggccgca | tctgcgtggg | caagagccgg | gaggaacggt | tctgtaatga | aacacgcct | 1980 |
| tgcccggtgc | ccatcttctg | ggcttcctgg | ggctcctgga | gcaagtgcag | cagcaactgt | 2040 |
| ggaggggca | tgcagtcgcg | gcgtcgggcc | tgcgagaacg | gcaactcctg | cctgggctgc | 2100 |
| ggcgtggagt | tcaagacgtg | caacccgag | ggctgccccg | aagtgcggcg | caacacccc | 2160 |

-continued

```
tggacgccgt ggctgcccgt gaacgtgacg cagggcgggg cacggcagga gcagcggttc    2220
cgcttcacct gccgcgcgcc ccttgcagac ccgcacggcc tgcagttcgg caggagaagg    2280
accgagacga ggacctgtcc cgcggacggc tccggctcct cgcacaccga cgccctggtg    2340
gaggacctcc tgcgcagcgg gagcacctcc ccgcacacgg tgagcggggg ctgggccgcc    2400
tggggcccgt ggtcgtcctg ctcccgggac tgcgagctgg gcttccgcgt ccgcaagaga    2460
acgtgcacta accggagcc ccgcaacggg ggcctgccct gcgtgggcga tgctgccgag    2520
taccaggact gcaacccca ggcttgccca gttcggggtg cttggtcctg ctggacctca    2580
tggtctccat gctcagcttc ctgtggtggg ggtcactatc aacgcacccg ttcctgcacc    2640
agccccgcac cctccccagg tgaggacatc tgtctcgggc tgcacacgga ggaggcacta    2700
tgtgccacac aggcctgccc agaaggctgg tcgccctggt ctgagtggag taagtgcact    2760
gacgacggag cccagagccg aagccggcac tgtgaggagc tcctcccagg gtccagcgcc    2820
tgtgctggaa acagcagcca gagccgcccc tgcccctaca gcgagattcc cgtcatcctg    2880
ccagcctcca gcatggagga ggccaccggc tgtgcagggt tcaatctcat ccacttggtg    2940
gccacgggca tctcctgctt cttgggctct gggctcctga ccctagcagt gtacctgtct    3000
tgccagcact gccagcgtca gtcccaggag tccacactgg tccatcctgc accccccaac    3060
catttgcact acaagggcgg aggcaccccg aagaatgaaa agtacacacc catggaattc    3120
aagaccctga acaagaataa cttgatccct gatgacagag ccaacttcta cccattgcag    3180
cagaccaatg tgtacacgac tacttactac ccaagccccc tgaacaaaca cagcttccgg    3240
cccgaggcct cacctggaca acggtgcttc cccaacagct ga                      3282
```

<210> SEQ ID NO 4
<211> LENGTH: 1093
<212> TYPE: PRT
<213> ORGANISM: homo sapiens

<400> SEQUENCE: 4

```
Met Val Leu Ala Gly Pro Leu Ala Val Ser Leu Leu Pro Ser Leu
 1               5                   10                  15

Thr Leu Val Ser His Leu Ser Ser Gln Asp Val Ser Ser Glu
            20                  25                  30

Pro Ser Ser Glu Gln Gln Leu Cys Ala Leu Ser Lys His Pro Thr Val
        35                  40                  45

Ala Phe Glu Asp Leu Gln Pro Trp Val Ser Asn Phe Thr Tyr Pro Gly
    50                  55                  60

Ala Arg Asp Phe Ser Gln Leu Ala Leu Asp Pro Ser Gly Asn Gln Leu
65                  70                  75                  80

Ile Val Gly Ala Arg Asn Tyr Leu Phe Arg Leu Ser Leu Ala Asn Val
                85                  90                  95

Ser Leu Leu Gln Ala Thr Glu Trp Ala Ser Ser Glu Asp Thr Arg Arg
            100                 105                 110

Ser Cys Gln Ser Lys Gly Lys Thr Glu Glu Glu Cys Gln Asn Tyr Val
        115                 120                 125

Arg Val Leu Ile Val Ala Gly Arg Lys Val Phe Met Cys Gly Thr Asn
    130                 135                 140

Ala Phe Ser Pro Met Cys Thr Ser Arg Gln Val Gly Asn Leu Ser Arg
145                 150                 155                 160

Thr Ile Glu Lys Ile Asn Gly Val Ala Arg Cys Pro Tyr Asp Pro Arg
                165                 170                 175
```

```
His Asn Ser Thr Ala Val Ile Ser Ser Gln Gly Glu Leu Tyr Ala Ala
            180                 185                 190

Thr Val Ile Asp Phe Ser Gly Arg Asp Pro Ala Ile Tyr Arg Ser Leu
        195                 200                 205

Gly Ser Gly Pro Pro Leu Arg Thr Ala Gln Tyr Asn Ser Lys Trp Leu
        210                 215                 220

Asn Glu Pro Asn Phe Val Ala Ala Tyr Asp Ile Gly Leu Phe Ala Tyr
225                 230                 235                 240

Phe Phe Leu Arg Glu Asn Ala Val Glu His Asp Cys Gly Arg Thr Val
            245                 250                 255

Tyr Ser Arg Val Ala Arg Val Cys Lys Asn Asp Val Gly Gly Arg Phe
            260                 265                 270

Leu Leu Glu Asp Thr Trp Thr Thr Phe Met Lys Ala Arg Leu Asn Cys
            275                 280                 285

Ser Arg Pro Gly Glu Val Pro Phe Tyr Tyr Asn Glu Leu Gln Ser Ala
            290                 295                 300

Phe His Leu Pro Glu Gln Asp Leu Ile Tyr Gly Val Phe Thr Thr Asn
305                 310                 315                 320

Val Asn Ser Ile Ala Ala Ser Ala Val Cys Ala Phe Asn Leu Ser Ala
            325                 330                 335

Ile Ser Gln Ala Phe Asn Gly Pro Phe Arg Tyr Gln Glu Asn Pro Arg
            340                 345                 350

Ala Ala Trp Leu Pro Ile Ala Asn Pro Ile Pro Asn Phe Gln Cys Gly
            355                 360                 365

Thr Leu Pro Glu Thr Gly Pro Asn Glu Asn Leu Thr Glu Arg Ser Leu
            370                 375                 380

Gln Asp Ala Gln Arg Leu Phe Leu Met Ser Glu Ala Val Gln Pro Val
385                 390                 395                 400

Thr Pro Glu Pro Cys Val Thr Gln Asp Ser Val Arg Phe Ser His Leu
            405                 410                 415

Val Val Asp Leu Val Gln Ala Lys Asp Thr Leu Tyr His Val Leu Tyr
            420                 425                 430

Ile Gly Thr Glu Ser Gly Thr Ile Leu Lys Ala Leu Ser Thr Ala Ser
            435                 440                 445

Arg Ser Leu His Gly Cys Tyr Leu Glu Glu Leu His Val Leu Pro Pro
            450                 455                 460

Gly Arg Arg Glu Pro Leu Arg Ser Leu Arg Ile Leu His Ser Ala Arg
465                 470                 475                 480

Ala Leu Phe Val Gly Leu Arg Asp Gly Val Leu Arg Val Pro Leu Glu
            485                 490                 495

Arg Cys Ala Ala Tyr Arg Ser Gln Gly Ala Cys Leu Gly Ala Arg Asp
            500                 505                 510

Pro Tyr Cys Gly Trp Asp Gly Lys Gln Gln Arg Cys Ser Thr Leu Glu
            515                 520                 525

Asp Ser Ser Asn Met Ser Leu Trp Thr Gln Asn Ile Thr Ala Cys Pro
            530                 535                 540

Val Arg Asn Val Thr Arg Asp Gly Gly Phe Gly Pro Trp Ser Pro Trp
545                 550                 555                 560

Gln Pro Cys Glu His Leu Asp Gly Asp Asn Ser Gly Ser Cys Leu Cys
            565                 570                 575

Arg Ala Arg Ser Cys Asp Ser Pro Arg Pro Arg Cys Gly Gly Leu Asp
            580                 585                 590
```

-continued

```
Cys Leu Gly Pro Ala Ile His Ile Ala Asn Cys Ser Arg Asn Gly Ala
            595                 600                 605

Trp Thr Pro Trp Ser Ser Trp Ala Leu Cys Ser Thr Ser Cys Gly Ile
            610                 615                 620

Gly Phe Gln Val Arg Gln Arg Ser Cys Ser Asn Pro Ala Pro Arg His
625                 630                 635                 640

Gly Gly Arg Ile Cys Val Gly Lys Ser Arg Glu Glu Arg Phe Cys Asn
            645                 650                 655

Glu Asn Thr Pro Cys Pro Val Pro Ile Phe Trp Ala Ser Trp Gly Ser
            660                 665                 670

Trp Ser Lys Cys Ser Ser Asn Cys Gly Gly Met Gln Ser Arg Arg
            675                 680                 685

Arg Ala Cys Glu Asn Gly Asn Ser Cys Leu Gly Cys Gly Val Glu Phe
            690                 695                 700

Lys Thr Cys Asn Pro Glu Gly Cys Pro Glu Val Arg Arg Asn Thr Pro
705                 710                 715                 720

Trp Thr Pro Trp Leu Pro Val Asn Val Thr Gln Gly Gly Ala Arg Gln
            725                 730                 735

Glu Gln Arg Phe Arg Phe Thr Cys Arg Ala Pro Leu Ala Asp Pro His
            740                 745                 750

Gly Leu Gln Phe Gly Arg Arg Thr Glu Thr Arg Thr Cys Pro Ala
            755                 760                 765

Asp Gly Ser Gly Ser Cys Asp Thr Asp Ala Leu Val Glu Asp Leu Leu
770                 775                 780

Arg Ser Gly Ser Thr Ser Pro His Thr Val Ser Gly Gly Trp Ala Ala
785                 790                 795                 800

Trp Gly Pro Trp Ser Ser Cys Ser Arg Asp Cys Glu Leu Gly Phe Arg
            805                 810                 815

Val Arg Lys Arg Thr Cys Thr Asn Pro Glu Pro Arg Asn Gly Gly Leu
            820                 825                 830

Pro Cys Val Gly Asp Ala Ala Glu Tyr Gln Asp Cys Asn Pro Gln Ala
            835                 840                 845

Cys Pro Val Arg Gly Ala Trp Ser Cys Trp Thr Ser Trp Ser Pro Cys
            850                 855                 860

Ser Ala Ser Cys Gly Gly Gly His Tyr Gln Arg Thr Arg Ser Cys Thr
865                 870                 875                 880

Ser Pro Ala Pro Ser Pro Gly Glu Asp Ile Cys Leu Gly Leu His Thr
            885                 890                 895

Glu Glu Ala Leu Cys Ala Thr Gln Ala Cys Pro Glu Gly Trp Ser Pro
            900                 905                 910

Trp Ser Glu Trp Ser Lys Cys Thr Asp Asp Gly Ala Gln Ser Arg Ser
            915                 920                 925

Arg His Cys Glu Glu Leu Leu Pro Gly Ser Ser Ala Cys Ala Gly Asn
            930                 935                 940

Ser Ser Gln Ser Arg Pro Cys Pro Tyr Ser Glu Ile Pro Val Ile Leu
945                 950                 955                 960

Pro Ala Ser Ser Met Glu Glu Ala Thr Gly Cys Ala Gly Phe Asn Leu
            965                 970                 975

Ile His Leu Val Ala Thr Gly Ile Ser Cys Phe Leu Gly Ser Gly Leu
            980                 985                 990

Leu Thr Leu Ala Val Tyr Leu Ser Cys Gln His Cys Gln Arg Gln Ser
            995                 1000                1005

Gln Glu Ser Thr Leu Val His Pro Ala Thr Pro Asn His Leu His Tyr
```

```
                    1010                    1015                    1020
Lys Gly Gly Gly Thr Pro Lys Asn Glu Lys Tyr Thr Pro Met Glu Phe
1025                    1030                    1035                    1040

Lys Thr Leu Asn Lys Asn Asn Leu Ile Pro Asp Asp Arg Ala Asn Phe
                    1045                    1050                    1055

Tyr Pro Leu Gln Gln Thr Asn Val Tyr Thr Thr Thr Tyr Tyr Pro Ser
                    1060                    1065                    1070

Pro Leu Asn Lys His Ser Phe Arg Pro Glu Ala Ser Pro Gly Gln Arg
            1075                    1080                    1085

Cys Phe Pro Asn Ser
        1090

<210> SEQ ID NO 5
<211> LENGTH: 3105
<212> TYPE: DNA
<213> ORGANISM: homo sapiens

<400> SEQUENCE: 5
atgacggtgg ttaatccaca agacctgcag ccgtgggtct ctaacttcac ctaccctgga      60
gcccgggatt tctcccagct ggctttggac ccctccgggr accagctcat cgtgggagcc     120
aggaactacc tcttcagact cagccttgcc aatgtctctc ttcttcaggc cacagagtgg     180
gcctccagtg aggacacgcg ccgctcctgc aaaagcaaag gaagactga ggaggagtgt      240 cagaactacg tgcgagtcct gatcgtcgcc ggccggaagt tgttcatgtg tggaaccaat     300
gccttttccc ccatgtgcac cagcagacag gtggggaacc tcagccggac tattgagaag     360
atcaatggtg tggcccgctg ccctatgac ccacgccaca actccacagc tgtcatctcc      420
tcccaggggg agctctatgc agccacggtc atcgacttct caggtcggga ccctgccatc     480
taccgcagcc tgggcagtgg gccaccgctt cgcactgccc aatataactc caagtggctt     540
aatgagccaa acttcgtggc agcctatgat attgggctgt ttgcatactt cttcctgcgg     600
gagaacgcag tggagcacga ctgtggacgc accgtgtact ctcgcgtggc ccgcgtgtgc     660
aagaatgacg tgggggggccg attcctgctg gaggacacat ggaccacatt catgaaggcc     720
cggctcaact gctcccgccc gggcgaggtc cccttctact ataacgagct gcagagtgcc     780
ttccacttgc crgagcagga cctcatctat ggagttttca caaccaacgt aaacagcaty     840
gcggcttctg ctgtctgcgc cttcaacctc agtgctatct cccaggcttt caatggccca     900
tttcgctacc aggagaaccc cagggctgcc tggctcccca tagccaaccc catccccaat     960
ttccagtgtg gcaccctgcc tgagaccggt cccaacgaga acctgacgga gcgcagcctg    1020
caggacgcgc agcgcctctt cctgatgagc gaggccgtgc agccggtgac acccgagccc    1080
tgtgtcaccc aggacagcgt gcgcttctca cacctcgtgg tggacctggt gcaggctaaa    1140
gacacgctct accatgtact ctacattggc accgagtcgg gcaccatcct gaaggcgctg    1200
tccacggcga gccgcagcct ccacggctgc tacctggagg agctgcacgt gctgcccccc    1260
gggcgccgcg agccctgcgc agcctgcgcg atcctgcaca cgcccgcgc gctcttcgtg    1320 gggctgagag acggcgtcct gcgggtccca ctggagaggt gcgccgccta ccgcagccag    1380
ggggcatgcc tggggcccg ggacccgtac tgtggctggg acgggaagca gcaacgttgc    1440
agcacactcg aggacagctc caacatgagc ctctggaccc agaacatcac cgcctgtcct    1500
gtgcggaatg tgcacggga tgggggcttc ggccatggt caccatggca accatgtgag    1560
cacttggatg gggacaactc aggctcttgc ctgtgtcgag ctcgatcctg tgattcccct    1620
```

-continued

```
cgacccgct gtggggcct tgactgcctg gggccagcca tccacatcgc caactgctcc      1680
aggaatgggg cgtggacccc gtggtcatcg tgggcgctgt gcagcacgtc ctgtggcatc      1740
ggcttccagg tccgccagcg aagttgcagc aaccctgctc cccgccacgg gggccgcatc      1800
tgcgtgggca agagccggga ggaacggttc tgtaatgaga cacgccttg cccggtgccc      1860 atcttctggg cttcctgggg ctcctggagc aagtgcagca gcaactgtgg aggggcatg      1920 cagtcgcggc gtcgggcctg cgagaacggc aactcctgcc tgggctgcgg cgtggagttc      1980
aagacgtgca ccccgaggg ctgccccgaa gtgcggcgca caccccctg gacgccgtgg      2040 ctgcccgtga acgtgacgca gggcggggca cggcaggagc agcggttccg cttcacctgc      2100
cgcgcgcccc ttgcagaccc gcacggcctg cagttcggca ggagaaggac cgagacgagg      2160
acctgtcccg cggacggctc cggctcctgc gacaccgacg ccctggtgga ggacctcctg      2220
cgcagcggga gcacctcccc gcacacggtg agcgggggct gggccgcctg gggcccgtgg      2280
tcgtcctgct cccgggactg cgagctgggc ttccgcgtcc gcaagagaac gtgcactaac      2340
ccggagcccc gcaacggggg cctgcccctgc gtgggcgatg ctgccgagta ccaggactgc      2400 aaccccagg cttgcccagt tcgggggtgct tggtcctgct ggacctcatg gtctccatgc      2460
tcagcttcct gtggtggggg tcactatcaa cgcacccgtt cctgcaccag ccccgcaccc      2520
tccccaggtg aggacatctg tctcgggctg cacacgagg aggcactatg tgccacacag      2580
gcctgcccag aaggctggtc gccctggtct gagtggagta agtgcactga cgacggagcc      2640
cagagccgaa gccggcactg tgaggagctc ctcccagggt ccagcgcctg tgctggaaac      2700
agcagccaga gccgcccctg cccctacagc gagattcccg ggttcaatct catccacttg      2760
gtggccacgg gcatcctg cttcttgggc tctgggctcc tgaccctagc agtgtacctg      2820
tcttgccagc actgccagcg tcagtcccag gagtccacac tggtccatcc tgccaccccc      2880 aaccattgc actacaaggg cggaggcacc ccgaagaatg aaaagtacac acccatggaa      2940
ttcaagaccc tgaacaagaa taacttgatc cctgatgaca gagccaactt ctacccattg      3000
cagcagacca atgtgtacac gactacttac tacccaagcc ccctgaacaa acacagcttc      3060
cggcccgagg cctcacctgg acaacggtgc ttccccaaca gctga                      3105
```

<210> SEQ ID NO 6
<211> LENGTH: 1034
<212> TYPE: PRT
<213> ORGANISM: homo sapiens

<400> SEQUENCE: 6

Met Thr Val Val Asn Pro Gln Asp Leu Gln Pro Trp Val Ser Asn Phe
1               5                   10                  15

Thr Tyr Pro Gly Ala Arg Asp Phe Ser Gln Leu Ala Leu Asp Pro Ser
            20                  25                  30

Gly Asn Gln Leu Ile Val Gly Ala Arg Asn Tyr Leu Phe Arg Leu Ser
        35                  40                  45

Leu Ala Asn Val Ser Leu Leu Gln Ala Thr Glu Trp Ala Ser Ser Glu
    50                  55                  60

Asp Thr Arg Arg Ser Cys Gln Ser Lys Gly Lys Thr Glu Glu Glu Cys
65                  70                  75                  80

Gln Asn Tyr Val Arg Val Leu Ile Val Ala Gly Arg Lys Val Phe Met
                85                  90                  95

Cys Gly Thr Asn Ala Phe Ser Pro Met Cys Thr Ser Arg Gln Val Gly
            100                 105                 110

-continued

```
Asn Leu Ser Arg Thr Ile Glu Lys Ile Asn Gly Val Ala Arg Cys Pro
            115                 120                 125

Tyr Asp Pro Arg His Asn Ser Thr Ala Val Ile Ser Ser Gln Gly Glu
        130                 135                 140

Leu Tyr Ala Ala Thr Val Ile Asp Phe Ser Gly Arg Asp Pro Ala Ile
145                 150                 155                 160

Tyr Arg Ser Leu Gly Ser Gly Pro Pro Leu Arg Thr Ala Gln Tyr Asn
                165                 170                 175

Ser Lys Trp Leu Asn Glu Pro Asn Phe Val Ala Ala Tyr Asp Ile Gly
                    180                 185                 190

Leu Phe Ala Tyr Phe Phe Leu Arg Glu Asn Ala Val Glu His Asp Cys
            195                 200                 205

Gly Arg Thr Val Tyr Ser Arg Val Ala Arg Val Cys Lys Asn Asp Val
        210                 215                 220

Gly Gly Arg Phe Leu Leu Glu Asp Thr Trp Thr Thr Phe Met Lys Ala
225                 230                 235                 240

Arg Leu Asn Cys Ser Arg Pro Gly Glu Val Pro Phe Tyr Tyr Asn Glu
                245                 250                 255

Leu Gln Ser Ala Phe His Leu Pro Glu Gln Asp Leu Ile Tyr Gly Val
                    260                 265                 270

Phe Thr Thr Asn Val Asn Ser Ile Ala Ala Ser Ala Val Cys Ala Phe
            275                 280                 285

Asn Leu Ser Ala Ile Ser Gln Ala Phe Asn Gly Pro Phe Arg Tyr Gln
        290                 295                 300

Glu Asn Pro Arg Ala Ala Trp Leu Pro Ile Ala Asn Pro Ile Pro Asn
305                 310                 315                 320

Phe Gln Cys Gly Thr Leu Pro Glu Thr Gly Pro Asn Glu Asn Leu Thr
                325                 330                 335

Glu Arg Ser Leu Gln Asp Ala Gln Arg Leu Phe Leu Met Ser Glu Ala
                    340                 345                 350

Val Gln Pro Val Thr Pro Glu Pro Cys Val Thr Gln Asp Ser Val Arg
            355                 360                 365

Phe Ser His Leu Val Val Asp Leu Val Gln Ala Lys Asp Thr Leu Tyr
        370                 375                 380

His Val Leu Tyr Ile Gly Thr Glu Ser Gly Thr Ile Leu Lys Ala Leu
385                 390                 395                 400

Ser Thr Ala Ser Arg Ser Leu His Gly Cys Tyr Leu Glu Glu Leu His
                405                 410                 415

Val Leu Pro Pro Gly Arg Arg Glu Pro Leu Arg Ser Leu Arg Ile Leu
                    420                 425                 430

His Ser Ala Arg Ala Leu Phe Val Gly Leu Arg Asp Gly Val Leu Arg
            435                 440                 445

Val Pro Leu Glu Arg Cys Ala Ala Tyr Arg Ser Gln Gly Ala Cys Leu
        450                 455                 460

Gly Ala Arg Asp Pro Tyr Cys Gly Trp Asp Gly Lys Gln Gln Arg Cys
465                 470                 475                 480

Ser Thr Leu Glu Asp Ser Ser Asn Met Ser Leu Trp Thr Gln Asn Ile
                485                 490                 495

Thr Ala Cys Pro Val Arg Asn Val Thr Arg Asp Gly Gly Phe Gly Pro
                    500                 505                 510

Trp Ser Pro Trp Gln Pro Cys Glu His Leu Asp Gly Asp Asn Ser Gly
            515                 520                 525

Ser Cys Leu Cys Arg Ala Arg Ser Cys Asp Ser Pro Arg Pro Arg Cys
```

-continued

```
            530                 535                 540
Gly Gly Leu Asp Cys Leu Gly Pro Ala Ile His Ile Ala Asn Cys Ser
545                 550                 555                 560

Arg Asn Gly Ala Trp Thr Pro Trp Ser Ser Trp Ala Leu Cys Ser Thr
                565                 570                 575

Ser Cys Gly Ile Gly Phe Gln Val Arg Gln Arg Ser Cys Ser Asn Pro
            580                 585                 590

Ala Pro Arg His Gly Gly Arg Ile Cys Val Gly Lys Ser Arg Glu Glu
            595                 600                 605

Arg Phe Cys Asn Glu Asn Thr Pro Cys Pro Val Pro Ile Phe Trp Ala
            610                 615                 620

Ser Trp Gly Ser Trp Ser Lys Cys Ser Ser Asn Cys Gly Gly Gly Met
625                 630                 635                 640

Gln Ser Arg Arg Arg Ala Cys Glu Asn Gly Asn Ser Cys Leu Gly Cys
                645                 650                 655

Gly Val Glu Phe Lys Thr Cys Asn Pro Glu Gly Cys Pro Glu Val Arg
            660                 665                 670

Arg Asn Thr Pro Trp Thr Pro Trp Leu Pro Val Asn Val Thr Gln Gly
            675                 680                 685

Gly Ala Arg Gln Glu Gln Arg Phe Arg Phe Thr Cys Arg Ala Pro Leu
            690                 695                 700

Ala Asp Pro His Gly Leu Gln Phe Gly Arg Arg Arg Thr Glu Thr Arg
705                 710                 715                 720

Thr Cys Pro Ala Asp Gly Ser Gly Ser Cys Asp Thr Asp Ala Leu Val
                725                 730                 735

Glu Asp Leu Leu Arg Ser Gly Ser Thr Ser Pro His Thr Val Ser Gly
            740                 745                 750

Gly Trp Ala Ala Trp Gly Pro Trp Ser Ser Cys Ser Arg Asp Cys Glu
            755                 760                 765

Leu Gly Phe Arg Val Arg Lys Arg Thr Cys Thr Asn Pro Glu Pro Arg
770                 775                 780

Asn Gly Gly Leu Pro Cys Val Gly Asp Ala Ala Glu Tyr Gln Asp Cys
785                 790                 795                 800

Asn Pro Gln Ala Cys Pro Val Arg Gly Ala Trp Ser Cys Trp Thr Ser
                805                 810                 815

Trp Ser Pro Cys Ser Ala Ser Cys Gly Gly Gly His Tyr Gln Arg Thr
            820                 825                 830

Arg Ser Cys Thr Ser Pro Ala Pro Ser Pro Gly Glu Asp Ile Cys Leu
            835                 840                 845

Gly Leu His Thr Glu Glu Ala Leu Cys Ala Thr Gln Ala Cys Pro Glu
            850                 855                 860

Gly Trp Ser Pro Trp Ser Glu Trp Ser Lys Cys Thr Asp Asp Gly Ala
865                 870                 875                 880

Gln Ser Arg Ser Arg His Cys Glu Glu Leu Leu Pro Gly Ser Ser Ala
                885                 890                 895

Cys Ala Gly Asn Ser Ser Gln Ser Arg Pro Cys Pro Tyr Ser Glu Ile
            900                 905                 910

Pro Gly Phe Asn Leu Ile His Leu Val Ala Thr Gly Ile Ser Cys Phe
            915                 920                 925

Leu Gly Ser Gly Leu Leu Thr Leu Ala Val Tyr Leu Ser Cys Gln His
            930                 935                 940

Cys Gln Arg Gln Ser Gln Glu Ser Thr Leu Val His Pro Ala Thr Pro
945                 950                 955                 960
```

Asn His Leu His Tyr Lys Gly Gly Gly Thr Pro Lys Asn Glu Lys Tyr
          965                 970                 975

Thr Pro Met Glu Phe Lys Thr Leu Asn Lys Asn Asn Leu Ile Pro Asp
        980                 985                 990

Asp Arg Ala Asn Phe Tyr Pro Leu Gln Gln Thr Asn Val Tyr Thr Thr
        995                 1000                1005

Thr Tyr Tyr Pro Ser Pro Leu Asn Lys His Ser Phe Arg Pro Glu Ala
    1010                1015                1020

Ser Pro Gly Gln Arg Cys Phe Pro Asn Ser
1025                1030

<210> SEQ ID NO 7
<211> LENGTH: 3237
<212> TYPE: DNA
<213> ORGANISM: homo sapiens

<400> SEQUENCE: 7

| | | | | | |
|---|---|---|---|---|---|
| atggtgcttg | caggccccct | ggctgtctcg | ctgttgctgc | ccagcctcac | actgctggtg | 60 |
| tcccacctct | ccagctccca | ggatgtctcc | agtgagccca | gcagtgagca | gcagctgtgc | 120 |
| gcccttagca | agcaccccac | cgtggccttt | gaagacctgc | agccgtgggt | ctctaacttc | 180 |
| acctaccctg | gagcccggga | tttctcccag | ctggctttgg | accctccgg | graccagctc | 240 |
| atcgtgggag | ccaggaacta | cctcttcaga | ctcagccttg | ccaatgtctc | tcttcttcag | 300 |
| gccacagagt | gggcctccag | tgaggacacg | cgccgctcct | gccaaagcaa | aggaagact | 360 |
| gaggaggagt | gtcagaacta | cgtgcgagtc | ctgatcgtcg | ccggccggaa | ggtgttcatg | 420 |
| tgtggaacca | atgccttttc | ccccatgtgc | accagcagac | aggtggggaa | cctcagccgg | 480 |
| actattgaga | agatcaatgg | tgtggcccgc | tgcccctatg | acccacgcca | caactccaca | 540 |
| gctgtcatct | cctcccaggg | ggagctctat | gcagccacgg | tcatcgactt | ctcaggtcgg | 600 |
| gaccctgcca | tctaccgcag | cctgggcagt | gggccaccgc | ttcgcactgc | caatataac | 660 |
| tccaagtggc | ttaatgagcc | aaacttcgtg | gcagcctatg | atattgggct | gtttgcatac | 720 |
| ttcttcctgc | gggagaacgc | agtggagcac | actgtggac | gcaccgtgta | ctctcgcgtg | 780 |
| gcccgcgtgt | gcaagaatga | cgtggggggc | cgattcctgc | tggaggacac | atggaccaca | 840 |
| ttcatgaagg | cccggctcaa | ctgctcccgc | ccgggcgagg | tccccttcta | ctataacgag | 900 |
| ctgcagagtg | cctccacttt | gccrgagcag | gacctcatct | atggagttttt | cacaaccaac | 960 |
| gtaaacagca | tygcggcttc | tgctgtctgc | gccttcaacc | tcagtgctat | ctcccaggct | 1020 |
| ttcaatggcc | catttcgcta | ccaggagaac | cccaggggctg | cctggctccc | catagccaac | 1080 |
| cccatcccca | atttccagtg | tggcacctg | cctgagaccg | gtcccaacga | gaacctgacg | 1140 |
| gagcgcagcc | tgcaggacgc | gcagcgcctc | ttcctgatga | cgaggccgt | gcagccggtg | 1200 |
| acacccgagc | cctgtgtcac | ccaggacagc | gtgcgcttct | cacacctcgt | ggtggacctg | 1260 |
| gtgcaggcta | agacacgct | ctaccatgta | ctctacattg | gcaccgagtc | gggcaccatc | 1320 |
| ctgaaggcgc | tgtccacggc | gagccgcagc | ctccacggct | gctacctgga | ggagctgcac | 1380 |
| gtgctgcccc | ccgggcgccg | cgagcccctg | cgcagcctgc | gcatcctgca | cagcgcccgc | 1440 |
| gcgctcttcg | tggggctgag | agacggcgtc | ctgcgggtcc | cactggagag | gtgcgccgcc | 1500 |
| taccgcagcc | aggggcatg | cctgggggcc | cgggacccgt | actgtggctg | gacgggaag | 1560 |
| cagcaacgtt | gcagcacact | cgaggacagc | tccaacatga | gcctctggac | ccagaacatc | 1620 |
| accgcctgtc | ctgtgcggaa | tgtgacacgg | gatgggggct | tcggcccatg | gtcaccatgg | 1680 |

-continued

```
caaccatgtg agcacttgga tggggacaac tcaggctctt gcctgtgtcg agctcgatcc      1740
tgtgattccc ctcgaccccg ctgtgggggc cttgactgcc tggggccagc catccacatc      1800
gccaactgct ccaggaatgg ggcgtggacc ccgtggtcat cgtgggcgct gtgcagcacg      1860
tcctgtggca tcggcttcca ggtccgccag cgaagttgca gcaaccctgc tccccgccac      1920
gggggccgca tctgcgtggg caagagccgg gaggaacggt tctgtaatga aacacgcct       1980
tgcccggtgc ccatcttctg ggcttcctgg ggctcctgga gcaagtgcag cagcaactgt      2040
ggaggggca tgcagtcgcg cgtcgggcc tgcgagaacg caactcctg cctgggctgc         2100
ggcgtggagt tcaagacgtg caaccccgag ggctgccccg aagtgcggcg caacaccccc      2160
tggacgccgt ggctgcccgt gaacgtgacg cagggcgggg cacggcagga gcagcggttc      2220
cgcttcacct gccgcgcgcc ccttgcagac ccgcacggcc tgcagttcgg caggagaagg      2280
accgagacga ggacctgtcc cgcggacggc tccggctcct cgacaccga cgccctggtg       2340
gaggacctcc tgcgcagcgg gagcacctcc ccgcacacgg tgagcggggg ctgggccgcc      2400
tggggccgt ggtcgtcctg ctcccgggac tgcgagctgg gcttccgcgt ccgcaagaga       2460
acgtgcacta acccggagcc ccgcaacggg ggcctgccct gcgtgggcga tgctgccgag      2520
taccaggact gcaaccccca ggcttgccca gttcggggtg cttggtcctg ctggacctca      2580
tggtctccat gctcagcttc ctgtggtggg ggtcactatc aacgcacccg ttcctgcacc      2640
agccccgcac cctccccagg tgaggacatc tgtctcgggc tgcacacgga ggaggcacta     2700
tgtgccacac aggcctgccc agaaggctgg tcgccctggt ctgagtggag taagtgcact      2760
gacgacggag cccagagccg aagccggcac tgtgaggagc tcctcccagg gtccagcgcc      2820
tgtgctggaa acagcagcca gagccgcccc tgcccctaca gcagagattcc cgggttcaat    2880
ctcatccact tggtggccac gggcatctcc tgcttcttgg gctctgggct cctgacccta     2940
gcagtgtacc tgtcttgcca gcactgccag cgtcagtccc aggagtccac actggtccat     3000
cctgccaccc ccaaccattt gcactacaag ggcggaggca ccccgaagaa tgaaaagtac     3060
acacccatgg aattcaagac cctgaacaag aataacttga tccctgatga cagagccaac     3120
ttctacccat tgcagcagac caatgtgtac acgactactt actacccaag ccccctgaac    3180
aaacacagct tccggcccga ggcctcacct ggacaacggt gcttccccaa cagctga        3237
```

<210> SEQ ID NO 8
<211> LENGTH: 1078
<212> TYPE: PRT
<213> ORGANISM: homo sapiens

<400> SEQUENCE: 8

```
Met Val Leu Ala Gly Pro Leu Ala Val Ser Leu Leu Pro Ser Leu
 1               5                  10                  15

Thr Leu Leu Val Ser His Leu Ser Ser Ser Gln Asp Val Ser Ser Glu
                20                  25                  30

Pro Ser Ser Glu Gln Gln Leu Cys Ala Leu Ser Lys His Pro Thr Val
            35                  40                  45

Ala Phe Glu Asp Leu Gln Pro Trp Val Ser Asn Phe Thr Tyr Pro Gly
        50                  55                  60

Ala Arg Asp Phe Ser Gln Leu Ala Leu Asp Pro Ser Gly Asn Gln Leu
65                  70                  75                  80

Ile Val Gly Ala Arg Asn Tyr Leu Phe Arg Leu Ser Leu Ala Asn Val
                85                  90                  95
```

-continued

```
Ser Leu Leu Gln Ala Thr Glu Trp Ala Ser Ser Glu Asp Thr Arg Arg
            100                 105                 110
Ser Cys Gln Ser Lys Gly Lys Thr Glu Glu Cys Gln Asn Tyr Val
        115                 120                 125
Arg Val Leu Ile Val Ala Gly Arg Lys Val Phe Met Cys Gly Thr Asn
        130                 135                 140
Ala Phe Ser Pro Met Cys Thr Ser Arg Gln Val Gly Asn Leu Ser Arg
145                 150                 155                 160
Thr Ile Glu Lys Ile Asn Gly Val Ala Arg Cys Pro Tyr Asp Pro Arg
                165                 170                 175
His Asn Ser Thr Ala Val Ile Ser Ser Gln Gly Glu Leu Tyr Ala Ala
            180                 185                 190
Thr Val Ile Asp Phe Ser Gly Arg Asp Pro Ala Ile Tyr Arg Ser Leu
        195                 200                 205
Gly Ser Gly Pro Pro Leu Arg Thr Ala Gln Tyr Asn Ser Lys Trp Leu
    210                 215                 220
Asn Glu Pro Asn Phe Val Ala Ala Tyr Asp Ile Gly Leu Phe Ala Tyr
225                 230                 235                 240
Phe Phe Leu Arg Glu Asn Ala Val Glu His Asp Cys Gly Arg Thr Val
                245                 250                 255
Tyr Ser Arg Val Ala Arg Val Cys Lys Asn Asp Val Gly Gly Arg Phe
            260                 265                 270
Leu Leu Glu Asp Thr Trp Thr Thr Phe Met Lys Ala Arg Leu Asn Cys
        275                 280                 285
Ser Arg Pro Gly Glu Val Pro Phe Tyr Tyr Asn Glu Leu Gln Ser Ala
    290                 295                 300
Phe His Leu Pro Glu Gln Asp Leu Ile Tyr Gly Val Phe Thr Thr Asn
305                 310                 315                 320
Val Asn Ser Ile Ala Ala Ser Ala Val Cys Ala Phe Asn Leu Ser Ala
                325                 330                 335
Ile Ser Gln Ala Phe Asn Gly Pro Phe Arg Tyr Gln Glu Asn Pro Arg
            340                 345                 350
Ala Ala Trp Leu Pro Ile Ala Asn Pro Ile Pro Asn Phe Gln Cys Gly
        355                 360                 365
Thr Leu Pro Glu Thr Gly Pro Asn Glu Asn Leu Thr Glu Arg Ser Leu
    370                 375                 380
Gln Asp Ala Gln Arg Leu Phe Leu Met Ser Glu Ala Val Gln Pro Val
385                 390                 395                 400
Thr Pro Glu Pro Cys Val Thr Gln Asp Ser Val Arg Phe Ser His Leu
                405                 410                 415
Val Val Asp Leu Val Gln Ala Lys Asp Thr Leu Tyr His Val Leu Tyr
            420                 425                 430
Ile Gly Thr Glu Ser Gly Thr Ile Leu Lys Ala Leu Ser Thr Ala Ser
        435                 440                 445
Arg Ser Leu His Gly Cys Tyr Leu Glu Glu Leu His Val Leu Pro Pro
    450                 455                 460
Gly Arg Arg Glu Pro Leu Arg Ser Leu Arg Ile Leu His Ser Ala Arg
465                 470                 475                 480
Ala Leu Phe Val Gly Leu Arg Asp Gly Val Leu Arg Val Pro Leu Glu
                485                 490                 495
Arg Cys Ala Ala Tyr Arg Ser Gln Gly Ala Cys Leu Gly Ala Arg Asp
            500                 505                 510
Pro Tyr Cys Gly Trp Asp Gly Lys Gln Gln Arg Cys Ser Thr Leu Glu
```

-continued

```
                515                 520                 525

Asp Ser Ser Asn Met Ser Leu Trp Thr Gln Asn Ile Thr Ala Cys Pro
            530                 535                 540

Val Arg Asn Val Thr Arg Asp Gly Gly Phe Gly Pro Trp Ser Pro Trp
545                 550                 555                 560

Gln Pro Cys Glu His Leu Asp Gly Asp Asn Ser Gly Ser Cys Leu Cys
                565                 570                 575

Arg Ala Arg Ser Cys Asp Ser Pro Arg Pro Arg Cys Gly Gly Leu Asp
            580                 585                 590

Cys Leu Gly Pro Ala Ile His Ile Ala Asn Cys Ser Arg Asn Gly Ala
            595                 600                 605

Trp Thr Pro Trp Ser Ser Trp Ala Leu Cys Ser Thr Ser Cys Gly Ile
    610                 615                 620

Gly Phe Gln Val Arg Gln Arg Ser Cys Ser Asn Pro Ala Pro Arg His
625                 630                 635                 640

Gly Gly Arg Ile Cys Val Gly Lys Ser Arg Glu Arg Phe Cys Asn
                645                 650                 655

Glu Asn Thr Pro Cys Pro Val Pro Ile Phe Trp Ala Ser Trp Gly Ser
                660                 665                 670

Trp Ser Lys Cys Ser Ser Asn Cys Gly Gly Met Gln Ser Arg Arg
    675                 680                 685

Arg Ala Cys Glu Asn Gly Asn Ser Cys Leu Gly Cys Gly Val Glu Phe
            690                 695                 700

Lys Thr Cys Asn Pro Glu Gly Cys Pro Glu Val Arg Arg Asn Thr Pro
705                 710                 715                 720

Trp Thr Pro Trp Leu Pro Val Asn Val Thr Gln Gly Gly Ala Arg Gln
                725                 730                 735

Glu Gln Arg Phe Arg Phe Thr Cys Arg Ala Pro Leu Ala Asp Pro His
            740                 745                 750

Gly Leu Gln Phe Gly Arg Arg Thr Glu Thr Arg Thr Cys Pro Ala
    755                 760                 765

Asp Gly Ser Gly Ser Cys Asp Thr Ala Leu Val Glu Asp Leu Leu
    770                 775                 780

Arg Ser Gly Ser Thr Ser Pro His Thr Val Ser Gly Gly Trp Ala Ala
785                 790                 795                 800

Trp Gly Pro Trp Ser Ser Cys Ser Arg Asp Cys Glu Leu Gly Phe Arg
                805                 810                 815

Val Arg Lys Arg Thr Cys Thr Asn Pro Glu Pro Arg Asn Gly Gly Leu
            820                 825                 830

Pro Cys Val Gly Asp Ala Ala Glu Tyr Gln Asp Cys Asn Pro Gln Ala
            835                 840                 845

Cys Pro Val Arg Gly Ala Trp Ser Cys Trp Thr Ser Trp Ser Pro Cys
850                 855                 860

Ser Ala Ser Cys Gly Gly Gly His Tyr Gln Arg Thr Arg Ser Cys Thr
865                 870                 875                 880

Ser Pro Ala Pro Ser Pro Gly Glu Asp Ile Cys Leu Gly Leu His Thr
                885                 890                 895

Glu Glu Ala Leu Cys Ala Thr Gln Ala Cys Pro Glu Gly Trp Ser Pro
                900                 905                 910

Trp Ser Glu Trp Ser Lys Cys Thr Asp Asp Gly Ala Gln Ser Arg Ser
            915                 920                 925

Arg His Cys Glu Glu Leu Leu Pro Gly Ser Ser Ala Cys Ala Gly Asn
            930                 935                 940
```

-continued

Ser Ser Gln Ser Arg Pro Cys Pro Tyr Ser Glu Ile Pro Gly Phe Asn
945                 950                 955                 960

Leu Ile His Leu Val Ala Thr Gly Ile Ser Cys Phe Leu Gly Ser Gly
            965                 970                 975

Leu Leu Thr Leu Ala Val Tyr Leu Ser Cys Gln His Cys Gln Arg Gln
        980                 985                 990

Ser Gln Glu Ser Thr Leu Val His Pro Ala Thr Pro Asn His Leu His
    995                 1000                1005

Tyr Lys Gly Gly Thr Pro Lys Asn Glu Lys Tyr Thr Pro Met Glu
    1010                1015                1020

Phe Lys Thr Leu Asn Lys Asn Leu Ile Pro Asp Asp Arg Ala Asn
1025                1030                1035                1040

Phe Tyr Pro Leu Gln Gln Thr Asn Val Tyr Thr Thr Tyr Tyr Pro
                1045                1050                1055

Ser Pro Leu Asn Lys His Ser Phe Arg Pro Glu Ala Ser Pro Gly Gln
            1060                1065                1070

Arg Cys Phe Pro Asn Ser
        1075

<210> SEQ ID NO 9
<211> LENGTH: 3456
<212> TYPE: DNA
<213> ORGANISM: homo sapiens

<400> SEQUENCE: 9

```
atgccctgtg gcttcagtcc gtctcctgtt gcccaccacc tcgtccctgg gccgcctgat      60
acccagccc aacagctaag gtgtggatgg acagtagggg gctggcttct ctcactggtc     120
agggtcttc tcccctgtct gcctcccgga gctaggactg cagaggggcc tatcatggtg     180
cttgcaggcc cctggctgt ctcgctgttg ctgcccagcc tcacactgct ggtgtcccac     240
ctctccagct cccaggatgt ctccagtgag cccagcagtg agcagcagct gtgcgccctt     300
agcaagcacc ccaccgtggc ctttgaagac ctgcagccgt gggtctctaa cttcacctac     360
cctggagccc gggatttctc ccagctggct ttggaccct ccgggracca gctcatcgtg     420
ggagccagga actacctctt cagactcagc cttgccaatg tctctcttct tcaggccaca     480
gagtgggcct ccagtgagga cacgcgccgc tcctgccaaa gcaaagggaa gactgaggag     540
gagtgtcaga actacgtgcg agtcctgatc gtcgccggcc ggaaggtgtt catgtgtgga     600
accaatgcct tttccccat gtgcaccagc agacaggtgg ggaacctcag ccggactatt     660
gagaagatca atggtgtggc ccgctgcccc tatgacccac gccacaactc cacagctgtc     720
atctcctccc agggggagct ctatgcagcc acggtcatcg acttctcagg tcgggaccct     780
gccatctacc gcagcctggg cagtgggcca ccgcttcgca ctgcccaata taactccaag     840
tggcttaatg agccaaactt cgtggcagcc tatgatattg ggctgtttgc atacttcttc     900
ctgcgggaga acgcagtgga gcacgactgt ggacgcaccg tgtactctcg cgtgccccgc     960
gtgtgcaaga atgacgtggg gggccgattc ctgctggagg acatggac cacattcatg    1020
aaggcccggc tcaactgctc ccgcccgggc gaggtcccct tctactataa cgagctgcag    1080
agtgccttcc acttgccrga gcaggacctc atctatggag ttttcacaac caacgtaaac    1140
agcatygcgg cttctgctgt ctgcgccttc aacctcagtg ctatctccca ggctttcaat    1200
ggcccatttc gctaccagga gaaccccagg gctgcctggc tccccatagc caaccccatc    1260
cccaatttcc agtgtggcac cctgcctgag accggtccca cgagaacct gacggagcgc    1320
```

```
agcctgcagg acgcgcagcg cctcttcctg atgagcgagg ccgtgcagcc ggtgacaccc    1380
gagccctgtg tcacccagga cagcgtgcgc ttctcacacc tcgtggtgga cctggtgcag    1440
gctaaagaca cgctctacca tgtactctac attggcaccg agtcgggcac catcctgaag    1500
gcgctgtcca cggcgagccg cagcctccac ggctgctacc tggaggagct gcacgtgctg    1560
ccccccgggc gccgcgagcc cctgcgcagc ctgcgcatcc tgcacagcgc ccgcgcgctc    1620
ttcgtggggc tgagagacgg cgtcctgcgg gtcccactgg agaggtgcgc cgcctaccgc    1680
agccaggggg catgcctggg ggcccgggac ccgtactgtg gctgggacgg gaagcagcaa    1740
cgttgcagca cactcgagga cagctccaac atgagcctct ggacccagaa catcaccgcc    1800
tgtcctgtgc ggaatgtgac acgggatggg ggcttcggcc catggtcacc atggcaacca    1860
tgtgagcact ggatggggga caactcaggc tcttgcctgt gtcgagctcg atcctgtgat    1920
tcccctcgac cccgctgtgg gggccttgac tgcctgggc cagccatcca catcgccaac    1980
tgctccagga tggggcgtg accccgtgg tcatcgtggg cgctgtgcag cacgtcctgt    2040
ggcatcggct tccaggtccg ccagcgaagt tgcagcaacc ctgctccccg ccacgggggc    2100
cgcatctgcg tgggcaagag ccgggaggaa cggttctgta atgagaacac gccttgcccg    2160
gtgcccatct tctgggcttc ctggggctcc tggagcaagt gcagcagcaa ctgtggaggg    2220
ggcatgcagt cgcggcgtcg ggcctgcgag aacggcaact cctgcctggg ctgcggcgtg    2280
gagttcaaga cgtgcaaccc cgagggctgc ccgaagtgc ggcgcaacac ccctggacg    2340 ccgtggctgc ccgtgaacgt gacgcagggc ggggcacggc aggagcagcg gttccgcttc    2400
acctgccgcg cgcccttgc agacccgcac ggcctgcagt tcggcaggag aaggaccgag    2460
acgaggacct gtcccgcgga cggctccggc tcctgcgaca ccgacgccct ggtggaggac    2520
ctcctgcgca gcgggagcac ctccccgcac acggtgagcg ggggctgggc cgcctggggc    2580
ccgtggtcgt cctgctcccg ggactgcgag ctgggcttcc gcgtccgcaa gagaacgtgc    2640
actaacccgg agccccgcaa cggggggcct ccctgcgtgg gcgatgctgc cgagtaccag    2700
gactgcaacc cccaggcttg cccagttcgg ggtgcttggt cctgctggac ctcatggtct    2760
ccatgctcag cttcctgtgg tggggtcac tatcaacgca cccgttcctg caccagcccc    2820
gcaccctccc caggtgagga catctgtctc gggctgcaca cggaggaggc actatgtgcc    2880
acacaggcct gcccagaagg ctggtcgccc tggtctgagt ggagtaagtg cactgacgac    2940
ggagcccaga gccgaagccg gcactgtgag gagctcctcc cagggtccag cgcctgtgct    3000
ggaaacagca gccagagccg ccctgccc tacagcgaga ttcccgtcat cctgccagcc    3060
tccagcatgg aggaggccac cggctgtgca gggttcaatc tcatccactt ggtggccacg    3120
ggcatctcct gcttcttggg ctctgggctc ctgacccag cagtgtacct gtcttgccag    3180
cactgccagc gtcagtccca ggagtccaca ctggtccatc ctgccacccc caaccatttg    3240
cactacaagg gcggaggcac ccgaagaat gaaaagtaca cacccatgga attcaagacc    3300
ctgaacaaga taacttgat ccctgatgac agagccaact tctacccatt gcagcagacc    3360
aatgtgtaca cgactactta ctacccaagc cccctgaaca aacacagctt ccggcccgag    3420
gcctcacctg acaacggtg cttccccaac agctga                              3456
```

<210> SEQ ID NO 10
<211> LENGTH: 1151
<212> TYPE: PRT
<213> ORGANISM: homo sapiens -continued

```
<400> SEQUENCE: 10

Met Pro Cys Gly Phe Ser Pro Ser Pro Val Ala His His Leu Val Pro
1               5                   10                  15

Gly Pro Pro Asp Thr Pro Ala Gln Gln Leu Arg Cys Gly Trp Thr Val
            20                  25                  30

Gly Gly Trp Leu Leu Ser Leu Val Arg Gly Leu Leu Pro Cys Leu Pro
        35                  40                  45

Pro Gly Ala Arg Thr Ala Glu Gly Pro Ile Met Val Leu Ala Gly Pro
    50                  55                  60

Leu Ala Val Ser Leu Leu Leu Pro Ser Leu Thr Leu Leu Val Ser His
65                  70                  75                  80

Leu Ser Ser Ser Gln Asp Val Ser Ser Glu Pro Ser Ser Glu Gln Gln
                85                  90                  95

Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
    210                 215                 220

Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
                245                 250                 255

Gly Arg Asp Pro Ala Ile Tyr Arg Ser Leu Gly Ser Gly Pro Pro Leu
            260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Leu Arg Glu Asn
    290                 295                 300

Ala Val Glu His Asp Cys Gly Arg Thr Val Tyr Ser Arg Val Ala Arg
305                 310                 315                 320

Val Cys Lys Asn Asp Val Gly Gly Arg Phe Leu Leu Glu Asp Thr Trp
                325                 330                 335

Thr Thr Phe Met Lys Ala Arg Leu Asn Cys Ser Arg Pro Gly Glu Val
            340                 345                 350

Pro Phe Tyr Tyr Asn Glu Leu Gln Ser Ala Phe His Leu Pro Glu Gln
        355                 360                 365

Asp Leu Ile Tyr Gly Val Phe Thr Thr Asn Val Asn Ser Ile Ala Ala
    370                 375                 380

Ser Ala Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415
```

```
Ala Asn Pro Ile Pro Asn Phe Gln Cys Gly Thr Leu Pro Glu Thr Gly
            420                 425                 430
Pro Asn Glu Asn Leu Thr Glu Arg Ser Leu Gln Asp Ala Gln Arg Leu
            435                 440                 445
Phe Leu Met Ser Glu Ala Val Gln Pro Val Thr Pro Glu Pro Cys Val
            450                 455                 460
Thr Gln Asp Ser Val Arg Phe Ser His Leu Val Val Asp Leu Val Gln
465                 470                 475                 480
Ala Lys Asp Thr Leu Tyr His Val Leu Tyr Ile Gly Thr Glu Ser Gly
                485                 490                 495
Thr Ile Leu Lys Ala Leu Ser Thr Ala Ser Arg Ser Leu His Gly Cys
                500                 505                 510
Tyr Leu Glu Glu Leu His Val Leu Pro Pro Gly Arg Arg Glu Pro Leu
                515                 520                 525
Arg Ser Leu Arg Ile Leu His Ser Ala Arg Ala Leu Phe Val Gly Leu
            530                 535                 540
Arg Asp Gly Val Leu Arg Val Pro Leu Glu Arg Cys Ala Ala Tyr Arg
545                 550                 555                 560
Ser Gln Gly Ala Cys Leu Gly Ala Arg Asp Pro Tyr Cys Gly Trp Asp
                565                 570                 575
Gly Lys Gln Gln Arg Cys Ser Thr Leu Glu Asp Ser Ser Asn Met Ser
                580                 585                 590
Leu Trp Thr Gln Asn Ile Thr Ala Cys Pro Val Arg Asn Val Thr Arg
                595                 600                 605
Asp Gly Gly Phe Gly Pro Trp Ser Pro Trp Gln Pro Cys Glu His Leu
            610                 615                 620
Asp Gly Asp Asn Ser Gly Ser Cys Leu Cys Arg Ala Arg Ser Cys Asp
625                 630                 635                 640
Ser Pro Arg Pro Arg Cys Gly Gly Leu Asp Cys Leu Gly Pro Ala Ile
                645                 650                 655
His Ile Ala Asn Cys Ser Arg Asn Gly Ala Trp Thr Pro Trp Ser Ser
                660                 665                 670
Trp Ala Leu Cys Ser Thr Ser Cys Gly Ile Gly Phe Gln Val Arg Gln
                675                 680                 685
Arg Ser Cys Ser Asn Pro Ala Pro Arg His Gly Gly Arg Ile Cys Val
            690                 695                 700
Gly Lys Ser Arg Glu Glu Arg Phe Cys Asn Glu Asn Thr Pro Cys Pro
705                 710                 715                 720
Val Pro Ile Phe Trp Ala Ser Trp Gly Ser Trp Ser Lys Cys Ser Ser
                725                 730                 735
Asn Cys Gly Gly Gly Met Gln Ser Arg Arg Arg Ala Cys Glu Asn Gly
            740                 745                 750
Asn Ser Cys Leu Gly Cys Gly Val Glu Phe Lys Thr Cys Asn Pro Glu
            755                 760                 765
Gly Cys Pro Glu Val Arg Arg Asn Thr Pro Trp Thr Pro Trp Leu Pro
            770                 775                 780
Val Asn Val Thr Gln Gly Gly Ala Arg Gln Glu Gln Arg Phe Arg Phe
785                 790                 795                 800
Thr Cys Arg Ala Pro Leu Ala Asp Pro His Gly Leu Gln Phe Gly Arg
                805                 810                 815
Arg Arg Thr Glu Thr Arg Thr Cys Pro Ala Asp Gly Ser Gly Ser Cys
            820                 825                 830
```

```
Asp Thr Asp Ala Leu Val Glu Asp Leu Leu Arg Ser Gly Ser Thr Ser
        835                 840                 845
Pro His Thr Val Ser Gly Gly Trp Ala Ala Trp Gly Pro Trp Ser Ser
    850                 855                 860
Cys Ser Arg Asp Cys Glu Leu Gly Phe Arg Val Arg Lys Arg Thr Cys
865                 870                 875                 880
Thr Asn Pro Glu Pro Arg Asn Gly Gly Leu Pro Cys Val Gly Asp Ala
                885                 890                 895
Ala Glu Tyr Gln Asp Cys Asn Pro Gln Ala Cys Pro Val Arg Gly Ala
            900                 905                 910
Trp Ser Cys Trp Thr Ser Trp Ser Pro Cys Ser Ala Ser Cys Gly Gly
        915                 920                 925
Gly His Tyr Gln Arg Thr Arg Ser Cys Thr Ser Pro Ala Pro Ser Pro
    930                 935                 940
Gly Glu Asp Ile Cys Leu Gly Leu His Thr Glu Glu Ala Leu Cys Ala
945                 950                 955                 960
Thr Gln Ala Cys Pro Glu Gly Trp Ser Pro Trp Ser Glu Trp Ser Lys
                965                 970                 975
Cys Thr Asp Asp Gly Ala Gln Ser Arg Ser Arg His Cys Glu Glu Leu
            980                 985                 990
Leu Pro Gly Ser Ser Ala Cys Ala Gly Asn Ser Ser Gln Ser Arg Pro
        995                 1000                1005
Cys Pro Tyr Ser Glu Ile Pro Val Ile Leu Pro Ala Ser Ser Met Glu
    1010                1015                1020
Glu Ala Thr Gly Cys Ala Gly Phe Asn Leu Ile His Leu Val Ala Thr
1025                1030                1035                1040
Gly Ile Ser Cys Phe Leu Gly Ser Gly Leu Leu Thr Leu Ala Val Tyr
                1045                1050                1055
Leu Ser Cys Gln His Cys Gln Arg Gln Ser Gln Glu Ser Thr Leu Val
            1060                1065                1070
His Pro Ala Thr Pro Asn His Leu His Tyr Lys Gly Gly Gly Thr Pro
        1075                1080                1085
Lys Asn Glu Lys Tyr Thr Pro Met Glu Phe Lys Thr Leu Asn Lys Asn
    1090                1095                1100
Asn Leu Ile Pro Asp Asp Arg Ala Asn Phe Tyr Pro Leu Gln Gln Thr
1105                1110                1115                1120
Asn Val Tyr Thr Thr Thr Tyr Tyr Pro Ser Pro Leu Asn Lys His Ser
                1125                1130                1135
Phe Arg Pro Glu Ala Ser Pro Gly Gln Arg Cys Phe Pro Asn Ser
            1140                1145                1150

<210> SEQ ID NO 11
<211> LENGTH: 3411
<212> TYPE: DNA
<213> ORGANISM: homo sapiens

<400> SEQUENCE: 11
atgccctgtg gcttcagtcc gtctcctgtt gcccaccacc tcgtccctgg gccgcctgat      60 acccagccc  aacagctaag gtgtggatgg acagtagggg gctggcttct ctcactggtc     120 agggtcttc  tccctgtct  gcctcccgga gctaggactg cagagggcc  tatcatggtg     180 cttgcaggcc cctggctgt  ctcgctgttg ctgcccagcc tcacactgct ggtgtcccac     240
ctctccagct cccaggatgt ctccagtgag cccagcagtg agcagcagct gtgcgccctt     300
agcaagcacc ccaccgtggc ctttgaagac ctgcagccgt gggtctctaa cttcacctac     360
```

-continued

```
cctggagccc gggatttctc ccagctggct ttggacccct ccgggracca gctcatcgtg      420
ggagccagga actacctctt cagactcagc cttgccaatg tctctcttct tcaggccaca      480
gagtgggcct ccagtgagga cacgcgccgc tcctgccaaa gcaaagggaa gactgaggag      540
gagtgtcaga actacgtgcg agtcctgatc gtcgccggcc ggaaggtgtt catgtgtgga      600
accaatgcct tttcccccat gtgcaccagc agacaggtgg ggaacctcag ccggactatt      660
gagaagatca atggtgtggc ccgctgcccc tatgacccac gccacaactc cacagctgtc      720
atctcctccc aggggagct ctatgcagcc acggtcatcg acttctcagg tcgggaccct      780
gccatctacc gcagcctggg cagtgggcca ccgcttcgca ctgcccaata taactccaag      840
tggcttaatg agccaaactt cgtggcagcc tatgatattg gctgtttgc atacttcttc       900 ctgcgggaga acgcagtgga gcacgactgt ggacgcaccg tgtactctcg cgtggcccgc      960
gtgtgcaaga atgacgtggg gggccgattc ctgctggagg acacatggac acattcatg     1020 aaggcccggc tcaactgctc ccgcccgggc gaggtcccct tctactataa cgagctgcag     1080
agtgccttcc acttgccrga gcaggacctc atctatggga ttttcacaac caacgtaaac     1140
agcatygcgg cttctgctgt ctgcgccttc aacctcagtg ctatctccca ggctttcaat     1200
ggcccatttc gctaccagga gaaccccagg gctgcctggc tccccatagc caaccccatc     1260
cccaatttcc agtgtggcac cctgcctgag accggtccca acgagaacct gacggagcgc     1320
agcctgcagg acgcgcagcg cctcttcctg atgagcgagg ccgtgcagcc ggtgacaccc     1380
gagccctgtg tcacccagga cagcgtgcgc ttctcacacc tcgtggtgga cctggtgcag     1440
gctaaagaca cgctctacca tgtactctac attggcaccg agtcgggcac catcctgaag     1500
gcgctgtcca cggcgagccg cagcctccac ggctgctacc tggaggagct gcacgtgctg     1560 cccccgggc gccgcgagcc cctgcgcagc ctgcgcatcc tgcacagcgc ccgcgcgctc     1620 ttcgtgggc tgagagacgg cgtcctgcgg gtcccactgg agaggtgcgc cgcctaccgc     1680
agccaggggg catgcctggg ggcccgggac ccgtactgtg gctgggacgg gaagcagcaa     1740
cgttgcagca cactcgagga cagctccaac atgagcctct ggacccagaa catcaccgcc     1800
tgtcctgtgc ggaatgtgac acgggatggg ggcttcggcc catggtcacc atggcaacca     1860
tgtgagcact tggatgggga caactcaggc tcttgcctgt gtcgagctcg atcctgtgat     1920
tcccctcgac cccgctgtgg gggccttgac tgcctgggc cagccatcca catcgccaac     1980
tgctccagga atggggcgtg gaccccgtgg tcatcgtggg cgctgtgcag cacgtcctgt     2040
ggcatcggct tccaggtccg ccagcgaagt tgcagcaacc ctgctccccg ccacgggggc     2100
cgcatctgcg tgggcaagag ccgggaggaa cggttctgta atgagaacac gccttgcccg     2160
gtgcccatct tctgggcttc ctggggctcc tggagcaagt gcagcagcaa ctgtggaggg     2220
ggcatgcagt cgcggcgtcg ggcctgcgag aacggcaact cctgcctggg ctgcggcgtg     2280
gagttcaaga cgtgcaaccc cgagggctgc cccgaagtgc ggcgcaacac cccctggacg     2340
ccgtggctgc ccgtgaacgt gacgcagggc ggggcacggc aggagcagcg gttccgcttc     2400
acctgccgcg cgcccttgc agacccgcac ggcctgcagt tcggcaggag aaggaccgag     2460
acgaggacct gtcccgcgga cggctccggc tcctgcgaca ccgacgccct ggtggaggac     2520
ctcctgcgca gcggagcac ctccccgcac acggtgagcg ggggctgggc cgcctgggc     2580 ccgtggtcgt cctgctcccg ggactgcgag ctgggcttcc gcgtccgcaa gagaacgtgc     2640
actaacccgg agccccgcaa cggggggcctg ccctgcgtgg gcgatgctgc cgagtaccag     2700
```

-continued

```
gactgcaacc cccaggcttg cccagttcgg ggtgcttggt cctgctggac ctcatggtct    2760
ccatgctcag cttcctgtgg tgggggtcac tatcaacgca cccgttcctg caccagcccc    2820
gcaccctccc caggtgagga catctgtctc gggctgcaca cggaggaggc actatgtgcc    2880
acacaggcct gcccagaagg ctggtcgccc tggtctgagt ggagtaagtg cactgacgac    2940
ggagcccaga gccgaagccg gcactgtgag gagctcctcc cagggtccag cgcctgtgct    3000
ggaaacagca gccagagccg cccctgcccc tacagcgaga ttcccgggtt caatctcatc    3060
cacttggtgg ccacgggcat ctcctgcttc ttgggctctg ggctcctgac cctagcagtg    3120
tacctgtctt gccagcactg ccagcgtcag tcccaggagt ccacactggt ccatcctgcc    3180
acccccaacc atttgcacta aagggcgga ggcaccccga agaatgaaaa gtacacaccc    3240
atggaattca agaccctgaa caagaataac ttgatccctg atgacagagc caacttctac    3300
ccattgcagc agaccaatgt gtacacgact acttactacc caagcccccct gaacaaacac    3360 agcttccggc ccgaggcctc acctggacaa cggtgcttcc caacagctg a              3411
```

<210> SEQ ID NO 12
<211> LENGTH: 1136
<212> TYPE: PRT
<213> ORGANISM: homo sapiens

<400> SEQUENCE: 12

```
Met Pro Cys Gly Phe Ser Pro Ser Pro Val Ala His His Leu Val Pro
1               5                   10                  15

Gly Pro Pro Asp Thr Pro Ala Gln Gln Leu Arg Cys Gly Trp Thr Val
                20                  25                  30

Gly Gly Trp Leu Leu Ser Leu Val Arg Gly Leu Leu Pro Cys Leu Pro
            35                  40                  45

Pro Gly Ala Arg Thr Ala Glu Gly Pro Ile Met Val Leu Ala Gly Pro
        50                  55                  60

Leu Ala Val Ser Leu Leu Leu Pro Ser Leu Thr Leu Leu Val Ser His
65                  70                  75                  80

Leu Ser Ser Ser Gln Asp Val Ser Glu Pro Ser Ser Glu Gln Gln
                85                  90                  95

Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
    210                 215                 220

Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
                245                 250                 255
```

-continued

```
Gly Arg Asp Pro Ala Ile Tyr Arg Ser Leu Gly Ser Gly Pro Pro Leu
        260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Phe Leu Arg Glu Asn
        290                 295                 300

Ala Val Glu His Asp Cys Gly Arg Thr Val Tyr Ser Arg Val Ala Arg
305                 310                 315                 320

Val Cys Lys Asn Asp Val Gly Gly Arg Phe Leu Leu Glu Asp Thr Trp
                325                 330                 335

Thr Thr Phe Met Lys Ala Arg Leu Asn Cys Ser Arg Pro Gly Glu Val
                340                 345                 350

Pro Phe Tyr Tyr Asn Glu Leu Gln Ser Ala Phe His Leu Pro Glu Gln
            355                 360                 365

Asp Leu Ile Tyr Gly Val Phe Thr Thr Asn Val Asn Ser Ile Ala Ala
        370                 375                 380

Ser Ala Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415

Ala Asn Pro Ile Pro Asn Phe Gln Cys Gly Thr Leu Pro Glu Thr Gly
                420                 425                 430

Pro Asn Glu Asn Leu Thr Glu Arg Ser Leu Gln Asp Ala Gln Arg Leu
            435                 440                 445

Phe Leu Met Ser Glu Ala Val Gln Pro Val Thr Pro Glu Pro Cys Val
        450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
                500                 505                 510

Tyr Leu Glu Glu Leu His Val Leu Pro Pro Gly Arg Arg Glu Pro Leu
            515                 520                 525

Arg Ser Leu Arg Ile Leu His Ser Ala Arg Ala Leu Phe Val Gly Leu
        530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
                580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
        610                 615                 620

Asp Gly Asp Asn Ser Gly Ser Cys Leu Cys Arg Ala Arg Ser Cys Asp
625                 630                 635                 640

Ser Pro Arg Pro Arg Cys Gly Gly Leu Asp Cys Leu Gly Pro Ala Ile
                645                 650                 655

His Ile Ala Asn Cys Ser Arg Asn Gly Ala Trp Thr Pro Trp Ser Ser
                660                 665                 670
```

```
-continued

Trp Ala Leu Cys Ser Thr Ser Cys Gly Ile Gly Phe Gln Val Arg Gln
            675                 680                 685

Arg Ser Cys Ser Asn Pro Ala Pro Arg His Gly Gly Arg Ile Cys Val
        690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
            725                 730                 735

Asn Cys Gly Gly Gly Met Gln Ser Arg Arg Ala Cys Glu Asn Gly
            740                 745                 750

Asn Ser Cys Leu Gly Cys Gly Val Glu Phe Lys Thr Cys Asn Pro Glu
        755                 760                 765

Gly Cys Pro Glu Val Arg Arg Asn Thr Pro Trp Thr Pro Trp Leu Pro
770                 775                 780

Val Asn Val Thr Gln Gly Gly Ala Arg Gln Glu Gln Arg Phe Arg Phe
785                 790                 795                 800

Thr Cys Arg Ala Pro Leu Ala Asp Pro His Gly Leu Gln Phe Gly Arg
            805                 810                 815

Arg Arg Thr Glu Thr Arg Thr Cys Pro Ala Asp Gly Ser Gly Ser Cys
        820                 825                 830

Asp Thr Asp Ala Leu Val Glu Asp Leu Leu Arg Ser Gly Ser Thr Ser
            835                 840                 845

Pro His Thr Val Ser Gly Gly Trp Ala Ala Trp Gly Pro Trp Ser Ser
    850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
            900                 905                 910

Trp Ser Cys Trp Thr Ser Trp Ser Pro Cys Ser Ala Ser Cys Gly Gly
        915                 920                 925

Gly His Tyr Gln Arg Thr Arg Ser Cys Thr Ser Pro Ala Pro Ser Pro
    930                 935                 940

Gly Glu Asp Ile Cys Leu Gly Leu His Thr Glu Glu Ala Leu Cys Ala
945                 950                 955                 960

Thr Gln Ala Cys Pro Glu Gly Trp Ser Pro Trp Ser Glu Trp Ser Lys
            965                 970                 975

Cys Thr Asp Asp Gly Ala Gln Ser Arg Ser Arg His Cys Glu Glu Leu
        980                 985                 990

Leu Pro Gly Ser Ser Ala Cys Ala Gly Asn Ser Ser Gln Ser Arg Pro
    995                 1000                1005

Cys Pro Tyr Ser Glu Ile Pro Gly Phe Asn Leu Ile His Leu Val Ala
    1010                1015                1020

Thr Gly Ile Ser Cys Phe Leu Gly Ser Gly Leu Leu Thr Leu Ala Val
1025                1030                1035                1040

Tyr Leu Ser Cys Gln His Cys Gln Arg Gln Ser Gln Glu Ser Thr Leu
            1045                1050                1055

Val His Pro Ala Thr Pro Asn His Leu His Tyr Lys Gly Gly Gly Thr
        1060                1065                1070

Pro Lys Asn Glu Lys Tyr Thr Pro Met Glu Phe Lys Thr Leu Asn Lys
    1075                1080                1085

Asn Asn Leu Ile Pro Asp Asp Arg Ala Asn Phe Tyr Pro Leu Gln Gln
```

|   | 1090 |   |   | 1095 |   |   | 1100 |   |   |
|---|---|---|---|---|---|---|---|---|---|
| Thr | Asn | Val | Tyr | Thr | Thr | Thr | Tyr | Tyr | Pro | Ser | Pro | Leu | Asn | Lys | His |
| 1105 |   |   |   | 1110 |   |   |   | 1115 |   |   |   | 1120 |

Ser Phe Arg Pro Glu Ala Ser Pro Gly Gln Arg Cys Phe Pro Asn Ser
                1125                    1130                  1135

<210> SEQ ID NO 13
<211> LENGTH: 2865
<212> TYPE: DNA
<213> ORGANISM: homo sapiens

<400> SEQUENCE: 13

| | | | | | |
|---|---|---|---|---|---|
| atgtgtggaa | ccaatgcctt | ttcccccatg | tgcaccagca | gacaggtggg | gaacctcagc | 60 |
| cggactattg | agaagatcaa | tggtgtggcc | cgctgcccct | atgacccacg | ccacaactcc | 120 |
| acagctgtca | tctcctccca | gggggagctc | tatgcagcca | cggtcatcga | cttctcaggt | 180 |
| cgggaccctg | ccatctaccg | cagcctgggc | agtgggccac | cgcttcgcac | tgcccaatat | 240 |
| aactccaagt | ggcttaatga | gccaaacttc | gtggcagcct | atgatattgg | gctgtttgca | 300 |
| tacttcttcc | tgcgggagaa | cgcagtggag | cacgactgtg | gacgcaccgt | gtactctcgc | 360 |
| gtggcccgcg | tgtgcaagaa | tgacgtgggg | ggccgattcc | tgctggagga | cacatggacc | 420 |
| acattcatga | aggcccggct | caactgctcc | cgccgggcg | aggtcccctt | ctactataac | 480 |
| gagctgcaga | gtgccttcca | cttgccrgag | caggacctca | tctatggagt | tttcacaacc | 540 |
| aacgtaaaca | gcatygcggc | ttctgctgtc | tgcgccttca | acctcagtgc | tatctcccag | 600 |
| gctttcaatg | cccatttcg | ctaccaggag | aaccccaggg | ctgcctggct | cccatagcc | 660 |
| aaccccatcc | ccaatttcca | gtgtggcacc | ctgcctgaga | ccggtcccaa | cgagaacctg | 720 |
| acggagcgca | gcctgcagga | cgcgcagcgc | ctcttcctga | tgagcgaggc | cgtgcagccg | 780 |
| gtgacacccg | agccctgtgt | cacccaggac | agcgtgcgct | tctcacacct | cgtggtggac | 840 |
| ctggtgcagg | ctaaagacac | gctctaccat | gtactctaca | ttggcaccga | gtcgggcacc | 900 |
| atcctgaagg | cgctgtccac | ggcgagccgc | agcctccacg | ctgctacct | ggaggagctg | 960 |
| cacgtgctgc | ccccgggcg | ccgcgagccc | ctgcgcagcc | tgcgcatcct | gcacagcgcc | 1020 |
| cgcgcgctct | tcgtggggct | gagagacggc | gtcctgcggg | tcccactgga | gaggtgcgcc | 1080 |
| gcctaccgca | gccaggggc | atgcctgggg | gcccgggacc | cgtactgtgg | ctgggacggg | 1140 |
| aagcagcaac | gttgcagcac | actcgaggac | agctccaaca | tgagcctctg | gacccagaac | 1200 |
| atcaccgcct | gtcctgtgcg | gaatgtgaca | cgggatgggg | gcttcggccc | atggtcacca | 1260 |
| tggcaaccat | gtgagcactt | ggatggggac | aactcaggct | cttgcctgtg | tcgagctcga | 1320 |
| tcctgtgatt | ccctcgacc | ccgctgtggg | ggccttgact | gcctggggcc | agccatccac | 1380 |
| atcgccaact | gctccaggaa | tgggcgtgg | acccgtggt | catcgtgggc | gctgtgcagc | 1440 |
| acgtcctgtg | gcatcggctt | ccaggtccgc | cagcgaagtt | gcagcaaccc | tgctccccgc | 1500 |
| cacgggggcc | gcatctgcgt | gggcaagagc | cggaggaac | ggttctgtaa | tgagaacacg | 1560 |
| ccttgcccgg | tgcccatctt | ctgggcttcc | tggggctcct | ggagcaagtg | cagcagcaac | 1620 |
| tgtggagggg | gcatgcagtc | gcggcgtcgg | gcctgcgaga | acggcaactc | ctgcctgggc | 1680 |
| tgcggcgtgg | agttcaagac | gtgcaacccc | gagggctgcc | ccgaagtgcg | cgcaacacc | 1740 |
| ccctggacgc | cgtggctgcc | cgtgaacgtg | acgcagggcg | gggcacggca | ggagcagcgg | 1800 |
| ttccgcttca | cctgccgcgc | gccccttgca | gacccgcacg | gcctgcagtt | cggcaggaga | 1860 |
| aggaccgaga | cgaggacctg | tcccgcggac | ggctccggct | cctgcgacac | cgacgccctg | 1920 |

-continued

```
gtggaggacc tcctgcgcag cgggagcacc tccccgcaca cggtgagcgg gggctgggcc    1980
gcctggggcc cgtggtcgtc ctgctcccgg gactgcgagc tgggcttccg cgtccgcaag    2040
agaacgtgca ctaacccgga gccccgcaac ggggggcctgc cctgcgtggg cgatgctgcc   2100
gagtaccagg actgcaaccc ccaggcttgc ccagttcggg gtgcttggtc ctgctggacc    2160
tcatggtctc catgctcagc ttcctgtggt ggggtcact atcaacgcac ccgttcctgc     2220
accagccccg caccctcccc aggtgaggac atctgtctcg gcctgcacac ggaggaggca    2280
ctatgtgcca cacaggcctg cccagaaggc tggtcgccct ggtctgagtg gagtaagtgc    2340
actgacgacg gagcccagag ccgaagccgg cactgtgagg agctcctccc agggtccagc    2400
gcctgtgctg gaaacagcag ccagagccgc ccctgcccct acagcgagat tcccgtcatc    2460
ctgccagcct ccagcatgga ggaggccacc ggctgtgcag ggttcaatct catccacttg    2520
gtggccacgg gcatctcctg cttcttgggc tctgggctcc tgaccctagc agtgtacctg    2580
tcttgccagc actgccagcg tcagtcccag gagtccacac tggtccatcc tgccaccccc    2640
aaccatttgc actacaaggg cggaggcacc ccgaagaatg aaaagtacac acccatggaa    2700
ttcaagaccc tgaacaagaa taacttgatc cctgatgaca gagccaactt ctacccattg    2760
cagcagacca atgtgtacac gactacttac tacccaagcc ccctgaacaa acacagcttc    2820
cggcccgagg cctcacctgg acaacggtgc ttccccaaca gctga                   2865
```

<210> SEQ ID NO 14
<211> LENGTH: 954
<212> TYPE: PRT
<213> ORGANISM: homo sapiens

<400> SEQUENCE: 14

```
Met Cys Gly Thr Asn Ala Phe Ser Pro Met Cys Thr Ser Arg Gln Val
 1               5                  10                  15

Gly Asn Leu Ser Arg Thr Ile Glu Lys Ile Asn Gly Val Ala Arg Cys
            20                  25                  30

Pro Tyr Asp Pro Arg His Asn Ser Thr Ala Val Ile Ser Ser Gln Gly
        35                  40                  45

Glu Leu Tyr Ala Ala Thr Val Ile Asp Phe Ser Gly Arg Asp Pro Ala
    50                  55                  60

Ile Tyr Arg Ser Leu Gly Ser Gly Pro Pro Leu Arg Thr Ala Gln Tyr
65                  70                  75                  80

Asn Ser Lys Trp Leu Asn Glu Pro Asn Phe Val Ala Ala Tyr Asp Ile
                85                  90                  95

Gly Leu Phe Ala Tyr Phe Phe Leu Arg Glu Asn Ala Val Glu His Asp
            100                 105                 110

Cys Gly Arg Thr Val Tyr Ser Arg Val Ala Arg Val Cys Lys Asn Asp
        115                 120                 125

Val Gly Gly Arg Phe Leu Leu Glu Asp Thr Trp Thr Thr Phe Met Lys
    130                 135                 140

Ala Arg Leu Asn Cys Ser Arg Pro Gly Glu Val Pro Phe Tyr Tyr Asn
145                 150                 155                 160

Glu Leu Gln Ser Ala Phe His Leu Pro Glu Gln Asp Leu Ile Tyr Gly
                165                 170                 175

Val Phe Thr Thr Asn Val Asn Ser Ile Ala Ala Ser Ala Val Cys Ala
            180                 185                 190

Phe Asn Leu Ser Ala Ile Ser Gln Ala Phe Asn Gly Pro Phe Arg Tyr
        195                 200                 205
```

```
Gln Glu Asn Pro Arg Ala Ala Trp Leu Pro Ile Ala Asn Pro Ile Pro
    210                 215                 220

Asn Phe Gln Cys Gly Thr Leu Pro Glu Thr Gly Pro Asn Glu Asn Leu
225                 230                 235                 240

Thr Glu Arg Ser Leu Gln Asp Ala Gln Arg Leu Phe Leu Met Ser Glu
            245                 250                 255

Ala Val Gln Pro Val Thr Pro Glu Pro Cys Val Thr Gln Asp Ser Val
                260                 265                 270

Arg Phe Ser His Leu Val Val Asp Leu Val Gln Ala Lys Asp Thr Leu
            275                 280                 285

Tyr His Val Leu Tyr Ile Gly Thr Glu Ser Gly Thr Ile Leu Lys Ala
    290                 295                 300

Leu Ser Thr Ala Ser Arg Ser Leu His Gly Cys Tyr Leu Glu Glu Leu
305                 310                 315                 320

His Val Leu Pro Pro Gly Arg Arg Glu Pro Leu Arg Ser Leu Arg Ile
                325                 330                 335

Leu His Ser Ala Arg Ala Leu Phe Val Gly Leu Arg Asp Gly Val Leu
            340                 345                 350

Arg Val Pro Leu Glu Arg Cys Ala Ala Tyr Arg Ser Gln Gly Ala Cys
            355                 360                 365

Leu Gly Ala Arg Asp Pro Tyr Cys Gly Trp Asp Gly Lys Gln Gln Arg
370                 375                 380

Cys Ser Thr Leu Glu Asp Ser Ser Asn Met Ser Leu Trp Thr Gln Asn
385                 390                 395                 400

Ile Thr Ala Cys Pro Val Arg Asn Val Thr Arg Asp Gly Gly Phe Gly
                405                 410                 415

Pro Trp Ser Pro Trp Gln Pro Cys Glu His Leu Asp Gly Asp Asn Ser
                420                 425                 430

Gly Ser Cys Leu Cys Arg Ala Arg Ser Cys Asp Ser Pro Arg Pro Arg
            435                 440                 445

Cys Gly Gly Leu Asp Cys Leu Gly Pro Ala Ile His Ile Ala Asn Cys
450                 455                 460

Ser Arg Asn Gly Ala Trp Thr Pro Trp Ser Ser Trp Ala Leu Cys Ser
465                 470                 475                 480

Thr Ser Cys Gly Ile Gly Phe Gln Val Arg Gln Arg Ser Cys Ser Asn
                485                 490                 495

Pro Ala Pro Arg His Gly Gly Arg Ile Cys Val Gly Lys Ser Arg Glu
                500                 505                 510

Glu Arg Phe Cys Asn Glu Asn Thr Pro Cys Pro Val Pro Ile Phe Trp
            515                 520                 525

Ala Ser Trp Gly Ser Trp Ser Lys Cys Ser Ser Asn Cys Gly Gly Gly
530                 535                 540

Met Gln Ser Arg Arg Arg Ala Cys Glu Asn Gly Asn Ser Cys Leu Gly
545                 550                 555                 560

Cys Gly Val Glu Phe Lys Thr Cys Asn Pro Glu Gly Cys Pro Glu Val
                565                 570                 575

Arg Arg Asn Thr Pro Trp Thr Pro Trp Leu Pro Val Asn Val Thr Gln
            580                 585                 590

Gly Gly Ala Arg Gln Glu Gln Arg Phe Arg Phe Thr Cys Arg Ala Pro
            595                 600                 605

Leu Ala Asp Pro His Gly Leu Gln Phe Gly Arg Arg Thr Glu Thr
610                 615                 620
```

```
Arg Thr Cys Pro Ala Asp Gly Ser Gly Ser Cys Asp Thr Asp Ala Leu
625                 630                 635                 640

Val Glu Asp Leu Leu Arg Ser Gly Ser Thr Ser Pro His Thr Val Ser
            645                 650                 655

Gly Gly Trp Ala Ala Trp Gly Pro Trp Ser Ser Cys Ser Arg Asp Cys
        660                 665                 670

Glu Leu Gly Phe Arg Val Arg Lys Arg Thr Cys Thr Asn Pro Glu Pro
    675                 680                 685

Arg Asn Gly Gly Leu Pro Cys Val Gly Asp Ala Ala Glu Tyr Gln Asp
690                 695                 700

Cys Asn Pro Gln Ala Cys Pro Val Arg Gly Ala Trp Ser Cys Trp Thr
705                 710                 715                 720

Ser Trp Ser Pro Cys Ser Ala Ser Cys Gly Gly His Tyr Gln Arg
            725                 730                 735

Thr Arg Ser Cys Thr Ser Pro Ala Pro Ser Pro Gly Glu Asp Ile Cys
            740                 745                 750

Leu Gly Leu His Thr Glu Glu Ala Leu Cys Ala Thr Gln Ala Cys Pro
            755                 760                 765

Glu Gly Trp Ser Pro Trp Ser Glu Trp Ser Lys Cys Thr Asp Asp Gly
770                 775                 780

Ala Gln Ser Arg Ser Arg His Cys Glu Glu Leu Leu Pro Gly Ser Ser
785                 790                 795                 800

Ala Cys Ala Gly Asn Ser Ser Gln Ser Arg Pro Cys Pro Tyr Ser Glu
            805                 810                 815

Ile Pro Val Ile Leu Pro Ala Ser Ser Met Glu Glu Ala Thr Gly Cys
            820                 825                 830

Ala Gly Phe Asn Leu Ile His Leu Val Ala Thr Gly Ile Ser Cys Phe
835                 840                 845

Leu Gly Ser Gly Leu Leu Thr Leu Ala Val Tyr Leu Ser Cys Gln His
    850                 855                 860

Cys Gln Arg Gln Ser Gln Glu Ser Thr Leu Val His Pro Ala Thr Pro
865                 870                 875                 880

Asn His Leu His Tyr Lys Gly Gly Thr Pro Lys Asn Glu Lys Tyr
            885                 890                 895

Thr Pro Met Glu Phe Lys Thr Leu Asn Lys Asn Leu Ile Pro Asp
        900                 905                 910

Asp Arg Ala Asn Phe Tyr Pro Leu Gln Gln Thr Asn Val Tyr Thr Thr
        915                 920                 925

Thr Tyr Tyr Pro Ser Pro Leu Asn Lys His Ser Phe Arg Pro Glu Ala
    930                 935                 940

Ser Pro Gly Gln Arg Cys Phe Pro Asn Ser
945                 950

<210> SEQ ID NO 15
<211> LENGTH: 2820
<212> TYPE: DNA
<213> ORGANISM: homo sapiens

<400> SEQUENCE: 15
atgtgtggaa ccaatgcctt tccccccatg tgcaccagca gacaggtggg gaacctcagc      60
cggactattg agaagatcaa tggtgtggcc cgctgcccct atgacccacg ccacaactcc     120
acagctgtca tctcctccca gggggagctc tatgcagcca cggtcatcga cttctcaggt     180
cgggaccctg ccatctaccg cagcctgggc agtgggccac cgcttcgcac tgcccaatat     240
```

-continued

| | | |
|---|---|---|
| aactccaagt ggcttaatga gccaaacttc gtggcagcct atgatattgg gctgtttgca | 300 |
| tacttcttcc tgcgggagaa cgcagtggag cacgactgtg gacgcaccgt gtactctcgc | 360 |
| gtggcccgcg tgtgcaagaa tgacgtgggg gccgattcc tgctggagga cacatggacc | 420 |
| acattcatga aggcccggct caactgctcc cgcccgggcg aggtccccctt ctactataac | 480 |
| gagctgcaga gtgccttcca cttgccrgaga caggacctca tctatggagt tttcacaacc | 540 |
| aacgtaaaca gcatygcggc ttctgctgtc tgcgccttca acctcagtgc tatctcccag | 600 |
| gctttcaatg gccatttcg ctaccaggag aaccccaggg ctgcctggct ccccatagcc | 660 |
| aaccccatcc ccaatttcca gtgtggcacc ctgcctgaga ccggtcccaa cgagaacctg | 720 |
| acggagcgca gcctgcagga cgcgcagcgc ctcttcctga tgagcgaggc cgtgcagccg | 780 |
| gtgacacccg agccctgtgt cacccaggac agcgtgcgct tctcacacct cgtggtggac | 840 |
| ctggtgcagg ctaaagacac gctctaccat gtactctaca ttggcaccga gtcgggcacc | 900 |
| atcctgaagg cgctgtccac ggcgagccgc agcctccacg gctgctacct ggaggagctg | 960 |
| cacgtgctgc ccccgggcg ccgcgagccc ctgcgcagcc tgcgcatcct gcacagcgcc | 1020 |
| cgcgcgctct tcgtggggct gagagacggc gtcctgcggg tcccactgga gaggtgcgcc | 1080 |
| gcctaccgca gccaggggc atgcctgggg gcccggacc cgtactgtgg ctgggacggg | 1140 |
| aagcagcaac gttgcagcac actcgaggac agctccaaca tgagcctctg gacccagaac | 1200 |
| atcaccgcct gtcctgtgcg gaatgtgaca cgggatgggg gcttcggccc atggtcacca | 1260 |
| tggcaaccat gtgagcactt ggatggggac aactcaggct cttgcctgtg tcgagctcga | 1320 |
| tcctgtgatt cccctcgacc ccgctgtggg ggccttgact gcctggggcc agccatccac | 1380 |
| atcgccaact gctccaggaa tggggcgtgg accccgtggt catcgtgggc gctgtgcagc | 1440 |
| acgtcctgtg gcatcggctt ccaggtccgc cagcgaagtt gcagcaaccc tgctccccgc | 1500 |
| cacgggggcc gcatctgcgt gggcaagagc cgggaggaac ggttctgtaa tgagaacacg | 1560 |
| ccttgcccgg tgcccatctt ctgggcttcc tggggctcct ggagcaagtg cagcagcaac | 1620 |
| tgtggagggg gcatgcagtc gcggcgtcgg gcctgcgaga acggcaactc ctgcctgggc | 1680 |
| tgcggcgtgg agttcaagac gtgcaacccc gagggctgcc ccgaagtgcg cgcaacacc | 1740 |
| ccctggacgc cgtggctgcc cgtgaacgtg acgcagggcg gggcacggca ggagcagcgg | 1800 |
| ttccgcttca cctgccgcgc ccccttgca gacccgcacg gcctgcagtt cggcaggaga | 1860 |
| aggaccgaga cgaggacctg tcccgcgac ggctccggct cctgcgacac cgacgccctg | 1920 |
| gtggaggacc tcctgcgcag cgggagcacc tccccgcaca cggtgagcgg ggctgggcc | 1980 |
| gcctggggc cgtggtcgtc ctgctcccgg gactgcgagc tgggcttccg cgtccgcaag | 2040 |
| agaacgtgca ctaacccgga gccccgcaac gggggcctgc cctgcgtggg cgatgctgcc | 2100 |
| gagtaccagg actgcaaccc ccaggcttgc ccagttcggg gtgcttggtc ctgctggacc | 2160 |
| tcatggtctc catgctcagc ttcctgtggt ggggtcact atcaacgcac ccgttcctgc | 2220 |
| accagccccg caccctcccc aggtgaggac atctgtctcg gctgcacac ggaggaggca | 2280 |
| ctatgtgcca cacaggcctg cccagaaggc tggtcgccct ggtctgagtg gagtaagtgc | 2340 |
| actgacgacg gagcccagag ccgaagccgg cactgtgagg agctcctccc agggtccagc | 2400 |
| gcctgtgctg gaaacagcag ccagagccgc ccctgcccct acagcgagat tcccgggttc | 2460 |
| aatctcatcc acttggtggc cacgggcatc tcctgcttct gggctctgg gctcctgacc | 2520 |
| ctagcagtgt acctgtcttg ccagcactgc cagcgtcagt cccaggagtc cacactggtc | 2580 |
| catcctgcca cccccaacca tttgcactac aagggcggag gcaccccgaa gaatgaaaag | 2640 |

```
tacacaccca tggaattcaa gaccctgaac aagaataact tgatccctga tgacagagcc    2700
aacttctacc cattgcagca gaccaatgtg tacgacta cttactaccc aagcccctg       2760 aacaaacaca gcttccggcc cgaggcctca cctggacaac ggtgcttccc caacagctga   2820
```

```
<210> SEQ ID NO 16
<211> LENGTH: 939
<212> TYPE: PRT
<213> ORGANISM: homo sapiens

<400> SEQUENCE: 16
```

```
Met Cys Gly Thr Asn Ala Phe Ser Pro Met Cys Thr Ser Arg Gln Val
  1               5                  10                  15

Gly Asn Leu Ser Arg Thr Ile Glu Lys Ile Asn Gly Val Ala Arg Cys
             20                  25                  30

Pro Tyr Asp Pro Arg His Asn Ser Thr Ala Val Ile Ser Ser Gln Gly
         35                  40                  45

Glu Leu Tyr Ala Ala Thr Val Ile Asp Phe Ser Gly Arg Asp Pro Ala
     50                  55                  60

Ile Tyr Arg Ser Leu Gly Ser Gly Pro Pro Leu Arg Thr Ala Gln Tyr
 65                  70                  75                  80

Asn Ser Lys Trp Leu Asn Glu Pro Asn Phe Val Ala Ala Tyr Asp Ile
                 85                  90                  95

Gly Leu Phe Ala Tyr Phe Phe Leu Arg Glu Asn Ala Val Glu His Asp
            100                 105                 110

Cys Gly Arg Thr Val Tyr Ser Arg Val Ala Arg Val Cys Lys Asn Asp
        115                 120                 125

Val Gly Gly Arg Phe Leu Leu Glu Asp Thr Trp Thr Thr Phe Met Lys
    130                 135                 140

Ala Arg Leu Asn Cys Ser Arg Pro Gly Glu Val Pro Phe Tyr Tyr Asn
145                 150                 155                 160

Glu Leu Gln Ser Ala Phe His Leu Pro Glu Gln Asp Leu Ile Tyr Gly
                165                 170                 175

Val Phe Thr Thr Asn Val Asn Ser Ile Ala Ala Ser Ala Val Cys Ala
            180                 185                 190

Phe Asn Leu Ser Ala Ile Ser Gln Ala Phe Asn Gly Pro Phe Arg Tyr
        195                 200                 205

Gln Glu Asn Pro Arg Ala Ala Trp Leu Pro Ile Ala Asn Pro Ile Pro
    210                 215                 220

Asn Phe Gln Cys Gly Thr Leu Pro Glu Thr Gly Pro Asn Glu Asn Leu
225                 230                 235                 240

Thr Glu Arg Ser Leu Gln Asp Ala Gln Arg Leu Phe Leu Met Ser Glu
                245                 250                 255

Ala Val Gln Pro Val Thr Pro Glu Pro Cys Val Thr Gln Asp Ser Val
            260                 265                 270

Arg Phe Ser His Leu Val Val Asp Leu Val Gln Ala Lys Asp Thr Leu
        275                 280                 285

Tyr His Val Leu Tyr Ile Gly Thr Glu Ser Gly Thr Ile Leu Lys Ala
    290                 295                 300

Leu Ser Thr Ala Ser Arg Ser Leu His Gly Cys Tyr Leu Glu Glu Leu
305                 310                 315                 320

His Val Leu Pro Pro Gly Arg Arg Glu Pro Leu Arg Ser Leu Arg Ile
                325                 330                 335

Leu His Ser Ala Arg Ala Leu Phe Val Gly Leu Arg Asp Gly Val Leu
```

-continued

```
            340                 345                 350
Arg Val Pro Leu Glu Arg Cys Ala Ala Tyr Arg Ser Gln Gly Ala Cys
            355                 360                 365
Leu Gly Ala Arg Asp Pro Tyr Cys Gly Trp Asp Gly Lys Gln Gln Arg
            370                 375                 380
Cys Ser Thr Leu Glu Asp Ser Ser Asn Met Ser Leu Trp Thr Gln Asn
385                 390                 395                 400
Ile Thr Ala Cys Pro Val Arg Asn Val Thr Arg Asp Gly Gly Phe Gly
            405                 410                 415
Pro Trp Ser Pro Trp Gln Pro Cys Glu His Leu Asp Gly Asp Asn Ser
            420                 425                 430
Gly Ser Cys Leu Cys Arg Ala Arg Ser Cys Asp Ser Pro Arg Pro Arg
            435                 440                 445
Cys Gly Gly Leu Asp Cys Leu Gly Pro Ala Ile His Ile Ala Asn Cys
            450                 455                 460
Ser Arg Asn Gly Ala Trp Thr Pro Trp Ser Ser Trp Ala Leu Cys Ser
465                 470                 475                 480
Thr Ser Cys Gly Ile Gly Phe Gln Val Arg Gln Arg Ser Cys Ser Asn
            485                 490                 495
Pro Ala Pro Arg His Gly Gly Arg Ile Cys Val Gly Lys Ser Arg Glu
            500                 505                 510
Glu Arg Phe Cys Asn Glu Asn Thr Pro Cys Pro Val Pro Ile Phe Trp
            515                 520                 525
Ala Ser Trp Gly Ser Trp Ser Lys Cys Ser Ser Asn Cys Gly Gly Gly
            530                 535                 540
Met Gln Ser Arg Arg Ala Cys Glu Asn Gly Asn Ser Cys Leu Gly
545                 550                 555                 560
Cys Gly Val Glu Phe Lys Thr Cys Asn Pro Glu Gly Cys Pro Glu Val
            565                 570                 575
Arg Arg Asn Thr Pro Trp Thr Pro Trp Leu Pro Val Asn Val Thr Gln
            580                 585                 590
Gly Gly Ala Arg Gln Glu Gln Arg Phe Arg Phe Thr Cys Arg Ala Pro
            595                 600                 605
Leu Ala Asp Pro His Gly Leu Gln Phe Gly Arg Arg Thr Glu Thr
            610                 615                 620
Arg Thr Cys Pro Ala Asp Gly Ser Gly Ser Cys Asp Thr Asp Ala Leu
625                 630                 635                 640
Val Glu Asp Leu Leu Arg Ser Gly Ser Thr Ser Pro His Thr Val Ser
            645                 650                 655
Gly Gly Trp Ala Ala Trp Gly Pro Trp Ser Ser Cys Ser Arg Asp Cys
            660                 665                 670
Glu Leu Gly Phe Arg Val Arg Lys Arg Thr Cys Thr Asn Pro Glu Pro
            675                 680                 685
Arg Asn Gly Gly Leu Pro Cys Val Gly Asp Ala Ala Glu Tyr Gln Asp
            690                 695                 700
Cys Asn Pro Gln Ala Cys Pro Val Arg Gly Ala Trp Ser Cys Trp Thr
705                 710                 715                 720
Ser Trp Ser Pro Cys Ser Ala Ser Cys Gly Gly Gly His Tyr Gln Arg
            725                 730                 735
Thr Arg Ser Cys Thr Ser Pro Ala Pro Ser Pro Gly Glu Asp Ile Cys
            740                 745                 750
Leu Gly Leu His Thr Glu Glu Ala Leu Cys Ala Thr Gln Ala Cys Pro
            755                 760                 765
```

-continued

```
Glu Gly Trp Ser Pro Trp Ser Glu Trp Ser Lys Cys Thr Asp Asp Gly
         770                 775                 780

Ala Gln Ser Arg Ser Arg His Cys Glu Glu Leu Leu Pro Gly Ser Ser
785                 790                 795                 800

Ala Cys Ala Gly Asn Ser Ser Gln Ser Arg Pro Cys Pro Tyr Ser Glu
             805                 810                 815

Ile Pro Gly Phe Asn Leu Ile His Leu Val Ala Thr Gly Ile Ser Cys
             820                 825                 830

Phe Leu Gly Ser Gly Leu Leu Thr Leu Ala Val Tyr Leu Ser Cys Gln
         835                 840                 845

His Cys Gln Arg Gln Ser Gln Glu Ser Thr Leu Val His Pro Ala Thr
         850                 855                 860

Pro Asn His Leu His Tyr Lys Gly Gly Gly Thr Pro Lys Asn Glu Lys
865                 870                 875                 880

Tyr Thr Pro Met Glu Phe Lys Thr Leu Asn Lys Asn Asn Leu Ile Pro
                 885                 890                 895

Asp Asp Arg Ala Asn Phe Tyr Pro Leu Gln Gln Thr Asn Val Tyr Thr
             900                 905                 910

Thr Thr Tyr Tyr Pro Ser Pro Leu Asn Lys His Ser Phe Arg Pro Glu
         915                 920                 925

Ala Ser Pro Gly Gln Arg Cys Phe Pro Asn Ser
930                 935
```

<210> SEQ ID NO 17
<211> LENGTH: 4074
<212> TYPE: DNA
<213> ORGANISM: homo sapiens

<400> SEQUENCE: 17

```
cccgcggtct cctcctccct gctctctccg agcgccgggt cgggagctag ttggagcgcg      60
ggggttggtg ccagagccca gctccgccga gccgggcggg tcggcagcgc atccagcggc     120
tgctgggagc ccgagcgcag cgggcgcggg cccggtgggg gactgcaccg gagcgctgag     180
agctggaggc cgttcctgcg cggccgcccc attcccagac cggccgccag cccatctggt     240
tagctcccgc cgctccgcgc cgcccgggag tcgggagccg cggggaaccg ggcacctgca     300
cccgcctctg ggaggtcttc tcccctgtct gcctcccgga gctaggactg cagaggggcc     360
tatcatggtg cttgcaggcc cctggctgt ctcgctgttg ctgcccagcc tcacactgct      420
ggtgtcccac ctctccagct cccaggatgt ctccagtgag cccagcagtg agcagcagct     480
gtgcgccctt agcaagcacc ccaccgtggc ctttgaagac ctgcagccgt gggtctctaa     540
cttcacctac cctggagccc gggatttctc ccagctggct ttggaccct ccgggracca      600
gctcatcgtg ggagccagga actacctctt cagactcagc cttgccaatg tctctcttct     660
tcaggccaca gagtgggcct ccagtgagga cacgcgccgc tcctgccaaa gcaaagggaa     720
gactgaggag gagtgtcaga actacgtgcg agtcctgatc gtcgccggcc ggaaggtgtt     780
catgtgtgga accaatgcct tttcccccat gtgcaccagc agacaggtgg ggaacctcag     840
ccggactatt gagaagatca atggtgtggc ccgctgcccc tatgacccac gccacaactc     900
cacagctgtc atctcctccc aggggagct ctatgcagcc acggtcatcg acttctcagg     960
tcgggaccct gccatctacc gcagcctggg cagtgggcca ccgcttcgca ctgcccaata    1020
taactccaag tggcttaatg agccaaactt cgtggcagcc tatgatattg gctgtttgc     1080
atacttcttc ctgcgggaga acgcagtgga gcacgactgt ggacgcaccg tgtactctcg    1140
```

```
cgtggcccgc gtgtgcaaga atgacgtggg gggccgattc ctgctggagg acacatggac   1200
cacattcatg aaggcccggc tcaactgctc ccgcccgggc gaggtcccct tctactataa   1260
cgagctgcag agtgccttcc acttgccrga gcaggacctc atctatggag ttttcacaac   1320
caacgtaaac agcatygcgg cttctgctgt ctgcgccttc aacctcagtg ctatctccca   1380
ggctttcaat ggcccatttc gctaccagga gaaccccagg gctgcctggc tccccatagc   1440 caacccatc cccaatttcc agtgtggcac cctgcctgag accggtccca acgagaacct   1500
gacggagcgc agcctgcagg acgcgcagcg cctcttcctg atgagcgagg ccgtgcagcc   1560
ggtgacaccc gagccctgtg tcacccagga cagcgtgcgc ttctcacacc tcgtggtgga   1620
cctggtgcag gctaaagaca cgctctacca tgtactctac attggcaccg agtcgggcac   1680
catcctgaag gcgctgtcca cggcgagccg cagcctccac ggctgctacc tggaggagct   1740
gcacgtgctg cccccccggc gccgcgagcc cctgcgcagc ctgcgcatcc tgcacagcgc   1800
ccgcgcgctc ttcgtggggc tgagagacgg cgtcctgcgg gtcccactgg agaggtgcgc   1860
cgcctaccgc agccaggggg catgcctggg ggcccggac ccgtactgtg ctgggacgg   1920 gaagcagcaa cgttgcagca cactcgagga cagctccaac atgagcctct ggacccagaa   1980
catcaccgcc tgtcctgtgc ggaatgtgac acgggatggg ggcttcggcc catggtcacc   2040
atggcaacca tgtgagcact tggatgggga caactcaggc tcttgcctgt gtcgagctcg   2100
atcctgtgat tcccctcgac cccgctgtgg gggccttgac tgcctggggc cagccatcca   2160
catcgccaac tgctccagga atggggcgtg gaccccgtgg tcatcgtggg cgctgtgcag   2220
cacgtcctgt ggcatcggct tccaggtccg ccagcgaagt tgcagcaacc ctgctccccg   2280 ccacggggc cgcatctgcg tgggcaagag ccgggaggaa cggttctgta atgagaacac   2340
gccttgcccg gtgcccatct tctgggcttc ctggggctcc tggagcaagt gcagcagcaa   2400
ctgtggaggg ggcatgcagt cgcggcgtcg ggcctgcgag aacggcaact cctgcctggg   2460
ctgcggcgtg gagttcaaga cgtgcaaccc cgagggctgc cccgaagtgc ggcgcaacac   2520
cccctggacg ccgtggctgc ccgtgaacgt gacgcagggc ggggcacggc aggagcagcg   2580
gttccgcttc acctgccgcg cgcccccttgc agacccgcac ggcctgcagt tcggcaggag   2640
aaggaccgag acgaggacct gtcccgcgga cggctccggc tcctgcgaca ccgacgccct   2700
ggtggaggac ctcctgcgca gcgggagcac ctccccgcac acggtgagcg ggggctgggc   2760
cgcctggggc ccgtggtcgt cctgctcccg ggactgcgag ctgggcttcc gcgtccgcaa   2820
gagaacgtgc actaacccgg agcccgcaa cggggggcctg ccctgcgtgg gcgatgctgc   2880
cgagtaccag gactgcaacc cccaggcttg cccagttcgg ggtgcttggt cctgctggac   2940
ctcatggtct ccatgctcag cttcctgtgg tggggtcac tatcaacgca cccgttcctg   3000
caccagcccc gcaccctccc caggtgagga catctgtctc gggctgcaca cggaggaggc   3060
actatgtgcc acacaggcct gcccagaagg ctggtcgccc tggtctgagt ggagtaagtg   3120
cactgacgac ggagcccaga gccgaagccg gcactgtgag gagctcctcc cagggtccag   3180
cgcctgtgct ggaaacagca gccagagccg ccctgcccc tacagcgaga ttcccgtcat   3240
cctgccagcc tccagcatgg aggaggccac cggctgtgca gggttcaatc tcatccactt   3300
ggtggccacg ggcatctcct gcttcttggg ctctgggctc ctgaccctag cagtgtacct   3360
gtcttgccag cactgccagc gtcagtccca ggagtccaca ctggtccatc ctgccacccc   3420
caaccatttg cactacaagg gcggaggcac cccgaagaat gaaaagtaca cacccatgga   3480
```

```
attcaagacc ctgaacaaga ataacttgat ccctgatgac agagccaact tctacccatt   3540
gcagcagacc aatgtgtaca cgactactta ctacccaagc cccctgaaca acacagctt    3600 ccggcccgag gcctcacctg gacaacggtg cttccccaac agctgatacc gccgtcctgg   3660
ggacttgggc ttcttgcctt cataaggcac agagcagatg gagatgggac agtggagcca   3720
gtttggtttt ctccctctgc actaggccaa gaacttgctg ccttgcctgt gggggtccc    3780 atccggcttc agagagctct ggctggcatt gaccatgggg gaaagggctg gtttcaggct   3840
gacatatggc cgcaggtcca gttcagccca ggtctctcat ggttatcttc caacccactg   3900
tcacgctgac actatgctgc catgcctggg ctgtggacct actgggcatt tgaggaattg   3960
gagaatggag atggcaagag ggcaggcttt taagtttggg ttggagacaa cttcctgtgg   4020
cccccacaag ctgagtctgg ccttctccag ctggccccaa aaaaggcctt tgct         4074

<210> SEQ ID NO 18
<211> LENGTH: 648
<212> TYPE: DNA
<213> ORGANISM: homo sapiens

<400> SEQUENCE: 18 atgtgggga ggctctggcc cctcctcctc agcatcctca cagcaactgc agtcccagga    60
ccctcactgc ggagaccgtc tagagaacta gatgccaccc ctcggatgac catacccta   120 gaagagctct ctgggacccg gcacttcaag ggccaagccc agaactactc aacactgctg   180
ctggaggagg cctcagcaag gctgctggtg ggagcccgag gtgccctgtt ctctctcagt   240
gccaacgaca taggagatgg ggctcacaaa gagatccact gggaagcctc cccagagatg   300
caaagcaaat gtcatcaaaa agggaaaaac aaccagacgg agtgctttaa ccatgtgcgg   360
ttcctgcagc ggctcaattc tacccacctc tatgcatgtg ggactcacgc cttccagccc   420
ctctgtgcag ccattgatgc tgaggccttc accttgccaa ccagcttcga ggaggggaag   480
gagaagtgtc cttatgaccc agcccgtggc ttcacaggcc tcatcattga tggaggcctc   540
tacacagcca ctaggtatga attccggagc attcctgaca tccgccggag ccgccaccca   600
cactccctga gaactgagga gacaccaatg cattggctca atggttag               648

<210> SEQ ID NO 19
<211> LENGTH: 215
<212> TYPE: PRT
<213> ORGANISM: homo sapiens

<400> SEQUENCE: 19

Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110
```

```
Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
                180                 185                 190

Asp Ile Arg Arg Ser Arg His Pro His Ser Leu Arg Thr Glu Glu Thr
            195                 200                 205

Pro Met His Trp Leu Asn Gly
    210                 215

<210> SEQ ID NO 20
<211> LENGTH: 1491
<212> TYPE: DNA
<213> ORGANISM: homo sapiens

<400> SEQUENCE: 20 atgtgggga ggctctggcc cctcctcctc agcatcctca cagcaactgc agtcccagga      60
ccctcactgc ggagaccgtc tagagaacta gatgccaccc tcggatgac catacccctat   120
gaagagctct ctgggacccg gcacttcaag ggccaagccc agaactactc aacactgctg    180
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggaggggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga aactgaggga cacccaatg cattggctca atgatgcgga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt ctttgcagga ccctatatgg aataccagga tggttcccgg   1080
cgctggggtc gctatgaggg tggggtgcct gagccccggc ctggctcgtg tatcacagat   1140
tcattgcgca gccaaggcta caattcatcc caagacttgc catccctggt cctggacttt   1200
gtaaagttgc acccactgat ggctcggccc gttgtgccca cgtggacg gcccctgctg   1260
ctcaagcgca acatacgcta cacacacctt acagggacac tgtcaccac gcctgctgga   1320
cctacctatg acctgctctct tctgggcaca gctgatggct ggatccacaa ggccgtagtc   1380
ctgggctctg ggatgcacat tattgaagag acacaagtgt tcaggagtc ccagtctgtg   1440
gaaaatctag tcatctctct attgcaggta gcccttctct gtgacccta a              1491
```

```
<210> SEQ ID NO 21
<211> LENGTH: 496
<212> TYPE: PRT
<213> ORGANISM: homo sapiens

<400> SEQUENCE: 21

Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Arg Trp Gly Arg Tyr Glu Gly Gly
        355                 360                 365

Val Pro Glu Pro Arg Pro Gly Ser Cys Ile Thr Asp Ser Leu Arg Ser
    370                 375                 380
```

-continued

```
Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
            405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln Val Ala Leu Leu Cys Asp Pro
                485                 490                 495
```

<210> SEQ ID NO 22
<211> LENGTH: 2109
<212> TYPE: DNA
<213> ORGANISM: homo sapiens

<400> SEQUENCE: 22

```
atgtggggga ggctctggcc cctcctcctc agcatcctca cagcaactgc agtcccagga      60
ccctcactgc ggagaccgtc tagagaacta gatgccaccc tcggatgaca catacccctat    120
gaagagctct ctgggacccg gcacttcaag ggccaagccc agaactactc aacactgctg    180
ctggaggagg cctcagcaag gctgctggtg ggagcccgag gtgccctgtt ctctctcagt    240
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccactc tatgcatgtg ggactcacgc cttccagccc     420
ctctgtgcag ccattgatgc tgaggccttc accttgccaa ccagcttcga ggaggggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga gaactgagga gacaccaatg cattggctca atgatgcgga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt cttcgcagga ccctatatgg aataccagga tggttcccgg   1080
cgctggggtc gctatgaggg tggggtgcct gagccccggc ctggctcgtg tatcacagat   1140
tcattgcgca gccaaggcta caattcatcc aagacttgc catccctggt cctggacttt   1200
gtaaagttgc acccactgat ggctcggccc gttgtgccca cacgtggacg gcccctgctg   1260
ctcaagcgca acatacgcta cacacacctt acagggacac ctgtcaccac gcctgctgga   1320
cctacctatg acctgctctt tctgggcaca gctgatggct ggatccacaa ggccgtagtc   1380
ctgggctctg ggatgcacat tattgaagag acacaagtgt tcagggagtc ccagtctgtg   1440
gaaaatctag tcatctctct attgcagcac agcctctatg tggggctcc  tagcggagtc    1500
```

```
atccagctac cactctccag ctgctcccgc taccgatcct gctatgactg catcttggcc    1560
cgagacccct actgtggctg ggaccctggc acccatgcct gcgcagcagc caccaccata    1620
gccaacaggt cccagggaag caggacagca ctgatacagg acatagagag aggaaatcga    1680
ggctgtgaga gcagcaggga tacaggcagg gctctgcagg tccatatggg ctcaatgtca    1740
ccaccctctg catggccctg tgtgctggat ggtcctgaaa ccagacaagt cctctgccag    1800
ccacctaagc cctgcgtaca ttcacatgca cacatggaag aatgtttatc ggctgggctg    1860
cagtgccccc accctcacct ctcctggtg cattcttgtt tcatccctgc ttctggactt    1920
ggggtaccct cccaattgcc acatcctatc tggtcctctt ccccagcccc atgtggtgac    1980
ctctttgtca agagcttggg aacgggccag cctggggagg taagactgca tcactcccct    2040
cctctccctt cctgtgtggc ccttgtgaat cagcctcccc actctccttg gtcattctca    2100
agagtatga                                                            2109
```

<210> SEQ ID NO 23
<211> LENGTH: 702
<212> TYPE: PRT
<213> ORGANISM: homo sapiens

<400> SEQUENCE: 23

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255
```

-continued

```
Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
            275                 280                 285

Lys Ala Arg Leu Ile Cys His Ile Pro Leu Tyr Glu Thr Leu Arg Gly
            290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                    325                 330                 335

Cys Arg Tyr Asp Leu Ala Glu Ile Gln Ala Val Phe Ala Gly Pro Tyr
                340                 345                 350

Met Glu Tyr Gln Asp Gly Ser Arg Arg Trp Gly Arg Tyr Glu Gly Gly
            355                 360                 365

Val Pro Glu Pro Arg Pro Gly Ser Cys Ile Thr Asp Ser Leu Arg Ser
370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Val Leu Gly Ser Gly
        450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
            515                 520                 525

Pro Gly Thr His Ala Cys Ala Ala Thr Thr Ile Ala Asn Arg Ser
            530                 535                 540

Gln Gly Ser Arg Thr Ala Leu Ile Gln Asp Ile Glu Arg Gly Asn Arg
545                 550                 555                 560

Gly Cys Glu Ser Ser Arg Asp Thr Gly Arg Ala Leu Gln Val His Met
                565                 570                 575

Gly Ser Met Ser Pro Pro Ser Ala Trp Pro Cys Val Leu Asp Gly Pro
            580                 585                 590

Glu Thr Arg Gln Val Leu Cys Gln Pro Pro Lys Pro Cys Val His Ser
            595                 600                 605

His Ala His Met Glu Glu Cys Leu Ser Ala Gly Leu Gln Cys Pro His
            610                 615                 620

Pro His Leu Leu Leu Val His Ser Cys Phe Ile Pro Ala Ser Gly Leu
625                 630                 635                 640

Gly Val Pro Ser Gln Leu Pro His Pro Ile Trp Ser Ser Ser Pro Ala
                645                 650                 655

Pro Cys Gly Asp Leu Phe Val Lys Ser Leu Gly Thr Gly Gln Pro Gly
            660                 665                 670

Glu Val Arg Leu His His Ser Pro Pro Leu Pro Ser Cys Val Ala Leu
```

675                 680                 685
Val Asn Gln Pro Pro His Ser Pro Trp Ser Phe Ser Arg Val
            690                 695                 700

<210> SEQ ID NO 24
<211> LENGTH: 2094
<212> TYPE: DNA
<213> ORGANISM: homo sapiens

<400> SEQUENCE: 24

| | | | | | |
|---|---|---|---|---|---|
| atgtggggga | ggctctggcc | cctcctcctc | agcatcctca | cagcaactgc | agtcccagga | 60 |
| ccctcactgc | ggagaccgtc | tagagaacta | gatgccaccc | ctcggatgac | catacccctat | 120 |
| gaagagctct | ctgggacccg | gcacttcaag | ggccaagccc | agaactactc | aacactgctg | 180 |
| ctggaggagg | cctcagcaag | gctgctggtg | ggagcccgag | gtgccctgtt | ctctctcagt | 240 |
| gccaacgaca | taggagatgg | ggctcacaaa | gagatccact | gggaagcctc | cccagagatg | 300 |
| caaagcaaat | gtcatcaaaa | aggaaaaac | aaccagacgg | agtgctttaa | ccatgtgcgg | 360 |
| ttcctgcagc | ggctcaattc | tacccacctc | tatgcatgtg | ggactcacgc | cttccagccc | 420 |
| ctctgtgcag | ccattgatgc | tgaggccttc | accttgccaa | ccagcttcga | ggaggggaag | 480 |
| gagaagtgtc | cttatgaccc | agcccgtggc | ttcacaggcc | tcatcattga | tggaggcctc | 540 |
| tacacagcca | ctaggtatga | attccggagc | attcctgaca | tccgccggag | ccgccaccca | 600 |
| cactccctga | aactgagga | gacaccaatg | cattggctca | atgatgcgga | gtttgtgttc | 660 |
| tccgtcctcg | tgcgggagag | caaggccagt | gcagtgggtg | atgatgacaa | ggtgtactac | 720 |
| ttcttcacgg | agcgtgccac | tgaggagggc | tctggcagct | tcactcagag | ccgcagcagt | 780 |
| caccgtgtgg | cccgtgtggc | tcgygtctgc | aagggagacc | tgggagggaa | gaagatcctg | 840 |
| cagaagaagt | ggacttcctt | cctgaaagcc | cgtctcatct | gccacattcc | actgtatgag | 900 |
| acactgcgtg | gggtctgcag | cctggatgct | gaaacctcaa | gccgtacaca | cttctatgca | 960 |
| gccttcacgc | tgagcacaca | gtggaagacc | ctggaggcct | cagccatctg | ccgctatgac | 1020 |
| ctggcagaga | tccaggctgt | cttttgcagga | ccctatatgg | aataccagga | tggttcccgg | 1080 |
| cgctgggtc | gctatgaggg | tggggtgcct | gagccccggc | ctggctcgtg | tatcacagat | 1140 |
| tcattgcgca | gccaaggcta | caattcatcc | caagacttgc | catccctggt | cctggacttt | 1200 |
| gtaaagttgc | acccactgat | ggctcggccc | gttgtgccca | cacgtggacg | gcccctgctg | 1260 |
| ctcaagcgca | acatacgcta | cacacacctt | acagggacac | ctgtcaccac | gcctgctgga | 1320 |
| cctaccctatg | acctgctctt | tctgggcaca | gctgatggct | ggatccacaa | ggccgtagtc | 1380 |
| ctgggctctg | ggatgcacat | tattgaagag | acacaagtgt | tcagggagtc | ccagtctgtg | 1440 |
| gaaaatctag | tcatctctct | attgcagcac | agcctctatg | tggggctcc | tagcggagtc | 1500 |
| atccagctac | cactctccag | ctgctcccgc | taccgatcct | gctatgactg | catcttggcc | 1560 |
| cgagacccct | actgtggctg | ggaccctggc | acccatgcct | gcgcagcagc | caccaccata | 1620 |
| gccaacagga | cagcactgat | acaggacata | gagagaggaa | atcgaggctg | tgagagcagc | 1680 |
| agggatacag | gcagggctct | gcaggtccat | atgggctcaa | tgtcaccacc | ctctgcatgg | 1740 |
| ccctgtgtgc | tggatggtcc | tgaaaccaga | caagtcctct | gccagccacc | taagccctgc | 1800 |
| gtacattcac | atgcacacat | ggaagaatgt | ttatcggctg | ggctgcagtg | cccccaccct | 1860 |
| caccttctcc | tggtgcattc | ttgtttcatc | cctgcttctg | gacttggggt | accctcccaa | 1920 |
| ttgccacatc | ctatctggtc | ctcttcccca | gccccatgtg | gtgacctctt | tgtcaagagc | 1980 |

-continued

```
ttgggaacgg gccagcctgg ggaggtaaga ctgcatcact cccctcctct cccttcctgt    2040
gtggcccttg tgaatcagcc tccccactct ccttggtcat tctcaagagt atga          2094
```

<210> SEQ ID NO 25
<211> LENGTH: 697
<212> TYPE: PRT
<213> ORGANISM: homo sapiens

<400> SEQUENCE: 25

```
Met Trp Gly Arg Leu Trp Pro Leu Leu Leu Ser Ile Leu Thr Ala Thr
 1               5                  10                  15

Ala Val Pro Gly Pro Ser Leu Arg Arg Pro Ser Arg Glu Leu Asp Ala
             20                  25                  30

Thr Pro Arg Met Thr Ile Pro Tyr Glu Glu Leu Ser Gly Thr Arg His
         35                  40                  45

Phe Lys Gly Gln Ala Gln Asn Tyr Ser Thr Leu Leu Leu Glu Glu Ala
     50                  55                  60

Ser Ala Arg Leu Leu Val Gly Ala Arg Gly Ala Leu Phe Ser Leu Ser
 65                  70                  75                  80

Ala Asn Asp Ile Gly Asp Gly Ala His Lys Glu Ile His Trp Glu Ala
                 85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Arg Trp Gly Arg Tyr Glu Gly Gly
```

-continued

```
                355                 360                 365
Val Pro Glu Pro Arg Pro Gly Ser Cys Ile Thr Asp Ser Leu Arg Ser
    370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
        435                 440                 445

Gly Thr Ala Asp Gly Trp Ile His Lys Ala Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
        515                 520                 525

Pro Gly Thr His Ala Cys Ala Ala Ala Thr Thr Ile Ala Asn Arg Thr
    530                 535                 540

Ala Leu Ile Gln Asp Ile Glu Arg Gly Asn Arg Gly Cys Glu Ser Ser
545                 550                 555                 560

Arg Asp Thr Gly Arg Ala Leu Gln Val His Met Gly Ser Met Ser Pro
                565                 570                 575

Pro Ser Ala Trp Pro Cys Val Leu Asp Gly Pro Glu Thr Arg Gln Val
            580                 585                 590

Leu Cys Gln Pro Pro Lys Pro Cys Val His Ser His Ala His Met Glu
        595                 600                 605

Glu Cys Leu Ser Ala Gly Leu Gln Cys Pro His Pro His Leu Leu Leu
    610                 615                 620

Val His Ser Cys Phe Ile Pro Ala Ser Gly Leu Gly Val Pro Ser Gln
625                 630                 635                 640

Leu Pro His Pro Ile Trp Ser Ser Pro Ala Pro Cys Gly Asp Leu
                645                 650                 655

Phe Val Lys Ser Leu Gly Thr Gly Gln Pro Gly Glu Val Arg Leu His
            660                 665                 670

His Ser Pro Pro Leu Pro Ser Cys Val Ala Leu Val Asn Gln Pro Pro
        675                 680                 685

His Ser Pro Trp Ser Phe Ser Arg Val
    690                 695
```

<210> SEQ ID NO 26
<211> LENGTH: 2532
<212> TYPE: DNA
<213> ORGANISM: homo sapiens

<400> SEQUENCE: 26

```
atgtggggga ggctctggcc cctcctcctc agcatcctca cagcaactgc agtcccagga      60
ccctcactgc ggagaccgtc tagagaacta gatgccaccc tcggatgac catacccat     120 gaagagctct ctgggacccg gcacttcaag ggccaagccc agaactactc aacactgctg    180
```

-continued

| | |
|---|---|
| ctggaggagg cctcagcaag gctgctggtg ggagcccgag gtgccctgtt ctctctcagt | 240 |
| gccaacgaca taggagatgg ggctcacaaa gagatccact gggaagcctc cccagagatg | 300 |
| caaagcaaat gtcatcaaaa agggaaaaac aaccagacgg agtgctttaa ccatgtgcgg | 360 |
| ttcctgcagc ggctcaattc tacccacctc tatgcatgtg ggactcacgc cttccagccc | 420 |
| ctctgtgcag ccattgatgc tgaggccttc accttgccaa ccagcttcga ggaggggaag | 480 |
| gagaagtgtc cttatgaccc agcccgtggc ttcacaggcc tcatcattga tggaggcctc | 540 |
| tacacagcca ctaggtatga attccggagc attcctgaca tccgccggag ccgccaccca | 600 |
| cactccctga aactgaggga gacaccaatg cattggctca atgatgcgga gtttgtgttc | 660 |
| tccgtcctcg tgcgggagag caaggccagt gcagtgggtg atgatgacaa ggtgtactac | 720 |
| ttcttcacgg agcgtgccac tgaggagggc tctggcagct tcactcagag ccgcagcagt | 780 |
| caccgtgtgg cccgtgtggc tcgygtctgc aagggagacc tgggagggaa gaagatcctg | 840 |
| cagaagaagt ggacttcctt cctgaaagcc cgtctcatct gccacattcc actgtatgag | 900 |
| acactgcgtg gggtctgcag cctggatgct gaaacctcaa gccgtacaca cttctatgca | 960 |
| gccttcacgc tgagcacaca gtggaagacc ctggaggcct cagccatctg ccgctatgac | 1020 |
| ctggcagaga tccaggctgt ctttgcagga ccctatatgg aataccagga tggttcccgg | 1080 |
| cgctggggtc gctatgaggg tggggtgcct gagccccggc ctggctcgtg tatcacagat | 1140 |
| tcattgcgca gccaaggcta caattcatcc aagacttgc catccctggt cctggacttt | 1200 |
| gtaaagttgc acccactgat ggctcggccc gttgtgccca cacgtggacg gcccctgctg | 1260 |
| ctcaagcgca acatacgcta cacacacctt acagggacac ctgtcaccac gcctgctgga | 1320 |
| cctacctatg acctgctctt tctgggcaca gctgatggct ggatccacaa ggccgtagtc | 1380 |
| ctgggctctg ggatgcacat tattgaagag acacaagtgt tcagggagtc ccagtctgtg | 1440 |
| gaaaatctag tcatctctct attgcagcac agcctctatg tggggctcc tagcggagtc | 1500 |
| atccagctac cactctccag ctgctcccgc taccgatcct gctatgactg catcttggcc | 1560 |
| cgagacccct actgtggctg ggaccctggc acccatgcct gcgcagcagc caccaccata | 1620 |
| gccaacaggt cccagggaag caggacagca ctgatacagg acatagagag aggaaatcga | 1680 |
| ggctgtgaga gcagcaggga tacagggcca ccaccaccac tgaagacccg ctctgtgctc | 1740 |
| cggggtgatg atgtcctcct gccctgtgac cagccatcca acctggcccg ggccttgtgg | 1800 |
| ctactcaatg ggagcatggg cctgagcgat gggcagggtg gctaccgtgt gggcgtggac | 1860 |
| gggctgctgg ttacagatgc acagcctgag cacagtggca actatggctg ctatgccgag | 1920 |
| gaaaatggcc tccgcaccct gctggcctcc tatagtctca cagtccggcc agccactcct | 1980 |
| gccccagctc caaaagcccc tgccacacct ggggcacagc tggcacctga tgtgagactg | 2040 |
| ctctatgtgc tagccattgc cgcgcttggt ggccyctgcc tcatcctggc ctcctccctc | 2100 |
| ctctatgtgg cctgtctgcg ggaaggcaga cgagggcgcc gacggaaata tcactgggt | 2160 |
| cgggccagcc gggcaggagg atctgcggtg caactgcaga cagtctcagg ccagtgtcct | 2220 |
| ggagaggaag atgagggtga tgatgagggg gctggggcc tggagggcag ctgtctccag | 2280 |
| atcatccctg ggagggagc cccagcccca ccaccccac cgcccccacc gccaccggct | 2340 |
| gagctgacca atggcttggt ggcactgccc agccggctgc ggaggatgaa tggcaatagc | 2400 |
| tatgtgcttc tgaggcagag caacaatgga gtaccagcag ggccctgctc cttcgccgag | 2460 |
| gaactcagcc gcatcctgga aaaaggaag cacacgcagc tcgtggagca gctagatgag | 2520 |
| agctctgtct ga | 2532 |

<210> SEQ ID NO 27
<211> LENGTH: 843
<212> TYPE: PRT
<213> ORGANISM: homo sapiens

<400> SEQUENCE: 27

```
Met Trp Gly Arg Leu Trp Pro Leu Leu Ser Ile Leu Thr Ala Thr
 1               5                  10                  15

Ala Val Pro Gly Pro Ser Leu Arg Arg Pro Ser Arg Glu Leu Asp Ala
                 20                  25                  30

Thr Pro Arg Met Thr Ile Pro Tyr Glu Glu Leu Ser Gly Thr Arg His
             35                  40                  45

Phe Lys Gly Gln Ala Gln Asn Tyr Ser Thr Leu Leu Leu Glu Glu Ala
 50                  55                  60

Ser Ala Arg Leu Leu Val Gly Ala Arg Gly Ala Leu Phe Ser Leu Ser
 65                  70                  75                  80

Ala Asn Asp Ile Gly Asp Gly Ala His Lys Glu Ile His Trp Glu Ala
                 85                  90                  95

Ser Pro Glu Met Gln Ser Lys Cys His Gln Lys Gly Lys Asn Asn Gln
                100                 105                 110

Thr Glu Cys Phe Asn His Val Arg Phe Leu Gln Arg Leu Asn Ser Thr
            115                 120                 125

His Leu Tyr Ala Cys Gly Thr His Ala Phe Gln Pro Leu Cys Ala Ala
130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
                180                 185                 190

Asp Ile Arg Arg Ser Arg His Pro His Ser Leu Arg Thr Glu Glu Thr
            195                 200                 205

Pro Met His Trp Leu Asn Asp Ala Glu Phe Val Phe Ser Val Leu Val
210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
                260                 265                 270

Asp Leu Gly Gly Lys Lys Ile Leu Gln Lys Lys Trp Thr Ser Phe Leu
            275                 280                 285

Lys Ala Arg Leu Ile Cys His Ile Pro Leu Tyr Glu Thr Leu Arg Gly
290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
                340                 345                 350

Met Glu Tyr Gln Asp Gly Ser Arg Arg Trp Gly Arg Tyr Glu Gly Gly
            355                 360                 365

Val Pro Glu Pro Arg Pro Gly Ser Cys Ile Thr Asp Ser Leu Arg Ser
```

-continued

```
            370                 375                 380
Gln Gly Tyr Asn Ser Ser Gln Asp Leu Pro Ser Leu Val Leu Asp Phe
385                 390                 395                 400
Val Lys Leu His Pro Leu Met Ala Arg Pro Val Pro Thr Arg Gly
                405                 410                 415
Arg Pro Leu Leu Leu Lys Arg Asn Ile Arg Tyr Thr His Leu Thr Gly
                420                 425                 430
Thr Pro Val Thr Thr Pro Ala Gly Pro Thr Tyr Asp Leu Leu Phe Leu
        435                 440                 445
Gly Thr Ala Asp Gly Trp Ile His Lys Ala Val Val Leu Gly Ser Gly
        450                 455                 460
Met His Ile Ile Glu Glu Thr Gln Val Phe Arg Glu Ser Gln Ser Val
465                 470                 475                 480
Glu Asn Leu Val Ile Ser Leu Leu Gln His Ser Leu Tyr Val Gly Ala
                485                 490                 495
Pro Ser Gly Val Ile Gln Leu Pro Leu Ser Ser Cys Ser Arg Tyr Arg
                500                 505                 510
Ser Cys Tyr Asp Cys Ile Leu Ala Arg Asp Pro Tyr Cys Gly Trp Asp
        515                 520                 525
Pro Gly Thr His Ala Cys Ala Ala Ala Thr Thr Ile Ala Asn Arg Ser
        530                 535                 540
Gln Gly Ser Arg Thr Ala Leu Ile Gln Asp Ile Glu Arg Gly Asn Arg
545                 550                 555                 560
Gly Cys Glu Ser Ser Arg Asp Thr Gly Pro Pro Pro Leu Lys Thr
                565                 570                 575
Arg Ser Val Leu Arg Gly Asp Val Leu Leu Pro Cys Asp Gln Pro
                580                 585                 590
Ser Asn Leu Ala Arg Ala Leu Trp Leu Leu Asn Gly Ser Met Gly Leu
        595                 600                 605
Ser Asp Gly Gln Gly Gly Tyr Arg Val Gly Val Asp Gly Leu Leu Val
        610                 615                 620
Thr Asp Ala Gln Pro Glu His Ser Gly Asn Tyr Gly Cys Tyr Ala Glu
625                 630                 635                 640
Glu Asn Gly Leu Arg Thr Leu Leu Ala Ser Tyr Ser Leu Thr Val Arg
                645                 650                 655
Pro Ala Thr Pro Ala Pro Ala Pro Lys Ala Pro Ala Thr Pro Gly Ala
                660                 665                 670
Gln Leu Ala Pro Asp Val Arg Leu Leu Tyr Val Leu Ala Ile Ala Ala
        675                 680                 685
Leu Gly Gly Leu Cys Leu Ile Leu Ala Ser Ser Leu Leu Tyr Val Ala
        690                 695                 700
Cys Leu Arg Glu Gly Arg Arg Gly Arg Arg Lys Tyr Ser Leu Gly
705                 710                 715                 720
Arg Ala Ser Arg Ala Gly Gly Ser Ala Val Gln Leu Gln Thr Val Ser
                725                 730                 735
Gly Gln Cys Pro Gly Glu Glu Asp Glu Gly Asp Asp Glu Gly Ala Gly
                740                 745                 750
Gly Leu Glu Gly Ser Cys Leu Gln Ile Ile Pro Gly Glu Gly Ala Pro
        755                 760                 765
Ala Pro Pro Pro Pro Pro Pro Pro Ala Glu Leu Thr Asn
        770                 775                 780
Gly Leu Val Ala Leu Pro Ser Arg Leu Arg Arg Met Asn Gly Asn Ser
785                 790                 795                 800
```

-continued

Tyr Val Leu Leu Arg Gln Ser Asn Asn Gly Val Pro Ala Gly Pro Cys
            805                 810                 815

Ser Phe Ala Glu Glu Leu Ser Arg Ile Leu Glu Lys Arg Lys His Thr
        820                 825                 830

Gln Leu Val Glu Gln Leu Asp Glu Ser Ser Val
        835                 840

<210> SEQ ID NO 28
<211> LENGTH: 2517
<212> TYPE: DNA
<213> ORGANISM: homo sapiens

<400> SEQUENCE: 28

| | | | | | |
|---|---|---|---|---|---|
| atgtgggga | ggctctggcc | cctcctcctc | agcatcctca | cagcaactgc | agtcccagga | 60 |
| ccctcactgc | ggagaccgtc | tagagaacta | gatgccaccc | ctcggatgac | catccctat | 120 |
| gaagagctct | ctgggacccg | gcacttcaag | ggccaagccc | agaactactc | aacactgctg | 180 |
| ctggaggagg | cctcagcaag | gctgctggtg | ggagcccgag | gtgccctgtt | ctctctcagt | 240 |
| gccaacgaca | taggagatgg | ggctcacaaa | gagatccact | gggaagcctc | cccagagatg | 300 |
| caaagcaaat | gtcatcaaaa | agggaaaaac | aaccagacgg | agtgctttaa | ccatgtgcgg | 360 |
| ttcctgcagc | ggctcaattc | tacccacctc | tatgcatgtg | ggactcacgc | cttccagccc | 420 |
| ctctgtgcag | ccattgatgc | tgaggccttc | accttgccaa | ccagcttcga | ggaggggaag | 480 |
| gagaagtgtc | cttatgaccc | agcccgtggc | ttcacaggcc | tcatcattga | tggaggcctc | 540 |
| tacacagcca | ctaggtatga | attccggagc | attcctgaca | tccgccggag | ccgccaccca | 600 |
| cactccctga | gaactgagga | gacaccaatg | cattggctca | atgatgcgga | gtttgtgttc | 660 |
| tccgtcctcg | tgcgggagag | caaggccagt | gcagtgggtg | atgatgacaa | ggtgtactac | 720 |
| ttcttcacgg | agcgtgccac | tgaggagggc | tctggcagct | tcactcagag | ccgcagcagt | 780 |
| caccgtgtgg | cccgtgtggc | tcgygtctgc | aagggagacc | tgggagggaa | gagatcctg | 840 |
| cagaagaagt | ggacttcctt | cctgaaagcc | cgtctcatct | gccacattcc | actgtatgag | 900 |
| acactgcgtg | gggtctgcag | cctggatgct | gaaacctcaa | gccgtacaca | cttctatgca | 960 |
| gccttcacgc | tgagcacaca | gtggaagacc | ctggaggcct | cagccatctg | ccgctatgac | 1020 |
| ctggcagaga | tccaggctgt | ctttgcagga | ccctatatgg | aataccagga | tggttcccgg | 1080 |
| cgctggggtc | gctatgaggg | tgggtgcct | gagccccggc | ctggctcgtg | tatcacagat | 1140 |
| tcattgcgca | gccaaggcta | caattcatcc | aagacttgc | catccctggt | cctggacttt | 1200 |
| gtaaagttgc | acccactgat | ggctcggccc | gttgtgccca | cacgtggacg | gcccctgctg | 1260 |
| ctcaagcgca | acatacgcta | cacacacctt | acagggacac | ctgtcaccac | gcctgctgga | 1320 |
| cctacctatg | acctgctctt | tctgggcaca | gctgatggct | ggatccacaa | ggccgtagtc | 1380 |
| ctgggctctg | ggatgcacat | tattgaagag | acacaagtgt | cagggagtc | ccagtctgtg | 1440 |
| gaaaatctag | tcatctctct | attgcagcac | agcctctatg | tggggctcc | tagcggagtc | 1500 |
| atccagctac | cactctccag | ctgctcccgc | taccgatcct | gctatgactg | catcttggcc | 1560 |
| cgagacccct | actgtggctg | ggaccctggc | acccatgcct | cgcagcagc | caccaccata | 1620 |
| gccaacagga | cagcactgat | acaggacata | gagagaggaa | atcgaggctg | tgagagcagc | 1680 |
| agggatacag | ggccaccacc | accactgaag | acccgctctg | tgctccgggg | tgatgatgtc | 1740 |
| ctcctgccct | gtgaccagcc | atccaacctg | gcccgggcct | tgtggctact | caatgggagc | 1800 |
| atgggcctga | gcgatgggca | gggtggctac | cgtgtgggcg | tggacgggct | gctggttaca | 1860 |

-continued

```
gatgcacagc ctgagcacag tggcaactat ggctgctatg ccgaggaaaa tggcctccgc   1920
accctgctgg cctcctatag tctcacagtc cggccagcca ctcctgcccc agctccaaaa   1980 gccctgcca cacctggggc acagctggca cctgatgtga gactgctcta tgtgctagcc    2040
attgccgcgc ttggtggccy ctgcctcatc ctggcctcct ccctcctcta tgtggcctgt   2100
ctgcgggaag gcagacgagg gcgccgacgg aaatactcac tgggtcgggc cagccgggca   2160
ggaggatctg cggtgcaact gcagacagtc tcaggccagt gtcctggaga ggaagatgag   2220
ggtgatgatg aggggggctgg gggcctggag ggcagctgtc tccagatcat ccctggggag   2280
ggagccccag ccccaccacc cccaccgccc ccaccgccac cggctgagct gaccaatggc   2340
ttggtggcac tgcccagccg gctgcggagg atgaatggca atagctatgt gcttctgagg   2400
cagagcaaca atggagtacc agcagggccc tgctccttcg ccgaggaact cagccgcatc   2460
ctggaaaaaa ggaagcacac gcagctcgtg gagcagctag atgagagctc tgtctga      2517
```

<210> SEQ ID NO 29
<211> LENGTH: 838
<212> TYPE: PRT
<213> ORGANISM: homo sapiens

<400> SEQUENCE: 29

```
Met Trp Gly Arg Leu Trp Pro Leu Leu Leu Ser Ile Leu Thr Ala Thr
  1               5                  10                  15

Ala Val Pro Gly Pro Ser Leu Arg Arg Pro Ser Arg Glu Leu Asp Ala
             20                  25                  30

Thr Pro Arg Met Thr Ile Pro Tyr Glu Glu Leu Ser Gly Thr Arg His
         35                  40                  45

Phe Lys Gly Gln Ala Gln Asn Tyr Ser Thr Leu Leu Leu Glu Glu Ala
     50                  55                  60

Ser Ala Arg Leu Leu Val Gly Ala Arg Gly Ala Leu Phe Ser Leu Ser
 65                  70                  75                  80

Ala Asn Asp Ile Gly Asp Gly Ala His Lys Glu Ile His Trp Glu Ala
                 85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Gly Ser Gly Ser Phe Thr Gln
                245                 250                 255
```

```
Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
            275                 280                 285

Lys Ala Arg Leu Ile Cys His Ile Pro Leu Tyr Glu Thr Leu Arg Gly
            290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
                340                 345                 350

Met Glu Tyr Gln Asp Gly Ser Arg Arg Trp Gly Arg Tyr Glu Gly Gly
                355                 360                 365

Val Pro Glu Pro Arg Pro Gly Ser Cys Ile Thr Asp Ser Leu Arg Ser
            370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Val Pro Thr Arg Gly
                405                 410                 415

Arg Pro Leu Leu Leu Lys Arg Asn Ile Arg Tyr Thr His Leu Thr Gly
                420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Val Leu Gly Ser Gly
450                 455                 460

Met His Ile Ile Glu Glu Thr Gln Val Phe Arg Glu Ser Gln Ser Val
465                 470                 475                 480
G
lu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
            515                 520                 525

Pro Gly Thr His Ala Cys Ala Ala Ala Thr Thr Ile Ala Asn Arg Thr
            530                 535                 540

Ala Leu Ile Gln Asp Ile Glu Arg Gly Asn Arg Gly Cys Glu Ser Ser
545                 550                 555                 560

Arg Asp Thr Gly Pro Pro Pro Leu Lys Thr Arg Ser Val Leu Arg
                565                 570                 575

Gly Asp Asp Val Leu Pro Cys Asp Gln Pro Ser Asn Leu Ala Arg
                580                 585                 590

Ala Leu Trp Leu Leu Asn Gly Ser Met Gly Leu Ser Asp Gly Gln Gly
                595                 600                 605

Gly Tyr Arg Val Gly Val Asp Gly Leu Leu Val Thr Asp Ala Gln Pro
            610                 615                 620

Glu His Ser Gly Asn Tyr Gly Cys Tyr Ala Glu Asn Gly Leu Arg
625                 630                 635                 640

Thr Leu Leu Ala Ser Tyr Ser Leu Thr Val Arg Pro Ala Thr Pro Ala
                645                 650                 655

Pro Ala Pro Lys Ala Pro Ala Thr Pro Gly Ala Gln Leu Ala Pro Asp
            660                 665                 670

Val Arg Leu Leu Tyr Val Leu Ala Ile Ala Ala Leu Gly Gly Leu Cys
```

-continued

```
              675                 680                 685
Leu Ile Leu Ala Ser Ser Leu Leu Tyr Val Ala Cys Leu Arg Glu Gly
        690                 695                 700
Arg Arg Gly Arg Arg Lys Tyr Ser Leu Gly Arg Ala Ser Arg Ala
705                 710                 715                 720
Gly Gly Ser Ala Val Gln Leu Gln Thr Val Ser Gly Gln Cys Pro Gly
                725                 730                 735
Glu Glu Asp Glu Gly Asp Asp Glu Gly Ala Gly Gly Leu Glu Gly Ser
                740                 745                 750
Cys Leu Gln Ile Ile Pro Gly Glu Gly Ala Pro Ala Pro Pro Pro
            755                 760                 765
Pro Pro Pro Pro Pro Pro Ala Glu Leu Thr Asn Gly Leu Val Ala Leu
    770                 775                 780
Pro Ser Arg Leu Arg Arg Met Asn Gly Asn Ser Tyr Val Leu Leu Arg
785                 790                 795                 800
Gln Ser Asn Asn Gly Val Pro Ala Gly Pro Cys Ser Phe Ala Glu Glu
                805                 810                 815
Leu Ser Arg Ile Leu Glu Lys Arg Lys His Thr Gln Leu Val Glu Gln
            820                 825                 830
Leu Asp Glu Ser Ser Val
        835
```

<210> SEQ ID NO 30
<211> LENGTH: 2613
<212> TYPE: DNA
<213> ORGANISM: homo sapiens

<400> SEQUENCE: 30

```
atgtggggga ggctctggcc cctcctcctc agcatcctca cagcaactgc agtcccagga      60
ccctcactgc ggagaccgtc tagagaacta gatgccaccc tcggatgac ataccctat      120
gaagagctct ctgggacccg gcacttcaag ggccaagccc agaactactc aacactgctg     180
ctggaggagg cctcagcaag gctgctggtg ggagcccgag gtgccctgtt ctctctcagt     240
gccaacgaca taggagatgg ggctcacaaa gagatccact gggaagcctc cccagagatg     300
caaagcaaat gtcatcaaaa aggaaaaaac aaccagacgg agtgctttaa ccatgtgcgg     360
ttcctgcagc ggctcaattc tacccacctc tatgcatgtg ggactcacgc cttccagccc     420
ctctgtgcag ccattgatgc tgaggccttc accttgccaa ccagcttcga ggaggggaag     480
gagaagtgtc cttatgaccc agcccgtggc ttcacaggcc tcatcattga tggaggcctc     540
tacacagcca ctaggtatga attccggagc attcctgaca tccgccggag ccgccaccca     600
cactccctga aactgagga gacaccaatg cattggctca atgatgcgga gtttgtgttc     660
tccgtcctcg tgcgggagag caaggccagt gcagtgggtg atgatgacaa ggtgtactac     720
ttcttcacgg agcgtgccac tgaggagggc tctggcagct tcactcagag ccgcagcagt     780
caccgtgtgg cccgtgtggc tcgygtctgc aagggagacc tgggagggaa gaagatcctg     840
cagaagaagt ggacttcctt cctgaaagcc cgtctcatct gccacattcc actgtatgag     900
acactgcgtg gggtctgcag cctggatgct gaaacctcaa gccgtacaca cttctatgca     960
gccttcacgc tgagcacaca gtggaagacc ctggaggcct cagccatctg ccgctatgac    1020
ctggcagaga tccaggctgt ctttgcagga ccctatatgg aataccagga tggttcccgg    1080
cgctggggtc gctatgaggg tgggtgcct gagcccggc ctggctcgtg tatcacagat    1140
tcattgcgca gccaaggcta caattcatcc caagacttgc catccctggt cctggacttt    1200
```

-continued

```
gtaaagttgc acccactgat ggctcggccc gttgtgccca cacgtggacg cccctgctg    1260 ctcaagcgca acatacgcta cacacacctt acagggacac ctgtcaccac gcctgctgga    1320
cctacctatg acctgctctt tctgggcaca gctgatggct ggatccacaa ggccgtagtc    1380
ctgggctctg ggatgcacat tattgaagag acacaagtgt tcagggagtc ccagtctgtg    1440
gaaaatctag tcatctctct attgcagcac agcctctatg tggggctcc tagcggagtc     1500 atccagctac cactctccag ctgctcccgc taccgatcct gctatgactg catcttggcc    1560
cgagacccct actgtggctg ggaccctggc acccatgcct gcgcagcagc caccaccata    1620
gccaacaggt cccagggaag caggacagca ctgatacagg acatagagag aggaaatcga    1680
ggctgtgaga gcagcaggga tacagggcca ccaccaccac tgaagacccg ctctgtgctc    1740
cggggtgatg atgtcctcct gccctgtgac cagccatcca acctggcccg ggccttgtgg    1800
ctactcaatg ggagcatggg cctgagcgat gggcagggtg gctaccgtgt gggcgtggac    1860
gggctgctgg ttacagatgc acagcctgag cacagtggca actatggctg ctatgccgag    1920
gaaaatggcc tccgcaccct gctggcctcc tatagtctca cagtccggcc agccactcct    1980
gccccagctc aaaagcccc tgccacacct ggggcacagc tggcacctga tgtgagactg    2040
ctctatgtgc tagccattgc cgcgcttggt ggccyctgcc tcatcctggc ctcctccctc    2100
ctctatgtgg cctgtctgcg ggaaggcaga cgagggcgcc gacggaaata ctcactgggt    2160
cgggccagcc gggcaggagg atctgcggtc aactgcaga cagtctcagg cagggctctg    2220
caggtccata tgggctcaat gtcaccaccc tctgcatggc cctgtgtgct ggatggtcct    2280
gaaaccagac aagtcctctg ccagccacct aagccctgcg tacattcaca tgcacacatg    2340
gaagaatgtt tatcggctgg gctgcagtgc ccccaccctc accttctcct ggtgcattct    2400
tgtttcatcc ctgcttctgg acttggggta ccctcccaat tgccacatcc tatctggtcc    2460
tcttccccag ccccatgtgg tgacctcttt gtcaagagct tgggaacggg ccagcctggg    2520
gaggtaagac tgcatcactc ccctcctctc ccttcctgtg tggcccttgt gaatcagcct    2580
ccccactctc cttggtcatt ctcaagagta tga                                2613
```

<210> SEQ ID NO 31
<211> LENGTH: 870
<212> TYPE: PRT
<213> ORGANISM: homo sapiens

<400> SEQUENCE: 31

Met Trp Gly Arg Leu Trp Pro Leu Leu Leu Ser Ile Leu Thr Ala Thr
1               5                   10                  15

Ala Val Pro Gly Pro Ser Leu Arg Arg Pro Ser Arg Glu Leu Asp Ala
                20                  25                  30

Thr Pro Arg Met Thr Ile Pro Tyr Glu Glu Leu Ser Gly Thr Arg His
            35                  40                  45

Phe Lys Gly Gln Ala Gln Asn Tyr Ser Thr Leu Leu Leu Glu Ala
        50                  55                  60

Ser Ala Arg Leu Leu Val Gly Ala Arg Gly Ala Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr

-continued

```
            115                 120                 125
His Leu Tyr Ala Cys Gly Thr His Ala Phe Gln Pro Leu Cys Ala Ala
        130                 135                 140
Ile Asp Ala Glu Ala Phe Thr Leu Pro Thr Ser Phe Glu Glu Gly Lys
145                 150                 155                 160
Glu Lys Cys Pro Tyr Asp Pro Ala Arg Gly Phe Thr Gly Leu Ile Ile
                165                 170                 175
Asp Gly Gly Leu Tyr Thr Ala Thr Arg Tyr Glu Phe Arg Ser Ile Pro
            180                 185                 190
Asp Ile Arg Arg Ser Arg His Pro His Ser Leu Arg Thr Glu Glu Thr
        195                 200                 205
Pro Met His Trp Leu Asn Asp Ala Glu Phe Val Phe Ser Val Leu Val
    210                 215                 220
Arg Glu Ser Lys Ala Ser Ala Val Gly Asp Asp Lys Val Tyr Tyr
225                 230                 235                 240
Phe Phe Thr Glu Arg Ala Thr Glu Glu Gly Ser Gly Ser Phe Thr Gln
                245                 250                 255
Ser Arg Ser Ser His Arg Val Ala Arg Val Ala Arg Val Cys Lys Gly
            260                 265                 270
Asp Leu Gly Gly Lys Lys Ile Leu Gln Lys Lys Trp Thr Ser Phe Leu
        275                 280                 285
Lys Ala Arg Leu Ile Cys His Ile Pro Leu Tyr Glu Thr Leu Arg Gly
    290                 295                 300
Val Cys Ser Leu Asp Ala Glu Thr Ser Ser Arg Thr His Phe Tyr Ala
305                 310                 315                 320
Ala Phe Thr Leu Ser Thr Gln Trp Lys Thr Leu Glu Ala Ser Ala Ile
                325                 330                 335
Cys Arg Tyr Asp Leu Ala Glu Ile Gln Ala Val Phe Ala Gly Pro Tyr
            340                 345                 350
Met Glu Tyr Gln Asp Gly Ser Arg Arg Trp Gly Arg Tyr Glu Gly Gly
        355                 360                 365
Val Pro Glu Pro Arg Pro Gly Ser Cys Ile Thr Asp Ser Leu Arg Ser
    370                 375                 380
Gln Gly Tyr Asn Ser Ser Gln Asp Leu Pro Ser Leu Val Leu Asp Phe
385                 390                 395                 400
Val Lys Leu His Pro Leu Met Ala Arg Pro Val Val Pro Thr Arg Gly
                405                 410                 415
Arg Pro Leu Leu Leu Lys Arg Asn Ile Arg Tyr Thr His Leu Thr Gly
            420                 425                 430
Thr Pro Val Thr Thr Pro Ala Gly Pro Thr Tyr Asp Leu Leu Phe Leu
        435                 440                 445
Gly Thr Ala Asp Gly Trp Ile His Lys Ala Val Val Leu Gly Ser Gly
    450                 455                 460
Met His Ile Ile Glu Glu Thr Gln Val Phe Arg Glu Ser Gln Ser Val
465                 470                 475                 480
Glu Asn Leu Val Ile Ser Leu Leu Gln His Ser Leu Tyr Val Gly Ala
                485                 490                 495
Pro Ser Gly Val Ile Gln Leu Pro Leu Ser Ser Cys Ser Arg Tyr Arg
            500                 505                 510
Ser Cys Tyr Asp Cys Ile Leu Ala Arg Asp Pro Tyr Cys Gly Trp Asp
        515                 520                 525
Pro Gly Thr His Ala Cys Ala Ala Thr Thr Ile Ala Asn Arg Ser
    530                 535                 540
```

```
Gln Gly Ser Arg Thr Ala Leu Ile Gln Asp Ile Glu Arg Gly Asn Arg
545                 550                 555                 560

Gly Cys Glu Ser Ser Arg Asp Thr Gly Pro Pro Pro Leu Lys Thr
            565                 570                 575

Arg Ser Val Leu Arg Gly Asp Val Leu Pro Cys Asp Gln Pro
        580                 585                 590

Ser Asn Leu Ala Arg Ala Leu Trp Leu Leu Asn Gly Ser Met Gly Leu
            595                 600                 605

Ser Asp Gly Gln Gly Gly Tyr Arg Val Gly Val Asp Gly Leu Leu Val
        610                 615                 620

Thr Asp Ala Gln Pro Glu His Ser Gly Asn Tyr Gly Cys Tyr Ala Glu
625                 630                 635                 640

Glu Asn Gly Leu Arg Thr Leu Leu Ala Ser Tyr Ser Leu Thr Val Arg
                645                 650                 655

Pro Ala Thr Pro Ala Pro Ala Pro Lys Ala Pro Ala Thr Pro Gly Ala
            660                 665                 670

Gln Leu Ala Pro Asp Val Arg Leu Leu Tyr Val Leu Ala Ile Ala Ala
        675                 680                 685

Leu Gly Gly Leu Cys Leu Ile Leu Ala Ser Ser Leu Leu Tyr Val Ala
690                 695                 700

Cys Leu Arg Glu Gly Arg Arg Gly Arg Arg Arg Lys Tyr Ser Leu Gly
705                 710                 715                 720

Arg Ala Ser Arg Ala Gly Gly Ser Ala Val Gln Leu Gln Thr Val Ser
            725                 730                 735

Gly Arg Ala Leu Gln Val His Met Gly Ser Met Ser Pro Ser Ala
        740                 745                 750

Trp Pro Cys Val Leu Asp Gly Pro Glu Thr Arg Gln Val Leu Cys Gln
        755                 760                 765

Pro Pro Lys Pro Cys Val His Ser His Ala His Met Glu Glu Cys Leu
        770                 775                 780

Ser Ala Gly Leu Gln Cys Pro His Pro His Leu Leu Leu Val His Ser
785                 790                 795                 800

Cys Phe Ile Pro Ala Ser Gly Leu Gly Val Pro Ser Gln Leu Pro His
            805                 810                 815

Pro Ile Trp Ser Ser Pro Ala Pro Cys Gly Asp Leu Phe Val Lys
            820                 825                 830

Ser Leu Gly Thr Gly Gln Pro Gly Glu Val Arg Leu His His Ser Pro
        835                 840                 845

Pro Leu Pro Ser Cys Val Ala Leu Val Asn Gln Pro Pro His Ser Pro
850                 855                 860

Trp Ser Phe Ser Arg Val
865                 870

<210> SEQ ID NO 32
<211> LENGTH: 2598
<212> TYPE: DNA
<213> ORGANISM: homo sapiens

<400> SEQUENCE: 32
atgtggggga ggctctggcc cctcctcctc agcatcctca cagcaactgc agtcccagga      60
ccctcactgc ggagaccgtc tagagaacta gatgccaccc ctcggatgac catacccta     120 gaagagctct ctgggacccg gcacttcaag ggccaagcca gaactactc aacactgctg      180 ctggaggagg cctcagcaag gctgctggtg ggagcccgag gtgccctgtt ctctctcagt     240
```

-continued

```
gccaacgaca taggagatgg ggctcacaaa gagatccact gggaagcctc cccagagatg    300
caaagcaaat gtcatcaaaa agggaaaaac aaccagacgg agtgctttaa ccatgtgcgg    360
ttcctgcagc ggctcaattc tacccacctc tatgcatgtg ggactcacgc cttccagccc    420
ctctgtgcag ccattgatgc tgaggccttc accttgccaa ccagcttcga ggaggggaag    480
gagaagtgtc cttatgaccc agcccgtggc ttcacaggcc tcatcattga tggaggcctc    540
tacacagcca ctaggtatga attccggagc attcctgaca tccgccggag ccgccaccca    600
cactccctga gaactgagga gacaccaatg cattggctca atgatgcgga gtttgtgttc    660
tccgtcctcg tgcgggagag caaggccagt gcagtgggtg atgatgacaa ggtgtactac    720
ttcttcacgg agcgtgccac tgaggagggc tctggcagct tcactcagag ccgcagcagt    780
caccgtgtgg cccgtgtggc tcgygtctgc aagggagacc tgggagggaa gaagatcctg    840
cagaagaagt ggacttcctt cctgaaagcc cgtctcatct gccacattcc actgtatgag    900
acactgcgtg gggtctgcag cctggatgct gaaacctcaa gccgtacaca cttctatgca    960
gccttcacgc tgagcacaca gtggaagacc ctggaggcct cagccatctg ccgctatgac   1020
ctggcagaga tccaggctgt ctttgcagga ccctatatgg aataccagga tggttcccgg   1080
cgctggggtc gctatgaggg tggggtgcct gagccccggc ctggctcgtg tatcacagat   1140
tcattgcgca gccaaggcta caattcatcc caagacttgc catccctggt cctggacttt   1200
gtaaagttgc acccactgat ggctcggccc gttgtgccca cacgtggacg gcccctgctg   1260
ctcaagcgca acatacgcta cacacacctt acagggacac ctgtcaccac gcctgctgga   1320
cctacctatg acctgctctt tctgggcaca gctgatggct ggatccacaa ggccgtagtc   1380
ctgggctctg ggatgcacat tattgaagag acacaagtgt tcagggagtc ccagtctgtg   1440
gaaaatctag tcatctctct attgcagcac agcctctatg tggggctcc tagcggagtc   1500 atccagctac cactctccag ctgctcccgc taccgatcct gctatgactg catcttggcc   1560
cgagacccct actgtggctg ggaccctggc cccatgcct cgcagcagc caccaccata   1620 gccaacagga cagcactgat acaggacata gagagaggaa atcgaggctg tgagagcagc   1680
agggatacag gccaccacc accactgaag acccgctctg tgctccgggg tgatgatgtc   1740
ctcctgccct gtgaccagcc atccaacctg gcccgggcct tgtggctact caatgggagc   1800
atgggcctga gcgatgggca gggtggctac cgtgtgggcg tggacgggct gctggttaca   1860
gatgcacagc ctgagcacag tggcaactat ggctgctatg ccgaggaaaa tggcctccgc   1920
accctgctgg cctcctatag tctcacagtc cggccagcca tcctgccccc agctccaaaa    1980 gccccctgcca cacctgggc acagctggca cctgatgtga actgctcta tgtgctagcc    2040 attgccgcgc ttggtggccy ctgcctcatc ctggcctcct ccctcctcta tgtggcctgt    2100
ctgcgggaag gcagacgagg gcgccgacgg aaatactcac tgggtcgggc cagccgggca    2160
ggaggatctg cggtgcaact gcagacagtc tcaggcaggg ctctgcaggt ccatatgggc    2220
tcaatgtcac cacccctctgc atggccctgt gtgctggatg tcctgaaaac cagacaagtc    2280
ctctgccagc cacctaagcc ctgcgtacat tcacatgcac acatggaaga atgtttatcg    2340
gctgggctgc agtgccccca ccctcacctt tcctggtgc attcttgttt catccctgct    2400
tctggacttg gggtaccctc ccaattgcca catcctatct ggtcctcttc cccagcccca    2460
tgtggtgacc tcttttgtcaa gagcttggga acgggccagc ctggggaggt aagactgcat    2520
cactcccctc ctctcccttc ctgtgtggcc cttgtgaatc agcctcccca ctctccttgg    2580
```
tcattctcaa gagtatga 2598

<210> SEQ ID NO 33
<211> LENGTH: 865
<212> TYPE: PRT
<213> ORGANISM: homo sapiens

<400> SEQUENCE: 33

Met Trp Gly Arg Leu Trp Pro Leu Leu Leu Ser Ile Leu Thr Ala Thr
1               5                   10                  15

Ala Val Pro Gly Pro Ser Leu Arg Arg Pro Ser Arg Glu Leu Asp Ala
            20                  25                  30

Thr Pro Arg Met Thr Ile Pro Tyr Glu Glu Leu Ser Gly Thr Arg His
        35                  40                  45

Phe Lys Gly Gln Ala Gln Asn Tyr Ser Thr Leu Leu Leu Glu Glu Ala
    50                  55                  60

Ser Ala Arg Leu Leu Val Gly Ala Arg Gly Leu Phe Ser Leu Ser
65                  70                  75                  80

Ala Asn Asp Ile Gly Asp Gly Ala His Lys Glu Ile His Trp Glu Ala
                85                  90                  95

Ser Pro Glu Met Gln Ser Lys Cys His Gln Lys Gly Lys Asn Asn Gln
            100                 105                 110

Thr Glu Cys Phe Asn His Val Arg Phe Leu Gln Arg Leu Asn Ser Thr
        115                 120                 125

His Leu Tyr Ala Cys Gly Thr His Ala Phe Gln Pro Leu Cys Ala Ala
    130                 135                 140

Ile Asp Ala Glu Ala Phe Thr Leu Pro Thr Ser Phe Glu Glu Gly Lys
145                 150                 155                 160

Glu Lys Cys Pro Tyr Asp Pro Ala Arg Gly Phe Thr Gly Leu Ile Ile
                165                 170                 175

Asp Gly Gly Leu Tyr Thr Ala Thr Arg Tyr Glu Phe Arg Ser Ile Pro
            180                 185                 190

Asp Ile Arg Arg Ser Arg His Pro His Ser Leu Arg Thr Glu Glu Thr
        195                 200                 205

Pro Met His Trp Leu Asn Asp Ala Glu Phe Val Phe Ser Val Leu Val
    210                 215                 220

Arg Glu Ser Lys Ala Ser Ala Val Gly Asp Asp Lys Val Tyr Tyr
225                 230                 235                 240

Phe Phe Thr Glu Arg Ala Thr Glu Glu Gly Ser Gly Ser Phe Thr Gln
                245                 250                 255

Ser Arg Ser Ser His Arg Val Ala Arg Val Ala Arg Val Cys Lys Gly
            260                 265                 270

Asp Leu Gly Gly Lys Lys Ile Leu Gln Lys Lys Trp Thr Ser Phe Leu
        275                 280                 285

Lys Ala Arg Leu Ile Cys His Ile Pro Leu Tyr Glu Thr Leu Arg Gly
    290                 295                 300

Val Cys Ser Leu Asp Ala Glu Thr Ser Ser Arg Thr His Phe Tyr Ala
305                 310                 315                 320

Ala Phe Thr Leu Ser Thr Gln Trp Lys Thr Leu Glu Ala Ser Ala Ile
                325                 330                 335

Cys Arg Tyr Asp Leu Ala Glu Ile Gln Ala Val Phe Ala Gly Pro Tyr
            340                 345                 350

Met Glu Tyr Gln Asp Gly Ser Arg Trp Gly Arg Tyr Glu Gly Gly
        355                 360                 365

-continued

```
Val Pro Glu Pro Arg Pro Gly Ser Cys Ile Thr Asp Ser Leu Arg Ser
    370                 375                 380

Gln Gly Tyr Asn Ser Ser Gln Asp Leu Pro Ser Leu Val Leu Asp Phe
385                 390                 395                 400

Val Lys Leu His Pro Leu Met Ala Arg Pro Val Val Pro Thr Arg Gly
                405                 410                 415

Arg Pro Leu Leu Leu Lys Arg Asn Ile Arg Tyr Thr His Leu Thr Gly
            420                 425                 430

Thr Pro Val Thr Thr Pro Ala Gly Pro Thr Tyr Asp Leu Leu Phe Leu
            435                 440                 445

Gly Thr Ala Asp Gly Trp Ile His Lys Ala Val Val Leu Gly Ser Gly
    450                 455                 460

Met His Ile Ile Glu Glu Thr Gln Val Phe Arg Glu Ser Gln Ser Val
465                 470                 475                 480

Glu Asn Leu Val Ile Ser Leu Leu Gln His Ser Leu Tyr Val Gly Ala
                485                 490                 495

Pro Ser Gly Val Ile Gln Leu Pro Leu Ser Ser Cys Ser Arg Tyr Arg
            500                 505                 510

Ser Cys Tyr Asp Cys Ile Leu Ala Arg Asp Pro Tyr Cys Gly Trp Asp
            515                 520                 525

Pro Gly Thr His Ala Cys Ala Ala Thr Thr Ile Ala Asn Arg Thr
    530                 535                 540

Ala Leu Ile Gln Asp Ile Glu Arg Gly Asn Arg Gly Cys Glu Ser Ser
545                 550                 555                 560

Arg Asp Thr Gly Pro Pro Pro Leu Lys Thr Arg Ser Val Leu Arg
                565                 570                 575

Gly Asp Asp Val Leu Leu Pro Cys Asp Gln Pro Ser Asn Leu Ala Arg
                580                 585                 590

Ala Leu Trp Leu Leu Asn Gly Ser Met Gly Leu Ser Asp Gly Gln Gly
            595                 600                 605

Gly Tyr Arg Val Gly Val Asp Gly Leu Leu Val Thr Asp Ala Gln Pro
    610                 615                 620

Glu His Ser Gly Asn Tyr Gly Cys Tyr Ala Glu Glu Asn Gly Leu Arg
625                 630                 635                 640

Thr Leu Leu Ala Ser Tyr Ser Leu Thr Val Arg Pro Ala Thr Pro Ala
                645                 650                 655

Pro Ala Pro Lys Ala Pro Ala Thr Pro Gly Ala Gln Leu Ala Pro Asp
            660                 665                 670

Val Arg Leu Leu Tyr Val Leu Ala Ile Ala Ala Leu Gly Gly Leu Cys
            675                 680                 685

Leu Ile Leu Ala Ser Ser Leu Leu Tyr Val Ala Cys Leu Arg Glu Gly
    690                 695                 700

Arg Arg Gly Arg Arg Lys Tyr Ser Leu Gly Arg Ala Ser Arg Ala
705                 710                 715                 720

Gly Gly Ser Ala Val Gln Leu Gln Thr Val Ser Gly Arg Ala Leu Gln
                725                 730                 735

Val His Met Gly Ser Met Ser Pro Ser Ala Trp Pro Cys Val Leu
            740                 745                 750

Asp Gly Pro Glu Thr Arg Gln Val Leu Cys Gln Pro Lys Pro Cys
            755                 760                 765

Val His Ser His Ala His Met Glu Glu Cys Leu Ser Ala Gly Leu Gln
    770                 775                 780

Cys Pro His Pro His Leu Leu Leu Val His Ser Cys Phe Ile Pro Ala
```

```
785                 790                 795                 800
Ser Gly Leu Gly Val Pro Ser Gln Leu Pro His Pro Ile Trp Ser Ser
                805                 810                 815

Ser Pro Ala Pro Cys Gly Asp Leu Phe Val Lys Ser Leu Gly Thr Gly
            820                 825                 830

Gln Pro Gly Glu Val Arg Leu His His Ser Pro Pro Leu Pro Ser Cys
        835                 840                 845

Val Ala Leu Val Asn Gln Pro Pro His Ser Pro Trp Ser Phe Ser Arg
    850                 855                 860

Val
865
```

<210> SEQ ID NO 34
<211> LENGTH: 351
<212> TYPE: DNA
<213> ORGANISM: homo sapiens

<400> SEQUENCE: 34

| | |
|---|---|
| atgcaaagca aatgtcatca aaaagggaaa acaaccaga cggagtgctt taaccatgtg | 60 |
| cggttcctgc agcggctcaa ttctacccac ctctatgcat gtgggactca cgccttccag | 120 |
| cccctctgtg cagccattga tgctgaggcc ttcaccttgc caaccagctt cgaggagggg | 180 |
| aaggagaagt gtccttatga cccagcccgt ggcttcacag gcctcatcat tgatggaggc | 240 |
| ctctacacag ccactaggta tgaattccgg agcattcctg acatccgccg gagccgccac | 300 |
| ccacactccc tgagaactga ggagacacca atgcattggc tcaatggtta g | 351 |

<210> SEQ ID NO 35
<211> LENGTH: 116
<212> TYPE: PRT
<213> ORGANISM: homo sapiens

<400> SEQUENCE: 35

```
Met Gln Ser Lys Cys His Gln Lys Gly Lys Asn Asn Gln Thr Glu Cys
 1               5                  10                  15

Phe Asn His Val Arg Phe Leu Gln Arg Leu Asn Ser Thr His Leu Tyr
            20                  25                  30

Ala Cys Gly Thr His Ala Phe Gln Pro Leu Cys Ala Ala Ile Asp Ala
        35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
            100                 105                 110

Trp Leu Asn Gly
        115
```

<210> SEQ ID NO 36
<211> LENGTH: 1194
<212> TYPE: DNA
<213> ORGANISM: homo sapiens

<400> SEQUENCE: 36

| | |
|---|---|
| atgcaaagca aatgtcatca aaaagggaaa acaaccaga cggagtgctt taaccatgtg | 60 |

-continued

```
cggttcctgc agcggctcaa ttctacccac ctctatgcat gtgggactca cgccttccag    120
cccctctgtg cagccattga tgctgaggcc ttcaccttgc caaccagctt cgaggagggg    180
aaggagaagt gtccttatga cccagcccgt ggcttcacag gcctcatcat tgatggaggc    240
ctctacacag ccactaggta tgaattccgg agcattcctg acatccgccg gagccgccac    300
ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tgcccgtgt ggctcgygtc tgcaagggag acctgggagg aagaagatc     540
ctgcagaaga gtggacttc cttcctgaaa gcccgtctca tctgccacat tccactgtat    600
agacactgc gtgggtctg cagcctggat gctgaaacct caagccgtac acacttctat    660
gcagccttca cgctgagcac acagtggaag accctggagg cctcagccat ctgccgctat    720
gacctggcag agatccaggc tgtctttgca ggaccctata tggaataccca ggatggttcc   780
cggcgctggg gtcgctatga gggtggggtg cctgagcccc ggcctggctc gtgtatcaca   840
gattcattgc gcagccaagg ctacaattca tcccaagact tgccatccct ggtcctggac   900
tttgtaaagt tgcacccact gatggctcgg cccgttgtgc ccacacgtgg acggcccctg   960
ctgctcaagc gcaacatacg ctacacacac cttacaggga cacctgtcac cacgcctgct  1020
ggacctacct atgacctgct ctttctgggc acagctgatg ctggatcca caaggccgta  1080
gtcctgggct ctgggatgca cattattgaa agacacaag tgttcaggga gtcccagtct  1140
gtggaaaatc tagtcatctc tctattgcag gtagcccttc tctgtgaccc ttaa         1194
```

<210> SEQ ID NO 37
<211> LENGTH: 397
<212> TYPE: PRT
<213> ORGANISM: homo sapiens

<400> SEQUENCE: 37

```
Met Gln Ser Lys Cys His Gln Lys Gly Lys Asn Asn Gln Thr Glu Cys
  1               5                  10                  15

Phe Asn His Val Arg Phe Leu Gln Arg Leu Asn Ser Thr His Leu Tyr
                 20                  25                  30

Ala Cys Gly Thr His Ala Phe Gln Pro Leu Cys Ala Ala Ile Asp Ala
             35                  40                  45

Glu Ala Phe Thr Leu Pro Thr Ser Phe Glu Glu Gly Lys Glu Lys Cys
         50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175
```

```
Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
            195                 200                 205

Leu Asp Ala Glu Thr Ser Ser Arg Thr His Phe Tyr Ala Ala Phe Thr
            210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
            245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
            275                 280                 285

Asn Ser Ser Gln Asp Leu Pro Ser Leu Val Leu Asp Phe Val Lys Leu
            290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
            325                 330                 335

Thr Thr Pro Ala Gly Pro Thr Tyr Asp Leu Leu Phe Leu Gly Thr Ala
            340                 345                 350

Asp Gly Trp Ile His Lys Ala Val Val Leu Gly Ser Gly Met His Ile
            355                 360                 365

Ile Glu Glu Thr Gln Val Phe Arg Glu Ser Gln Ser Val Glu Asn Leu
            370                 375                 380

Val Ile Ser Leu Leu Gln Val Ala Leu Leu Cys Asp Pro
385                 390                 395

<210> SEQ ID NO 38
<211> LENGTH: 1812
<212> TYPE: DNA
<213> ORGANISM: homo sapiens

<400> SEQUENCE: 38
atgcaaagca aatgtcatca aaaagggaaa acaaccaga cggagtgctt taaccatgtg      60
cggttcctgc agcggctcaa ttctacccac ctctatgcat gtgggactca cgccttccag    120
cccctctgtg cagccattga tgctgaggcc ttcaccttgc aaccagctt cgaggagggg     180 aaggagaagt gtccttatga cccagcccgt ggcttcacag gcctcatcat tgatggaggc    240
ctctacacag ccactaggta tgaattccgg agcattcctg acatccgccg agccgccac    300 ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tggcccgtgt ggctcgygtc tgcaagggag acctgggagg gaagaagatc    540
ctgcagaaga agtggacttc cttcctgaaa gcccgtctca tctgccacat tccactgtat    600
gagacactgc gtggggtctg cagcctggat gctgaaacct caagccgtac acacttctat    660
gcagccttca cgctgagcac acagtggaag accctggagg cctcagccat ctgccgctat    720
gacctggcag agatccaggc tgtctttgca ggaccctata tggaatacca ggatggttcc    780
cggcgctggg gtcgctatga gggtggggtg cctgagcccc ggcctggctc gtgtatcaca    840
gattcattgc gcagccaagg ctacaattca tcccaagact gccatccct ggtcctggac    900
```

-continued

```
tttgtaaagt tgcacccact gatggctcgg cccgttgtgc ccacacgtgg acggcccctg    960
ctgctcaagc gcaacatacg ctacacacac cttacaggga cacctgtcac cacgcctgct   1020
ggacctacct atgacctgct ctttctgggc acagctgatg gctggatcca caaggccgta   1080
gtcctgggct ctgggatgca cattattgaa gagacacaag tgttcaggga gtcccagtct   1140
gtggaaaatc tagtcatctc tctattgcag cacagcctct atgtggggc tcctagcgga    1200
gtcatccagc taccactctc cagctgctcc cgctaccgat cctgctatga ctgcatcttg   1260
gcccgagacc cctactgtgg ctgggaccct ggcacccatg cctgcgcagc agccaccacc   1320
atagccaaca ggtcccaggg aagcaggaca gcactgatac aggacataga gagggaaat    1380
cgaggctgtg agagcagcag ggatacaggc agggctctgc aggtccatat gggctcaatg   1440
tcaccaccct ctgcatggcc ctgtgtgctg gatggtcctg aaaccagaca gtcctctgc    1500
cagccaccta agccctgcgt acattcacat gcacacatga agaatgtttt atcggctggg   1560
ctgcagtgcc cccacccctca ccttctcctg gtgcattctt gtttcatccc tgcttctgga  1620
cttggggtac cctcccaatt gccacatcct atctggtcct cttccccagc ccatgtggt    1680
gacctctttg tcaagagctt gggaacgggc cagcctgggg aggtaagact gcatcactcc   1740
cctcctctcc cttcctgtgt ggcccttgtg aatcagcctc cccactctcc ttggtcattc   1800
tcaagagtat ga                                                       1812
```

<210> SEQ ID NO 39
<211> LENGTH: 603
<212> TYPE: PRT
<213> ORGANISM: homo sapiens

<400> SEQUENCE: 39

```
Met Gln Ser Lys Cys His Gln Lys Gly Lys Asn Asn Gln Thr Glu Cys
1               5                   10                  15

Phe Asn His Val Arg Phe Leu Gln Arg Leu Asn Ser Thr His Leu Tyr
                20                  25                  30

Ala Cys Gly Thr His Ala Phe Gln Pro Leu Cys Ala Ala Ile Asp Ala
            35                  40                  45

Glu Ala Phe Thr Leu Pro Thr Ser Phe Glu Glu Gly Lys Glu Lys Cys
        50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Thr Pro Met His
                100                 105                 110

Trp Leu Asn Asp Ala Glu Phe Val Phe Ser Val Leu Arg Glu Ser
            115                 120                 125

Lys Ala Ser Ala Val Gly Asp Asp Lys Val Tyr Tyr Phe Phe Thr
        130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
        195                 200                 205
```

-continued

```
Leu Asp Ala Glu Thr Ser Ser Arg Thr His Phe Tyr Ala Ala Phe Thr
    210                 215                 220
Leu Ser Thr Gln Trp Lys Thr Leu Glu Ala Ser Ala Ile Cys Arg Tyr
225                 230                 235                 240
Asp Leu Ala Glu Ile Gln Ala Val Phe Ala Gly Pro Tyr Met Glu Tyr
                245                 250                 255
Gln Asp Gly Ser Arg Arg Trp Gly Arg Tyr Glu Gly Val Pro Glu
                260                 265                 270
Pro Arg Pro Gly Ser Cys Ile Thr Asp Ser Leu Arg Ser Gln Gly Tyr
                275                 280                 285
Asn Ser Ser Gln Asp Leu Pro Ser Leu Val Leu Asp Phe Val Lys Leu
290                 295                 300
His Pro Leu Met Ala Arg Pro Val Val Pro Thr Arg Gly Arg Pro Leu
305                 310                 315                 320
Leu Leu Lys Arg Asn Ile Arg Tyr Thr His Leu Thr Gly Thr Pro Val
                325                 330                 335
Thr Thr Pro Ala Gly Pro Thr Tyr Asp Leu Leu Phe Leu Gly Thr Ala
                340                 345                 350
Asp Gly Trp Ile His Lys Ala Val Leu Gly Ser Gly Met His Ile
                355                 360                 365
Ile Glu Glu Thr Gln Val Phe Arg Glu Ser Gln Ser Val Glu Asn Leu
370                 375                 380
Val Ile Ser Leu Leu Gln His Ser Leu Tyr Val Gly Ala Pro Ser Gly
385                 390                 395                 400
Val Ile Gln Leu Pro Leu Ser Ser Cys Ser Arg Tyr Arg Ser Cys Tyr
                405                 410                 415
Asp Cys Ile Leu Ala Arg Asp Pro Tyr Cys Gly Trp Asp Pro Gly Thr
                420                 425                 430
His Ala Cys Ala Ala Ala Thr Ile Ala Asn Arg Ser Gln Gly Ser
                435                 440                 445
Arg Thr Ala Leu Ile Gln Asp Ile Glu Arg Gly Asn Arg Gly Cys Glu
450                 455                 460
Ser Ser Arg Asp Thr Gly Arg Ala Leu Gln Val His Met Gly Ser Met
465                 470                 475                 480
Ser Pro Pro Ser Ala Trp Pro Cys Val Leu Asp Gly Pro Glu Thr Arg
                485                 490                 495
Gln Val Leu Cys Gln Pro Pro Lys Pro Cys Val His Ser His Ala His
                500                 505                 510
Met Glu Glu Cys Leu Ser Ala Gly Leu Gln Cys Pro His Pro His Leu
                515                 520                 525
Leu Leu Val His Ser Cys Phe Ile Pro Ala Ser Gly Leu Gly Val Pro
530                 535                 540
Ser Gln Leu Pro His Pro Ile Trp Ser Ser Ser Pro Ala Pro Cys Gly
545                 550                 555                 560
Asp Leu Phe Val Lys Ser Leu Gly Thr Gly Gln Pro Gly Glu Val Arg
                565                 570                 575
Leu His His Ser Pro Pro Leu Pro Ser Cys Val Ala Leu Val Asn Gln
                580                 585                 590
Pro Pro His Ser Pro Trp Ser Phe Ser Arg Val
                595                 600
```

<210> SEQ ID NO 40
<211> LENGTH: 1797

<212> TYPE: DNA
<213> ORGANISM: homo sapiens

<400> SEQUENCE: 40

| | |
|---|---|
| atgcaaagca aatgtcatca aaaagggaaa acaaccaga cggagtgctt taaccatgtg | 60 |
| cggttcctgc agcggctcaa ttctacccac tctctatgcat gtgggactca cgccttccag | 120 |
| cccctctgtg cagccattga tgctgaggcc ttcaccttgc aaccagctt cgaggagggg | 180 |
| aaggagaagt gtccttatga cccagcccgt ggcttacag gcctcatcat tgatggaggc | 240 |
| ctctacacag ccactaggta tgaattccgg agcattcctg acatccgccg gagccgccac | 300 |
| ccacactccc tgagaactga ggagacacca atgcattggc tcaatgatgc ggagtttgtg | 360 |
| ttctccgtcc tcgtgcggga gagcaaggcc agtgcagtgg gtgatgatga caaggtgtac | 420 |
| tacttcttca cggagcgtgc cactgaggag ggctctggca gcttcactca gagccgcagc | 480 |
| agtcaccgtg tggcccgtgt ggctcgygtc tgcaagggag acctgggagg gaagaagatc | 540 |
| ctgcagaaga gtggacttc cttcctgaaa gcccgtctca tctgccacat tccactgtat | 600 |
| gagacactgc gtgggtctg cagcctggat gctgaaacct caagccgtac acacttctat | 660 |
| gcagccttca cgctgagcac acagtggaag accctggagg cctcagccat ctgccgctat | 720 |
| gacctggcag agatccaggc tgtctttgca ggaccctata tggaatacca ggatggttcc | 780 |
| cggcgctggg gtcgctatga gggtggggtg cctgagcccc ggcctggctc gtgtatcaca | 840 |
| gattcattgc gcagccaagg ctacaattca tcccaagact tgccatccct ggtcctggac | 900 |
| tttgtaaagt tgcacccact gatggctcgg cccgttgtgc ccacacgtgg acggcccctg | 960 |
| ctgctcaagc gcaacatacg ctacacacac cttacaggga cacctgtcac cacgcctgct | 1020 |
| ggacctacct atgacctgct ctttctgggc acagctgatg gctggatcca caggccgta | 1080 |
| gtcctgggct ctgggatgca cattattgaa gagacacaag tgttcaggga gtcccagtct | 1140 |
| gtggaaaatc tagtcatctc tctattgcag cacagcctct atgtgggggc tcctagcgga | 1200 |
| gtcatccagc taccactctc cagctgctcc cgctaccgat cctgctatga ctgcatcttg | 1260 |
| gcccgagacc cctactgtgg ctgggaccct ggcacccatg cctgcgcagc agccaccacc | 1320 |
| atagccaaca ggacagcact gatacaggac atagagagag gaaatcgagg ctgtgagagc | 1380 |
| agcagggata caggcagggc tctgcaggtc catatgggct caatgtcacc accctctgca | 1440 |
| tggccctgtg tgctggatgg tcctgaaacc agacaagtcc tctgccagcc acctaagccc | 1500 |
| tgcgtacatt cacatgcaca catggaagaa tgtttatcgg ctgggctgca gtgccccac | 1560 |
| cctcaccttc tcctggtgca ttcttgtttc atccctgctt ctggacttgg ggtaccctcc | 1620 |
| caattgccac atcctatctg gtcctcttcc ccagccccat gtggtgacct ctttgtcaag | 1680 |
| agcttgggaa cgggccagcc tggggaggta agactgcatc actcccctcc tctcccttcc | 1740 |
| tgtgtggccc ttgtgaatca gcctccccac tctccttggt cattctcaag agtatga | 1797 |

<210> SEQ ID NO 41
<211> LENGTH: 598
<212> TYPE: PRT
<213> ORGANISM: homo sapiens

<400> SEQUENCE: 41

Met Gln Ser Lys Cys His Gln Lys Gly Lys Asn Asn Gln Thr Glu Cys
1               5                   10                  15

Phe Asn His Val Arg Phe Leu Gln Arg Leu Asn Ser Thr His Leu Tyr
            20                  25                  30

-continued

```
Ala Cys Gly Thr His Ala Phe Gln Pro Leu Cys Ala Ala Ile Asp Ala
            35                  40                  45

Glu Ala Phe Thr Leu Pro Thr Ser Phe Glu Glu Gly Lys Glu Lys Cys
 50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Glu Thr Pro Met His
                100                 105                 110

Trp Leu Asn Asp Ala Glu Phe Val Phe Ser Val Leu Val Arg Glu Ser
            115                 120                 125

Lys Ala Ser Ala Val Gly Asp Asp Lys Val Tyr Tyr Phe Phe Thr
130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
            195                 200                 205

Leu Asp Ala Glu Thr Ser Ser Arg Thr His Phe Tyr Ala Ala Phe Thr
210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
            275                 280                 285

Asn Ser Ser Gln Asp Leu Pro Ser Leu Val Leu Asp Phe Val Lys Leu
290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Leu Gly Ser Gly Met His Ile
            355                 360                 365

Ile Glu Glu Thr Gln Val Phe Arg Glu Ser Gln Ser Val Glu Asn Leu
        370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Ala Thr Thr Ile Ala Asn Arg Thr Ala Leu Ile
            435                 440                 445

Gln Asp Ile Glu Arg Gly Asn Arg Gly Cys Glu Ser Ser Arg Asp Thr
```

```
                 450                    455                    460
Gly Arg Ala Leu Gln Val His Met Gly Ser Met Ser Pro Pro Ser Ala
465                 470                    475                 480

Trp Pro Cys Val Leu Asp Gly Pro Glu Thr Arg Gln Val Leu Cys Gln
                485                    490                    495

Pro Pro Lys Pro Cys Val His Ser His Ala His Met Glu Glu Cys Leu
            500                    505                    510

Ser Ala Gly Leu Gln Cys Pro His Pro His Leu Leu Leu Val His Ser
            515                    520                    525

Cys Phe Ile Pro Ala Ser Gly Leu Gly Val Pro Ser Gln Leu Pro His
        530                    535                    540

Pro Ile Trp Ser Ser Pro Ala Pro Cys Gly Asp Leu Phe Val Lys
545                 550                    555                 560

Ser Leu Gly Thr Gly Gln Pro Gly Glu Val Arg Leu His His Ser Pro
                565                    570                    575

Pro Leu Pro Ser Cys Val Ala Leu Val Asn Gln Pro Pro His Ser Pro
            580                    585                    590

Trp Ser Phe Ser Arg Val
        595

<210> SEQ ID NO 42
<211> LENGTH: 2235
<212> TYPE: DNA
<213> ORGANISM: homo sapiens

<400> SEQUENCE: 42
atgcaaagca atgtcatca aaagggaaa acaaccaga cggagtgctt taaccatgtg      60
cggttcctgc agcggctcaa ttctacccac ctctatgcat gtgggactca cgccttccag    120
cccctctgtg cagccattga tgctgaggcc ttcaccttgc aaccagctt cgaggagggg    180
aaggagaagt gtccttatga cccagcccgt ggcttcacag gcctcatcat tgatggaggc    240
ctctacacag ccactaggta tgaattccgg agcattcctg acatccgccg gagccgccac    300
ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tggcccgtgt ggctcgygtc tgcaagggag acctgggagg aagaagatc    540
ctgcagaaga gtggacttc cttcctgaaa gcccgtctca tctgccacat tccactgtat    600
gagacactgc gtggggtctg cagcctggat gctgaaacct caagccgtac acacttctat    660
gcagccttca cgctgagcac acagtggaag accctggagg cctcagccat ctgccgctat    720
gacctggcag agatccaggc tgtctttgca ggaccctata tggaatacca ggatggttcc    780
cggcgctggg tcgctatga gggtggggtg cctgagcccc ggcctggctc gtgtatcaca    840
gattcattgc gcagccaagg ctacaattca tcccaagact gccatccct ggtcctggac    900
tttgtaaagt tgcacccact gatggctcgg cccgttgtgc ccacacgtgg acggcccctg    960
ctgctcaagc gcaacatacg ctacacacac cttacaggga cacctgtcac cacgcctgct   1020
ggacctacct atgacctgct ctttctgggc acagctgatg ctggatcca caggccgta    1080
gtcctgggct ctgggatgca cattattgaa gagacacaag tgttcaggga gtcccagtct   1140
gtggaaaatc tagtcatctc tctattgcag cacagcctct atgtggggc tcctagcgga   1200
gtcatccagc taccactctc cagctgctcc cgctaccgat cctgctatga ctgcatcttg   1260
```

-continued

```
gcccgagacc cctactgtgg ctgggaccct ggcacccatg cctgcgcagc agccaccacc    1320
atagccaaca ggtcccaggg aagcaggaca gcactgatac aggacataga gagaggaaat    1380
cgaggctgtg agagcagcag ggatacaggg ccaccaccac cactgaagac ccgctctgtg    1440
ctccggggtg atgatgtcct cctgccctgt gaccagccat ccaacctggc ccgggccttg    1500
tggctactca atgggagcat gggcctgagc gatgggcagg gtggctaccg tgtgggcgtg    1560
gacgggctgc tggttacaga tgcacagcct gagcacagtg gcaactatgg ctgctatgcc    1620
gaggaaaatg gcctccgcac cctgctggcc tcctatagtc tcacagtccg gccagccact    1680
cctgccccag ctccaaaagc ccctgccaca cctggggcac agctggcacc tgatgtgaga    1740
ctgctctatg tgctagccat tgccgcgctt ggtggccyct gcctcatcct ggcctcctcc    1800
ctcctctatg tggcctgtct gcgggaaggc agacgagggc gccgacggaa atactcactg    1860
ggtcgggcca gccgggcagg aggatctgcg gtgcaactgc agacagtctc aggccagtgt    1920
cctggagagg aagatgaggg tgatgatgag ggggctgggg gcctggaggg cagctgtctc    1980
cagatcatcc ctggggaggg agccccagcc ccaccacccc caccgccccc accgccaccg    2040
gctgagctga ccaatggctt ggtggcactg cccagccggc tgcggaggat gaatggcaat    2100
agctatgtgc ttctgaggca gagcaacaat ggagtaccag cagggccctg ctccttcgcc    2160
gaggaactca gccgcatcct ggaaaaaagg aagcacacgc agctcgtgga gcagctagat    2220
gagagctctg tctga                                                    2235
```

<210> SEQ ID NO 43
<211> LENGTH: 744
<212> TYPE: PRT
<213> ORGANISM: homo sapiens

<400> SEQUENCE: 43

```
Met Gln Ser Lys Cys His Gln Lys Gly Lys Asn Asn Gln Thr Glu Cys
 1               5                  10                  15

Phe Asn His Val Arg Phe Leu Gln Arg Leu Asn Ser Thr His Leu Tyr
            20                  25                  30

Ala Cys Gly Thr His Ala Phe Gln Pro Leu Cys Ala Ala Ile Asp Ala
        35                  40                  45

Glu Ala Phe Thr Leu Pro Thr Ser Phe Glu Glu Gly Lys Glu Lys Cys
    50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Glu Thr Pro Met His
            100                 105                 110

Trp Leu Asn Asp Ala Glu Phe Val Phe Ser Val Leu Val Arg Glu Ser
        115                 120                 125

Lys Ala Ser Ala Val Gly Asp Asp Asp Lys Val Tyr Tyr Phe Phe Thr
    130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
```

-continued

```
            195                 200                 205
Leu Asp Ala Glu Thr Ser Ser Arg Thr His Phe Tyr Ala Ala Phe Thr
    210                 215                 220
Leu Ser Thr Gln Trp Lys Thr Leu Glu Ala Ser Ala Ile Cys Arg Tyr
225                 230                 235                 240
Asp Leu Ala Glu Ile Gln Ala Val Phe Ala Gly Pro Tyr Met Glu Tyr
                245                 250                 255
Gln Asp Gly Ser Arg Arg Trp Gly Arg Tyr Glu Gly Gly Val Pro Glu
            260                 265                 270
Pro Arg Pro Gly Ser Cys Ile Thr Asp Ser Leu Arg Ser Gln Gly Tyr
            275                 280                 285
Asn Ser Ser Gln Asp Leu Pro Ser Leu Val Leu Asp Phe Val Lys Leu
    290                 295                 300
His Pro Leu Met Ala Arg Pro Val Val Pro Thr Arg Gly Arg Pro Leu
305                 310                 315                 320
Leu Leu Lys Arg Asn Ile Arg Tyr Thr His Leu Thr Gly Thr Pro Val
                325                 330                 335
Thr Thr Pro Ala Gly Pro Thr Tyr Asp Leu Leu Phe Leu Gly Thr Ala
            340                 345                 350
Asp Gly Trp Ile His Lys Ala Val Val Leu Gly Ser Gly Met His Ile
            355                 360                 365
Ile Glu Glu Thr Gln Val Phe Arg Glu Ser Gln Ser Val Glu Asn Leu
    370                 375                 380
Val Ile Ser Leu Leu Gln His Ser Leu Tyr Val Gly Ala Pro Ser Gly
385                 390                 395                 400
Val Ile Gln Leu Pro Leu Ser Ser Cys Ser Arg Tyr Arg Ser Cys Tyr
                405                 410                 415
Asp Cys Ile Leu Ala Arg Asp Pro Tyr Cys Gly Trp Asp Pro Gly Thr
            420                 425                 430
His Ala Cys Ala Ala Ala Thr Thr Ile Ala Asn Arg Ser Gln Gly Ser
            435                 440                 445
Arg Thr Ala Leu Ile Gln Asp Ile Glu Arg Gly Asn Arg Gly Cys Glu
    450                 455                 460
Ser Ser Arg Asp Thr Gly Pro Pro Pro Leu Lys Thr Arg Ser Val
465                 470                 475                 480
Leu Arg Gly Asp Asp Val Leu Leu Pro Cys Asp Gln Pro Ser Asn Leu
                485                 490                 495
Ala Arg Ala Leu Trp Leu Leu Asn Gly Ser Met Gly Leu Ser Asp Gly
            500                 505                 510
Gln Gly Gly Tyr Arg Val Gly Val Asp Gly Leu Leu Val Thr Asp Ala
            515                 520                 525
Gln Pro Glu His Ser Gly Asn Tyr Gly Cys Tyr Ala Glu Glu Asn Gly
    530                 535                 540
Leu Arg Thr Leu Leu Ala Ser Tyr Ser Leu Thr Val Arg Pro Ala Thr
545                 550                 555                 560
Pro Ala Pro Ala Pro Lys Ala Pro Ala Thr Pro Gly Ala Gln Leu Ala
                565                 570                 575
Pro Asp Val Arg Leu Leu Tyr Val Leu Ala Ile Ala Ala Leu Gly Gly
            580                 585                 590
Leu Cys Leu Ile Leu Ala Ser Ser Leu Leu Tyr Val Ala Cys Leu Arg
            595                 600                 605
Glu Gly Arg Arg Gly Arg Arg Arg Lys Tyr Ser Leu Gly Arg Ala Ser
    610                 615                 620
```

-continued

Arg Ala Gly Gly Ser Ala Val Gln Leu Gln Thr Val Ser Gly Gln Cys
625                 630                 635                 640

Pro Gly Glu Glu Asp Glu Gly Asp Asp Glu Gly Ala Gly Gly Leu Glu
            645                 650                 655

Gly Ser Cys Leu Gln Ile Ile Pro Gly Glu Gly Ala Pro Ala Pro Pro
        660                 665                 670

Pro Pro Pro Pro Pro Pro Pro Ala Glu Leu Thr Asn Gly Leu Val
    675                 680                 685

Ala Leu Pro Ser Arg Leu Arg Arg Met Asn Gly Asn Ser Tyr Val Leu
    690                 695                 700

Leu Arg Gln Ser Asn Asn Gly Val Pro Ala Gly Pro Cys Ser Phe Ala
705                 710                 715                 720

Glu Glu Leu Ser Arg Ile Leu Glu Lys Arg Lys His Thr Gln Leu Val
                725                 730                 735

Glu Gln Leu Asp Glu Ser Ser Val
            740

<210> SEQ ID NO 44
<211> LENGTH: 2220
<212> TYPE: DNA
<213> ORGANISM: homo sapiens

<400> SEQUENCE: 44

| | |
|---|---|
| atgcaaagca aatgtcatca aaaagggaaa acaaccaga cggagtgctt taaccatgtg | 60 |
| cggttcctgc agcggctcaa ttctacccac ctctatgcat gtgggactca cgccttccag | 120 |
| cccctctgtg cagccattga tgctgaggcc ttcaccttgc aaccagctt cgaggagggg | 180 |
| aaggagaagt gtccttatga cccagcccgt ggcttcacag gcctcatcat tgatggaggc | 240 |
| ctctacacag ccactaggta tgaattccgg agcattcctg acatccgccg gagccgccac | 300 |
| ccacactccc tgagaactga ggagacacca atgcattggc tcaatgatgc ggagtttgtg | 360 |
| ttctccgtcc tcgtgcggga gagcaaggcc agtgcagtgg gtgatgatga caaggtgtac | 420 |
| tacttcttca cggagcgtgc cactgaggag ggctctggca gcttcactca gagccgcagc | 480 |
| agtcaccgtg tggcccgtgt ggctcgygtc tgcaagggag acctgggagg gaagaagatc | 540 |
| ctgcagaaga gtggacttc cttcctgaaa gcccgtctca tctgccacat tccactgtat | 600 |
| gagacactgc gtgggtctg cagcctggat gctgaaacct caagccgtac acacttctat | 660 |
| gcagccttca cgctgagcac acagtggaag accctggagg cctcagccat ctgccgctat | 720 |
| gacctggcag agatccaggc tgtctttgca ggaccctata tggaatacca ggatggttcc | 780 |
| cggcgctggg gtcgctatga gggtgggtg cctgagcccc ggcctggctc gtgtatcaca | 840 |
| gattcattgc gcagccaagg ctacaattca tcccaagact tgccatccct ggtcctggac | 900 |
| tttgtaaagt tgcacccact gatggctcgg cccgttgtgc ccacacgtgg acggcccctg | 960 |
| ctgctcaagc gcaacatacg ctacacacac cttacaggga cacctgtcac cacgcctgct | 1020 |
| ggacctacct atgacctgct ctttctgggc acagctgatg gctggatcca aaggccgta | 1080 |
| gtcctgggct ctgggatgca cattattgaa gagacacaag tgttcaggga gtcccagtct | 1140 |
| gtggaaaatc tagtcatctc tctattgcag cacagcctct atgtggggc tcctagcgga | 1200 |
| gtcatccagc taccactctc cagctgctcc cgctaccgat cctgctatga ctgcatcttg | 1260 |
| gcccgagacc cctactgtgg ctgggaccct gcacccatg cctgcgcagc agccaccacc | 1320 |
| atagccaaca ggacagcact gatacaggac atagagagag gaaatcgagg ctgtgagagc | 1380 |

-continued

```
agcagggata caggcccacc accaccactg aagacccgct ctgtgctccg gggtgatgat    1440
gtcctcctgc cctgtgacca gccatccaac ctggcccggg ccttgtggct actcaatggg    1500
agcatgggcc tgagcgatgg gcagggtggc taccgtgtgg gcgtggacgg gctgctggtt    1560
acagatgcac agcctgagca cagtggcaac tatggctgct atgccgagga aaatggcctc    1620
cgcaccctgc tggcctccta tagtctcaca gtccggccag ccactcctgc cccagctcca    1680
aaagcccctg ccacacctgg ggcacagctg gcacctgatg tgagactgct ctatgtgcta    1740
gccattgccg cgcttggtgg ccyctgcctc atcctggcct cctccctcct ctatgtggcc    1800
tgtctgcggg aaggcagacg agggcgccga cggaaatact cactgggtcg ggccagccgg    1860
gcaggaggat ctgcggtgca actgcagaca gtctcaggcc agtgtcctgg agaggaagat    1920
gagggtgatg atgagggggc tgggggcctg gagggcagct gtctccagat catccctggg    1980
gagggagccc cagccccacc accccaccg ccccaccgc caccggctga gctgaccaat    2040
ggcttggtgg cactgcccag ccggctgcgg aggatgaatg gcaatagcta tgtgcttctg    2100
aggcagagca acaatggagt accagcaggg ccctgctcct tcgccgagga actcagccgc    2160
atcctggaaa aaggaagca cacgcagctc gtggagcagc tagatgagag ctctgtctga    2220
```

<210> SEQ ID NO 45
<211> LENGTH: 739
<212> TYPE: PRT
<213> ORGANISM: homo sapiens

<400> SEQUENCE: 45

```
Met Gln Ser Lys Cys His Gln Lys Gly Lys Asn Asn Gln Thr Glu Cys
  1               5                  10                  15

Phe Asn His Val Arg Phe Leu Gln Arg Leu Asn Ser Thr His Leu Tyr
                 20                  25                  30

Ala Cys Gly Thr His Ala Phe Gln Pro Leu Cys Ala Ala Ile Asp Ala
             35                  40                  45

Glu Ala Phe Thr Leu Pro Thr Ser Phe Glu Glu Gly Lys Glu Lys Cys
         50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Glu Thr Pro Met His
                100                 105                 110

Trp Leu Asn Asp Ala Glu Phe Val Phe Ser Val Leu Arg Glu Ser
                115                 120                 125

Lys Ala Ser Ala Val Gly Asp Asp Lys Val Tyr Tyr Phe Phe Thr
                130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
                180                 185                 190

Leu Ile Cys His Ile Pro Leu Tyr Glu Thr Leu Arg Gly Val Cys Ser
                195                 200                 205

Leu Asp Ala Glu Thr Ser Ser Arg Thr His Phe Tyr Ala Ala Phe Thr
            210                 215                 220

Leu Ser Thr Gln Trp Lys Thr Leu Glu Ala Ser Ala Ile Cys Arg Tyr
```

```
225                 230                 235                 240
Asp Leu Ala Glu Ile Gln Ala Val Phe Ala Gly Pro Tyr Met Glu Tyr
                245                 250                 255
Gln Asp Gly Ser Arg Arg Trp Gly Arg Tyr Glu Gly Gly Val Pro Glu
                260                 265                 270
Pro Arg Pro Gly Ser Cys Ile Thr Asp Ser Leu Arg Ser Gln Gly Tyr
                275                 280                 285
Asn Ser Ser Gln Asp Leu Pro Ser Leu Val Leu Asp Phe Val Lys Leu
                290                 295                 300
His Pro Leu Met Ala Arg Pro Val Val Pro Thr Arg Gly Arg Pro Leu
305                 310                 315                 320
Leu Leu Lys Arg Asn Ile Arg Tyr Thr His Leu Thr Gly Thr Pro Val
                325                 330                 335
Thr Thr Pro Ala Gly Pro Thr Tyr Asp Leu Leu Phe Leu Gly Thr Ala
                340                 345                 350
Asp Gly Trp Ile His Lys Ala Val Val Leu Gly Ser Gly Met His Ile
                355                 360                 365
Ile Glu Glu Thr Gln Val Phe Arg Glu Ser Gln Ser Val Glu Asn Leu
                370                 375                 380
Val Ile Ser Leu Leu Gln His Ser Leu Tyr Val Gly Ala Pro Ser Gly
385                 390                 395                 400
Val Ile Gln Leu Pro Leu Ser Ser Cys Ser Arg Tyr Arg Ser Cys Tyr
                405                 410                 415
Asp Cys Ile Leu Ala Arg Asp Pro Tyr Cys Gly Trp Asp Pro Gly Thr
                420                 425                 430
His Ala Cys Ala Ala Ala Thr Thr Ile Ala Asn Arg Thr Ala Leu Ile
                435                 440                 445
Gln Asp Ile Glu Arg Gly Asn Arg Gly Cys Glu Ser Ser Arg Asp Thr
                450                 455                 460
Gly Pro Pro Pro Leu Lys Thr Arg Ser Val Leu Arg Gly Asp Asp
465                 470                 475                 480
Val Leu Leu Pro Cys Asp Gln Pro Ser Asn Leu Ala Arg Ala Leu Trp
                485                 490                 495
Leu Leu Asn Gly Ser Met Gly Leu Ser Asp Gly Gln Gly Gly Tyr Arg
                500                 505                 510
Val Gly Val Asp Gly Leu Leu Val Thr Asp Ala Gln Pro Glu His Ser
                515                 520                 525
Gly Asn Tyr Gly Cys Tyr Ala Glu Glu Asn Gly Leu Arg Thr Leu Leu
                530                 535                 540
Ala Ser Tyr Ser Leu Thr Val Arg Pro Ala Thr Pro Ala Pro Ala Pro
545                 550                 555                 560
Lys Ala Pro Ala Thr Pro Gly Ala Gln Leu Ala Pro Asp Val Arg Leu
                565                 570                 575
Leu Tyr Val Leu Ala Ile Ala Ala Leu Gly Gly Leu Cys Leu Ile Leu
                580                 585                 590
Ala Ser Ser Leu Leu Tyr Val Ala Cys Leu Arg Glu Gly Arg Arg Gly
                595                 600                 605
Arg Arg Arg Lys Tyr Ser Leu Gly Arg Ala Ser Arg Ala Gly Gly Ser
                610                 615                 620
Ala Val Gln Leu Gln Thr Val Ser Gly Gln Cys Pro Gly Glu Glu Asp
625                 630                 635                 640
Glu Gly Asp Asp Glu Gly Ala Gly Gly Leu Glu Gly Ser Cys Leu Gln
                645                 650                 655
```

Ile Ile Pro Gly Glu Gly Ala Pro Ala Pro Pro Pro Pro Pro Pro
            660                 665                 670

Pro Pro Pro Ala Glu Leu Thr Asn Gly Leu Val Ala Leu Pro Ser Arg
        675                 680                 685

Leu Arg Arg Met Asn Gly Asn Ser Tyr Val Leu Leu Arg Gln Ser Asn
        690                 695                 700

Asn Gly Val Pro Ala Gly Pro Cys Ser Phe Ala Glu Glu Leu Ser Arg
705                 710                 715                 720

Ile Leu Glu Lys Arg Lys His Thr Gln Leu Val Glu Gln Leu Asp Glu
                725                 730                 735

Ser Ser Val

<210> SEQ ID NO 46
<211> LENGTH: 2316
<212> TYPE: DNA
<213> ORGANISM: homo sapiens

<400> SEQUENCE: 46

| | | | | | |
|---|---|---|---|---|---|
| atgcaaagca | aatgtcatca | aaaagggaaa | acaaccaga | cggagtgctt | taaccatgtg | 60 |
| cggttcctgc | agcggctcaa | ttctacccac | ctctatgcat | gtgggactca | cgccttccag | 120 |
| cccctctgtg | cagccattga | tgctgaggcc | ttcaccttgc | caaccagctt | cgaggagggg | 180 |
| aaggagaagt | gtccttatga | cccagcccgt | ggcttacag | gcctcatcat | tgatggaggc | 240 |
| ctctacacag | ccactaggta | tgaattccgg | agcattcctg | acatccgccg | gagccgccac | 300 |
| ccacactccc | tgagaactga | ggagacacca | atgcattggc | tcaatgatgc | ggagtttgtg | 360 |
| ttctccgtcc | tcgtgcggga | gagcaaggcc | agtgcagtgg | gtgatgatga | caaggtgtac | 420 |
| tacttcttca | cggagcgtgc | cactgaggag | ggctctggca | gcttcactca | gagccgcagc | 480 |
| agtcaccgtg | tggcccgtgt | ggctcgygtc | tgcaagggag | acctggggagg | gaagaagatc | 540 |
| ctgcagaaga | gtggacttc | cttcctgaaa | gcccgtctca | tctgccacat | tccactgtat | 600 |
| gagacactgc | gtggggtctg | cagcctggat | gctgaaacct | caagccgtac | acacttctat | 660 |
| gcagccttca | cgctgagcac | acagtggaag | accctggagg | cctcagccat | ctgccgctat | 720 |
| gacctggcag | agatccaggc | tgtctttgca | ggacccttata | tggaataccca | ggatggttcc | 780 |
| cggcgctggg | gtcgctatga | gggtggggtg | cctgagcccc | ggcctggctc | gtgtatcaca | 840 |
| gattcattgc | gcagccaagg | ctacaattca | tcccaagact | tgccatccct | ggtcctggac | 900 |
| tttgtaaagt | tgcacccact | gatggctcgg | cccgttgtgc | ccacacgtgg | acggcccctg | 960 |
| ctgctcaagc | gcaacatacg | ctacacacac | cttacaggga | cacctgtcac | cacgcctgct | 1020 |
| ggacctacct | atgacctgct | ctttctgggc | acagctgatg | gctggatcca | caggccgta | 1080 |
| gtcctgggct | ctgggatgca | cattattgaa | gagacacaag | tgttcaggga | gtcccagtct | 1140 |
| gtggaaaatc | tagtcatctc | tctattgcag | cacagcctct | atgtgggggc | tcctagcgga | 1200 |
| gtcatccagc | taccactctc | cagctgctcc | cgctaccgat | cctgctatga | ctgcatcttg | 1260 |
| gcccgagacc | cctactgtgg | ctgggaccct | ggcacccatg | cctgcgcagc | agccaccacc | 1320 |
| atagccaaca | ggtcccaggg | aagcaggaca | gcactgatac | aggacataga | gagggaaat | 1380 |
| cgaggctgtg | agagcagcag | ggatacaggg | ccaccaccac | cactgaagac | ccgctctgtg | 1440 |
| ctccggggtg | atgatgtcct | cctgccctgt | gaccagccat | ccaacctggc | ccgggccttg | 1500 |
| tggctactca | atgggagcat | gggcctgagc | gatgggcagg | gtggctaccg | tgtgggcgtg | 1560 |
| gacgggctgc | tggttacaga | tgcacagcct | gagcacagtg | gcaactatgg | ctgctatgcc | 1620 |

```
gaggaaaatg gcctccgcac cctgctggcc tcctatagtc tcacagtccg gccagccact    1680
cctgccccag ctccaaaagc ccctgccaca cctggggcac agctggcacc tgatgtgaga    1740
ctgctctatg tgctagccat tgccgcgctt ggtggccyct gcctcatcct ggcctcctcc    1800
ctcctctatg tggcctgtct gcgggaaggc agacgagggc gccgacggaa atactcactg    1860
ggtcgggcca gccgggcagg aggatctgcg gtgcaactgc agacagtctc aggcagggct    1920
ctgcaggtcc atatgggctc aatgtcacca ccctctgcat ggccctgtgt gctggatggt    1980
cctgaaacca gacaagtcct ctgccagcca cctaagccct gcgtacattc acatgcacac    2040
atggaagaat gtttatcggc tgggctgcag tgcccccacc ctcaccttct cctggtgcat    2100
tcttgtttca tccctgcttc tggacttggg gtaccctccc aattgccaca tcctatctgg    2160
tcctcttccc cagccccatg tggtgacctc tttgtcaaga gcttgggaac gggccagcct    2220
ggggaggtaa gactgcatca ctcccctcct ctcccttcct gtgtggccct tgtgaatcag    2280
cctccccact ctccttggtc attctcaaga gtatga                              2316

<210> SEQ ID NO 47
<211> LENGTH: 771
<212> TYPE: PRT
<213> ORGANISM: homo sapiens

<400> SEQUENCE: 47
```

Met Gln Ser Lys Cys His Gln Lys Gly Lys Asn Asn Gln Thr Glu Cys
1               5                   10                  15

Phe Asn His Val Arg Phe Leu Gln Arg Leu Asn Ser Thr His Leu Tyr
                20                  25                  30

Ala Cys Gly Thr His Ala Phe Gln Pro Leu Cys Ala Ala Ile Asp Ala
            35                  40                  45

Glu Ala Phe Thr Leu Pro Thr Ser Phe Glu Glu Gly Lys Glu Lys Cys
        50                  55                  60

Pro Tyr Asp Pro Ala Arg Gly Phe Thr Gly Leu Ile Ile Asp Gly Gly
65                  70                  75                  80

Leu Tyr Thr Ala Thr Arg Tyr Glu Phe Arg Ser Ile Pro Asp Ile Arg
                85                  90                  95

Arg Ser Arg His Pro His Ser Leu Arg Thr Glu Thr Pro Met His
            100                 105                 110

Trp Leu Asn Asp Ala Glu Phe Val Phe Ser Val Leu Arg Glu Ser
        115                 120                 125

Lys Ala Ser Ala Val Gly Asp Asp Lys Val Tyr Tyr Phe Phe Thr
            130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                165                 170                 175

Gly Lys Lys Ile Leu Gln Lys Lys Trp Thr Ser Phe Leu Lys Ala Arg
            180                 185                 190

Leu Ile Cys His Ile Pro Leu Tyr Glu Thr Leu Arg Gly Val Cys Ser
        195                 200                 205

Leu Asp Ala Glu Thr Ser Ser Arg Thr His Phe Tyr Ala Ala Phe Thr
    210                 215                 220

Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr

```
                    245                 250                 255
Gln Asp Gly Ser Arg Arg Trp Gly Arg Tyr Glu Gly Gly Val Pro Glu
                260                 265                 270

Pro Arg Pro Gly Ser Cys Ile Thr Asp Ser Leu Arg Ser Gln Gly Tyr
                275                 280                 285

Asn Ser Ser Gln Asp Leu Pro Ser Leu Val Leu Asp Phe Val Lys Leu
            290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Val Leu Gly Ser Gly Met His Ile
            355                 360                 365

Ile Glu Glu Thr Gln Val Phe Arg Glu Ser Gln Ser Val Glu Asn Leu
370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Ala Thr Thr Ile Ala Asn Arg Ser Gln Gly Ser
            435                 440                 445

Arg Thr Ala Leu Ile Gln Asp Ile Glu Arg Gly Asn Arg Gly Cys Glu
        450                 455                 460

Ser Ser Arg Asp Thr Gly Pro Pro Pro Leu Lys Thr Arg Ser Val
465                 470                 475                 480

Leu Arg Gly Asp Asp Val Leu Leu Pro Cys Asp Gln Pro Ser Asn Leu
                485                 490                 495

Ala Arg Ala Leu Trp Leu Leu Asn Gly Ser Met Gly Leu Ser Asp Gly
            500                 505                 510

Gln Gly Gly Tyr Arg Val Gly Val Asp Gly Leu Leu Val Thr Asp Ala
        515                 520                 525

Gln Pro Glu His Ser Gly Asn Tyr Gly Cys Tyr Ala Glu Glu Asn Gly
        530                 535                 540

Leu Arg Thr Leu Leu Ala Ser Tyr Ser Leu Thr Val Arg Pro Ala Thr
545                 550                 555                 560

Pro Ala Pro Ala Pro Lys Ala Pro Ala Thr Pro Gly Ala Gln Leu Ala
                565                 570                 575

Pro Asp Val Arg Leu Leu Tyr Val Leu Ala Ile Ala Ala Leu Gly Gly
            580                 585                 590

Leu Cys Leu Ile Leu Ala Ser Ser Leu Leu Tyr Val Ala Cys Leu Arg
            595                 600                 605

Glu Gly Arg Arg Gly Arg Arg Lys Tyr Ser Leu Gly Arg Ala Ser
            610                 615                 620

Arg Ala Gly Gly Ser Ala Val Gln Leu Gln Thr Val Ser Gly Arg Ala
625                 630                 635                 640

Leu Gln Val His Met Gly Ser Met Ser Pro Ser Ala Trp Pro Cys
                645                 650                 655

Val Leu Asp Gly Pro Glu Thr Arg Gln Val Leu Cys Gln Pro Pro Lys
            660                 665                 670
```

```
Pro Cys Val His Ser His Ala His Met Glu Glu Cys Leu Ser Ala Gly
            675                 680                 685
Leu Gln Cys Pro His Pro His Leu Leu Leu Val His Ser Cys Phe Ile
        690                 695                 700
Pro Ala Ser Gly Leu Gly Val Pro Ser Gln Leu Pro His Pro Ile Trp
705                 710                 715                 720
Ser Ser Ser Pro Ala Pro Cys Gly Asp Leu Phe Val Lys Ser Leu Gly
                725                 730                 735
Thr Gly Gln Pro Gly Glu Val Arg Leu His His Ser Pro Pro Leu Pro
            740                 745                 750
Ser Cys Val Ala Leu Val Asn Gln Pro Pro His Ser Pro Trp Ser Phe
        755                 760                 765
Ser Arg Val
    770

<210> SEQ ID NO 48
<211> LENGTH: 2301
<212> TYPE: DNA
<213> ORGANISM: homo sapiens

<400> SEQUENCE: 48
atgcaaagca aatgtcatca aaaagggaaa acaaccaga  cggagtgctt taaccatgtg      60
cggttcctgc agcggctcaa ttctacccac tctctatgcat gtgggactca cgccttccag    120
cccctctgtg cagccattga tgctgaggcc ttcaccttgc aaccagcttt cgaggagggg    180
aaggagaagt gtccttatga cccagcccgt ggcttacagg cctcatcat  tgatggaggc    240
ctctacacag ccactaggta tgaattccgg agcattcctg catccgccg  agccgccac    300
ccacactccc tgagaactga ggagacacca atgcattggc tcaatgatgc ggagtttgtg    360
ttctccgtcc tcgtgcggga gagcaaggcc agtgcagtgg gtgatgatga caaggtgtac    420
tacttcttca cggagcgtgc cactgaggag ggctctggca gcttcactca gagccgcagc    480
agtcaccgtg tggcccgtgt ggctcgygtc tgcaagggag acctgggagg gaagaagatc    540
ctgcagaaga gtggacttc  cttcctgaaa gcccgtctca tctgccacat tccactgtat    600
gagacactgc gtggggtctg cagcctggat gctgaaacct caagccgtac acacttctat    660
gcagccttca cgctgagcac acagtggaag accctggagg cctcagccat tgccgctat     720
gacctggcag agatccaggc tgtctttgca ggaccctata tggaatacca ggatggttcc    780
cggcgctggg gtcgctatga gggtgggtg  cctgagcccc ggcctggctc gtgtatcaca    840
gattcattgc gcagccaagg ctacaattca tcccaagact tgccatccct ggtcctggac    900
tttgtaaagt tgcacccact gatggctcgg cccgttgtgc ccacacgtgg acggcccctg    960
ctgctcaagc gcaacatacg ctacacacac cttacaggga cacctgtcac cacgcctgct   1020
ggacctacct atgacctgct ctttctgggc acagctgatg gctggatcca aaggccgta    1080
gtcctgggct ctgggatgca cattattgaa gagacacaag tgttcaggga gtcccagtct   1140
gtggaaaatc tagtcatctc tctattgcag cacagcctct atgtgggggc tcctagcgga   1200
gtcatccagc taccactctc cagctgctcc cgctaccgat cctgctatga ctgcatcttg   1260
gcccgagacc cctactgtgg ctgggaccct ggcacccatg cctgcgcagc agccaccacc   1320
atagccaaca ggacagcact gatacaggac atagagagag gaaatcgagg ctgtgagagc   1380
agcagggata cagggccacc accaccactg aagaccgct  ctgtgctccg gggtgatgat   1440
gtcctcctgc cctgtgacca gccatccaac ctggcccggg ccttgtggct actcaatggg   1500
```

-continued

```
agcatgggcc tgagcgatgg gcagggtggc taccgtgtgg gcgtggacgg gctgctggtt   1560
acagatgcac agcctgagca cagtggcaac tatggctgct atgccgagga aaatggcctc   1620
cgcaccctgc tggcctccta tagtctcaca gtccggccag ccactcctgc cccagctcca   1680 aaagccctg  ccacacctgg ggcacagctg gcacctgatg tgagactgct ctatgtgcta    1740
gccattgccg cgcttggtgg ccyctgcctc atcctggcct cctccctcct ctatgtggcc   1800
tgtctgcggg aaggcagacg agggcgccga cggaaatact cactgggtcg ggccagccgg   1860
gcaggaggat ctgcggtgca actgcagaca gtctcaggca gggctctgca ggtccatatg   1920
ggctcaatgt caccaccctc tgcatggccc tgtgtgctgg atggtcctga accagacaa    1980 gtcctctgcc agccacctaa gccctgcgta cattcacatg cacacatgga agaatgttta   2040
tcggctgggc tgcagtgccc ccaccctcac cttctcctgg tgcattcttg tttcatccct   2100
gcttctggac ttggggtacc ctcccaattg ccacatccta tctggtcctc ttccccagcc   2160
ccatgtggtg acctctttgt caagagcttg ggaacgggcc agcctgggga ggtaagactg   2220
catcactccc ctcctctccc ttcctgtgtg gcccttgtga atcagcctcc ccactctcct   2280
tggtcattct caagagtatg a                                             2301
```

<210> SEQ ID NO 49
<211> LENGTH: 766
<212> TYPE: PRT
<213> ORGANISM: homo sapiens

<400> SEQUENCE: 49

```
Met Gln Ser Lys Cys His Gln Lys Gly Lys Asn Asn Gln Thr Glu Cys
  1               5                  10                  15

Phe Asn His Val Arg Phe Leu Gln Arg Leu Asn Ser Thr His Leu Tyr
             20                  25                  30

Ala Cys Gly Thr His Ala Phe Gln Pro Leu Cys Ala Ala Ile Asp Ala
         35                  40                  45

Glu Ala Phe Thr Leu Pro Thr Ser Phe Glu Glu Gly Lys Glu Lys Cys
     50                  55                  60

Pro Tyr Asp Pro Ala Arg Gly Phe Thr Gly Leu Ile Ile Asp Gly Gly
 65                  70                  75                  80

Leu Tyr Thr Ala Thr Arg Tyr Glu Phe Arg Ser Ile Pro Asp Ile Arg
                 85                  90                  95

Arg Ser Arg His Pro His Ser Leu Arg Thr Glu Thr Pro Met His
             100                 105                 110

Trp Leu Asn Asp Ala Glu Phe Val Phe Ser Val Leu Arg Glu Ser
             115                 120                 125

Lys Ala Ser Ala Val Gly Asp Asp Lys Val Tyr Tyr Phe Phe Thr
         130                 135                 140

Glu Arg Ala Thr Glu Glu Gly Ser Gly Ser Phe Thr Gln Ser Arg Ser
145                 150                 155                 160

Ser His Arg Val Ala Arg Val Ala Arg Val Cys Lys Gly Asp Leu Gly
                 165                 170                 175

Gly Lys Lys Ile Leu Gln Lys Lys Trp Thr Ser Phe Leu Lys Ala Arg
             180                 185                 190

Leu Ile Cys His Ile Pro Leu Tyr Glu Thr Leu Arg Gly Val Cys Ser
         195                 200                 205

Leu Asp Ala Glu Thr Ser Ser Arg Thr His Phe Tyr Ala Ala Phe Thr
     210                 215                 220
```

-continued

```
Leu Ser Thr Gln Trp Lys Thr Leu Glu Ala Ser Ala Ile Cys Arg Tyr
225                 230                 235                 240

Asp Leu Ala Glu Ile Gln Ala Val Phe Ala Gly Pro Tyr Met Glu Tyr
                245                 250                 255

Gln Asp Gly Ser Arg Arg Trp Gly Arg Tyr Glu Gly Gly Val Pro Glu
            260                 265                 270

Pro Arg Pro Gly Ser Cys Ile Thr Asp Ser Leu Arg Ser Gln Gly Tyr
            275                 280                 285

Asn Ser Ser Gln Asp Leu Pro Ser Leu Val Leu Asp Phe Val Lys Leu
290                 295                 300

His Pro Leu Met Ala Arg Pro Val Val Pro Thr Arg Gly Arg Pro Leu
305                 310                 315                 320

Leu Leu Lys Arg Asn Ile Arg Tyr Thr His Leu Thr Gly Thr Pro Val
                325                 330                 335

Thr Thr Pro Ala Gly Pro Thr Tyr Asp Leu Leu Phe Leu Gly Thr Ala
            340                 345                 350

Asp Gly Trp Ile His Lys Ala Val Val Leu Gly Ser Gly Met His Ile
            355                 360                 365

Ile Glu Glu Thr Gln Val Phe Arg Glu Ser Gln Ser Val Glu Asn Leu
370                 375                 380

Val Ile Ser Leu Leu Gln His Ser Leu Tyr Val Gly Ala Pro Ser Gly
385                 390                 395                 400

Val Ile Gln Leu Pro Leu Ser Ser Cys Ser Arg Tyr Arg Ser Cys Tyr
                405                 410                 415

Asp Cys Ile Leu Ala Arg Asp Pro Tyr Cys Gly Trp Asp Pro Gly Thr
            420                 425                 430

His Ala Cys Ala Ala Ala Thr Thr Ile Ala Asn Arg Thr Ala Leu Ile
            435                 440                 445

Gln Asp Ile Glu Arg Gly Asn Arg Gly Cys Glu Ser Ser Arg Asp Thr
450                 455                 460

Gly Pro Pro Pro Leu Lys Thr Arg Ser Val Leu Arg Gly Asp Asp
465                 470                 475                 480

Val Leu Leu Pro Cys Asp Gln Pro Ser Asn Leu Ala Arg Ala Leu Trp
                485                 490                 495

Leu Leu Asn Gly Ser Met Gly Leu Ser Asp Gly Gln Gly Gly Tyr Arg
            500                 505                 510

Val Gly Val Asp Gly Leu Leu Val Thr Asp Ala Gln Pro Glu His Ser
            515                 520                 525

Gly Asn Tyr Gly Cys Tyr Ala Glu Glu Asn Gly Leu Arg Thr Leu Leu
530                 535                 540

Ala Ser Tyr Ser Leu Thr Val Arg Pro Ala Thr Pro Ala Pro Ala Pro
545                 550                 555                 560

Lys Ala Pro Ala Thr Pro Gly Ala Gln Leu Ala Pro Asp Val Arg Leu
                565                 570                 575

Leu Tyr Val Leu Ala Ile Ala Ala Leu Gly Gly Leu Cys Leu Ile Leu
            580                 585                 590

Ala Ser Ser Leu Leu Tyr Val Ala Cys Leu Arg Glu Gly Arg Arg Gly
            595                 600                 605

Arg Arg Arg Lys Tyr Ser Leu Gly Arg Ala Ser Arg Ala Gly Gly Ser
            610                 615                 620

Ala Val Gln Leu Gln Thr Val Ser Gly Arg Ala Leu Gln Val His Met
625                 630                 635                 640

Gly Ser Met Ser Pro Pro Ser Ala Trp Pro Cys Val Leu Asp Gly Pro
```

|  |  | 645 |  |  |  | 650 |  |  |  | 655 |  |  |
|---|---|---|---|---|---|---|---|---|---|---|---|---|

Glu Thr Arg Gln Val Leu Cys Gln Pro Pro Lys Pro Cys Val His Ser
                      660                  665                 670

His Ala His Met Glu Glu Cys Leu Ser Ala Gly Leu Gln Cys Pro His
        675                  680                  685

Pro His Leu Leu Leu Val His Ser Cys Phe Ile Pro Ala Ser Gly Leu
      690                  695                  700

Gly Val Pro Ser Gln Leu Pro His Pro Ile Trp Ser Ser Ser Pro Ala
705                  710                  715                720

Pro Cys Gly Asp Leu Phe Val Lys Ser Leu Gly Thr Gly Gln Pro Gly
            725              730                  735

Glu Val Arg Leu His His Ser Pro Pro Leu Pro Ser Cys Val Ala Leu
        740                  745                  750

Val Asn Gln Pro Pro His Ser Pro Trp Ser Phe Ser Arg Val
        755                  760                765

<210> SEQ ID NO 50
<211> LENGTH: 2951
<212> TYPE: DNA
<213> ORGANISM: homo sapiens

<400> SEQUENCE: 50

```
ccgcggagcc gcgcgtcgct gtctctatgg ccccggatcc gagcgcaaag aaaacggacc      60
tcagaaaacc aggactagct ctactgtcgg gggcagggtg accccatcag taacctacaa     120
cccctctaga acttcacaac tccctctcac catggagttt gcatttgatg cagaaaggca     180
tgtgatccct ccctccttct gacctcttag ctggggattc catggccaca caaccctgtg     240
actccatgtc ccccgattca caggacccc catggcccca tgattccttg actcctatga     300
ccttatgacc cctgaccttc caagtgactt ccttggactt tgaccctgt gactgtgctt      360
cccattcccc gccccacaa cctgtgactc tggctcccctt tgggggtctt gttagtctgg     420
gcctccccag gaagatgtgg gggaggctct ggcccctcct cctcagcatc ctcacagcaa     480
ctgcagtccc aggaccctca ctgcggagac cgtctagaga actagatgcc acccctcgga     540
tgaccatacc ctatgaagag ctctctggga cccggcactt caaggccaa gcccagaact      600
actcaacact gctgctggag gaggcctcag caaggctgct ggtgggagcc cgaggtgccc     660
tgttctctct cagtgccaac gacataggag atggggctca caaagagatc cactgggaag     720
cctccccaga gatgcaaagc aaatgtcatc aaaaagggaa aaacaaccag acggagtgct     780
ttaaccatgt gcggttcctg cagcggctca attctaccca cctctatgca tgtgggactc     840
acgccttcca gccccctctgt gcagccattg atgctgaggc cttcaccttg ccaaccagct     900
tcgaggaggg gaaggagaag tgtccttatg acccagcccg tggcttcaca ggcctcatca     960
ttgatggagg cctctacaca gccactaggt atgaattccg gagcattcct gacatccgcc    1020
ggagccgcca cccacactcc ctgagaactg aggagacacc aatgcattgg ctcaatgatg    1080
cggagtttgt gttctccgtc ctcgtgcggg agagcaaggc cagtgcagtg ggtgatgatg    1140
acaaggtgta ctacttcttc acggagcgtg ccactgagga gggctctggc agcttcactc    1200
agagccgcag cagtcaccgt gtggcccgtg tggctcgygt ctgcaaggga gacctgggag    1260
ggaagaagat cctgcagaag aagtggactt ccttcctgaa agcccgtctc atctgccaca    1320
ttccactgta tgagacactg cgtgggggtct gcagcctgga tgctgaaacc tcaagccgta    1380
cacacttcta tgcagccttc acgctgagca cacagtggaa gaccctggag gcctcagcca    1440
```

-continued

```
tctgccgcta tgacctggca gagatccagg ctgtctttgc aggaccctat atggaatacc    1500
aggatggttc ccggcgctgg ggtcgctatg agggtggggt gcctgagccc cggcctggct    1560
cgtgtatcac agattcattg cgcagccaag gctacaattc atcccaagac ttgccatccc    1620
tggtcctgga ctttgtaaag ttgcacccac tgatggctcg gcccgttgtg cccacacgtg    1680
gacggcccct gctgctcaag cgcaacatac gctacacaca ccttacaggg acacctgtca    1740
ccacgcctgc tggacctacc tatgacctgc tctttctggg cacagctgat ggctggatcc    1800
acaaggccgt agtcctgggc tctgggatgc acattattga agagacacaa gtgttcaggg    1860
agtcccagtc tgtggaaaat ctagtcatct ctctattgca gcacagcctc tatgtggggg    1920
ctcctagcgg agtcatccag ctaccactct ccagctgctc ccgctaccga tcctgctatg    1980
actgcatctt ggcccgagac ccctactgtg gctgggaccc tggcacccat gcctgcgcag    2040
cagccaccac catagccaac aggacagcac tgatacagga catagagaga ggaaatcgag    2100
gctgtgagag cagcagggat acagggccac caccaccact gaagaccgc tctgtgctcc     2160 ggggtgatga tgtcctcctg ccctgtgacc agccatccaa cctggcccgg gccttgtggc    2220
tactcaatgg gagcatgggc ctgagcgatg ggcagggtgg ctaccgtgtg ggcgtggacg    2280
ggctgctggt tacagatgca cagcctgagc acagtggcaa ctatggctgc tatgccgagg    2340
aaaatggcct ccgcaccctg ctggcctcct atagtctcac agtccggcca gccactcctg    2400
ccccagctcc aaaagcccct gccacacctg gggcacagct ggcacctgat gtgagactgc    2460
tctatgtgct agccattgcc gcgcttggtg gccyctgcct catcctggcc tcctccctcc    2520
tctatgtggc ctgtctgcgg gaaggcagac gagggcgccg acggaaatac tcactgggtc    2580
gggccagccg ggcaggagga tctgcggtgc aactgcagac agtctcaggc cagtgtcctg    2640
gagaggaaga tgagggtgat gatgagggg ctgggggcct ggagggcagc tgtctccaga     2700
tcatccctgg ggagggagcc ccagcccac cacccccacc gccccaccg ccaccggctg      2760 agctgaccaa tggcttggtg gcactgccca gccggctgcg gaggatgaat ggcaatagct    2820
atgtgcttct gaggcagagc aacaatggag taccagcagg gccctgctcc ttcgccgagg    2880
aactcagccg catcctggaa aaaaggaagc acacgcagct cgtggagcag ctagatgaga    2940
gctctgtctg a                                                         2951
```